(12) United States Patent
Chen et al.

(10) Patent No.: US 11,773,167 B2
(45) Date of Patent: Oct. 3, 2023

(54) ANTI-PD-L1 ANTIBODIES AND ANTI-PD-L1/IL10 FUSION PROTEINS

(71) Applicant: ELIXIRON IMMUNOTHERAPEUTICS (HONG KONG) LIMITED, Hong Kong (CN)

(72) Inventors: Hung-Kai Chen, Los Altos, CA (US); Hong-Sen Chen, Taipei (TW); Huey-Wen Hsiao, Taipei (TW)

(73) Assignee: ELIXIRON IMMUNOTHERAPEUTICS (HONG KONG) LIMITED, Hong Kong (CN)

( * ) Notice: Subject to any disclaimer, the term of this patent is extended or adjusted under 35 U.S.C. 154(b) by 0 days.

(21) Appl. No.: 17/870,479

(22) Filed: Jul. 21, 2022

(65) Prior Publication Data

US 2023/0078173 A1 Mar. 16, 2023

Related U.S. Application Data

(63) Continuation of application No. PCT/US2021/032268, filed on May 13, 2021.

(60) Provisional application No. 63/024,855, filed on May 14, 2020.

(51) Int. Cl.
*C07K 16/28* (2006.01)
*A61P 35/00* (2006.01)
*C07K 19/00* (2006.01)

(52) U.S. Cl.
CPC .......... *C07K 16/2827* (2013.01); *A61P 35/00* (2018.01); *C07K 19/00* (2013.01); *C07K 2317/565* (2013.01)

(58) Field of Classification Search
None
See application file for complete search history.

(56) References Cited

U.S. PATENT DOCUMENTS

| 10,472,411 | B2 * | 11/2019 | Yang | C07K 16/30 |
| 2011/0112279 | A1 | 5/2011 | Ackerly, H. et al. | |
| 2019/0016814 | A1 | 1/2019 | Humphrey et al. | |
| 2019/0100583 | A1 | 4/2019 | Arnott et al. | |
| 2019/0263893 | A1 * | 8/2019 | Yang | C07K 16/18 |

FOREIGN PATENT DOCUMENTS

| WO | 2018136553 A | 7/2018 |
| WO | 2019079671 A | 4/2019 |

OTHER PUBLICATIONS

D'Angelo et al. (2018) Many Routes to an Antibody Heavy-Chain CDR3: Necessary, Yet Insufficient, for Specific Binding. Front Immunol. 9: 395 (13 pages).*
"International Search Report and the Written Opinion of the International Searching Authority" for PCT/US2021/032268, dated Nov. 5, 2021.

* cited by examiner

*Primary Examiner* — Ilia I Ouspenski
(74) *Attorney, Agent, or Firm* — FisherBroyles, LLP; Adam K. Whiting

(57) ABSTRACT

The present disclosure provides antibodies, including antibody fusions, which specifically bind to human PD-L1 protein (huPD-L1) and are capable of decreasing, inhibiting, and/or fully-blocking immune regulatory effects mediated by PD-L1, such as binding to the immune checkpoint molecule PD-1 in the tumor microenvironment. Additionally, the antibodies include fusions with the cytokine inhibitory factor, IL10, which can replenish and/or activate CD8+ T-cell cytotoxicity in the tumor microenvironment. The present disclosure also provides methods of using the antibodies (and compositions thereof) to treat diseases and conditions responsive to decreasing, inhibiting and/or blocking immune regulatory function or activity mediated by PD1 binding to PD-L1.

4 Claims, 12 Drawing Sheets

Specification includes a Sequence Listing.

SEQUENCE LISTING

```
Sequence total quantity: 180
SEQ ID NO: 1          moltype = AA  length = 10
FEATURE               Location/Qualifiers
REGION                1..10
                      note = Synthetic polypeptide
source                1..10
                      mol_type = protein
                      organism = synthetic construct
SEQUENCE: 1
GFTFSDSWIH                                                            10

SEQ ID NO: 2          moltype = AA  length = 18
FEATURE               Location/Qualifiers
REGION                1..18
                      note = Synthetic polypeptide
source                1..18
                      mol_type = protein
                      organism = synthetic construct
SEQUENCE: 2
AWISPYGGST YYADSVKG                                                   18
```

```
SEQ ID NO: 3              moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 3
RHWPGGFDY                                                                    9

SEQ ID NO: 4              moltype = AA   length = 118
FEATURE                   Location/Qualifiers
REGION                    1..118
                          note = Synthetic polypeptide
source                    1..118
                          mol_type = protein
                          organism = synthetic construct
SEQUENCE: 4
EVQLVESGGG LVQPGGSLRL SCAASGFTFS DSWIHWVRQA PGKGLEWVAW ISPYGGSTYY            60
ADSVKGRFTI SADTSKNTAY LQMNSLRAED TAVYYCARRH WPGGFDYWGQ GTLVTVSA            118

SEQ ID NO: 5              moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 5
RASQDVSTAV A                                                                11

SEQ ID NO: 6              moltype = AA   length = 7
FEATURE                   Location/Qualifiers
REGION                    1..7
                          note = Synthetic polypeptide
source                    1..7
                          mol_type = protein
                          organism = synthetic construct
SEQUENCE: 6
SASFLYS                                                                      7

SEQ ID NO: 7              moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 7
QQYLYHPAT                                                                    9

SEQ ID NO: 8              moltype = AA   length = 107
FEATURE                   Location/Qualifiers
REGION                    1..107
                          note = Synthetic polypeptide
source                    1..107
                          mol_type = protein
                          organism = synthetic construct
SEQUENCE: 8
DIQMTQSPSS LSASVGDRVT ITCRASQDVS TAVAWQQKPG KAPKLLIYSA SFLYSGVPSR            60
FSGSGSGTDF TLTISSLQPE DFATYYCQQY LYHPATFGQG TKVEIKR                        107

SEQ ID NO: 9              moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 9
SYIMM                                                                        5

SEQ ID NO: 10             moltype = AA   length = 17
FEATURE                   Location/Qualifiers
REGION                    1..17
                          note = Synthetic polypeptide
```

```
source                  1..17
                        mol_type = protein
                        organism = synthetic construct
SEQUENCE: 10
SIYPSGGITF YADTVKG                                              17

SEQ ID NO: 11           moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 11
IKLGTVTTVD Y                                                    11

SEQ ID NO: 12           moltype = AA   length = 120
FEATURE                 Location/Qualifiers
REGION                  1..120
                        note = Synthetic polypeptide
source                  1..120
                        mol_type = protein
                        organism = synthetic construct
SEQUENCE: 12
EVQLLESGGG LVQPGGSLRL SCAASGFTFS SYIMMWVRQA PGKGLEWVSS IYPSGGITFY   60
ADTVKGRFTI SRDNSKNTLY LQMNSLRAED TAVYYCARIK LGTVTTVDYW GQGTLVTVSS  120

SEQ ID NO: 13           moltype = AA   length = 14
FEATURE                 Location/Qualifiers
REGION                  1..14
                        note = Synthetic polypeptide
source                  1..14
                        mol_type = protein
                        organism = synthetic construct
SEQUENCE: 13
TGTSSDVGGY NYVS                                                 14

SEQ ID NO: 14           moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 14
DVSNRPS                                                          7

SEQ ID NO: 15           moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 15
SSYTSSSTRV                                                      10

SEQ ID NO: 16           moltype = AA   length = 110
FEATURE                 Location/Qualifiers
REGION                  1..110
                        note = Synthetic polypeptide
source                  1..110
                        mol_type = protein
                        organism = synthetic construct
SEQUENCE: 16
QSALTQPASV SGSPGQSITI SCTGTSSDVG GYNYVSWYQQ HPGKAPKLMI YDVSNRPSGV   60
SNRFSGSKSG NTASLTISGL QAEDEADYYC SSYTSSSTRV FGTGTKVTVL            110

SEQ ID NO: 17           moltype = AA   length = 10
FEATURE                 Location/Qualifiers
REGION                  1..10
                        note = Synthetic polypeptide
source                  1..10
                        mol_type = protein
                        organism = synthetic construct
```

```
SEQUENCE: 17
GFTFSRYWMS                                                              10

SEQ ID NO: 18          moltype = AA  length = 17
FEATURE                Location/Qualifiers
REGION                 1..17
                       note = Synthetic polypeptide
source                 1..17
                       mol_type = protein
                       organism = synthetic construct
SEQUENCE: 18
NIKQDGSEKY YVDSVKG                                                      17

SEQ ID NO: 19          moltype = AA  length = 12
FEATURE                Location/Qualifiers
REGION                 1..12
                       note = Synthetic polypeptide
source                 1..12
                       mol_type = protein
                       organism = synthetic construct
SEQUENCE: 19
EGGWFGELAF DY                                                           12

SEQ ID NO: 20          moltype = AA  length = 121
FEATURE                Location/Qualifiers
REGION                 1..121
                       note = Synthetic polypeptide
source                 1..121
                       mol_type = protein
                       organism = synthetic construct
SEQUENCE: 20
EVQLVESGGG LVQPGGSLRL SCAASGFTFS RYWMSWVRQA PGKGLEWVAN IKQDGSEKYY        60
VDSVKGRFTI SRDNAKNSLY LQMNSLRAED TAVYYCAREG GWFGELAFDY WGQGTLVTVS       120
S                                                                      121

SEQ ID NO: 21          moltype = AA  length = 12
FEATURE                Location/Qualifiers
REGION                 1..12
                       note = Synthetic polypeptide
source                 1..12
                       mol_type = protein
                       organism = synthetic construct
SEQUENCE: 21
RASQRVSSSY LA                                                           12

SEQ ID NO: 22          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 22
DASSRAT                                                                 7

SEQ ID NO: 23          moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 23
QQYGSLPWT                                                               9

SEQ ID NO: 24          moltype = AA  length = 108
FEATURE                Location/Qualifiers
REGION                 1..108
                       note = Synthetic polypeptide
source                 1..108
                       mol_type = protein
                       organism = synthetic construct
SEQUENCE: 24
EIVLTQSPGT LSLSPGERAT LSCRASQRVS SSYLAWYQQK PGQAPRLLIY DASSRATGIP        60
DRFSGSGSGT DFTLTISRLE PEDFAWYYCQ QYGSLPWTFG QGTKVEIK                    108
```

```
SEQ ID NO: 25           moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 25
KASGGTFSSY AIS                                                         13

SEQ ID NO: 26           moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 26
GIIPIFGTAN YAQKFQG                                                     17

SEQ ID NO: 27           moltype = AA   length = 16
FEATURE                 Location/Qualifiers
REGION                  1..16
                        note = Synthetic polypeptide
source                  1..16
                        mol_type = protein
                        organism = synthetic construct
SEQUENCE: 27
ARSPDYSPYY YYGMDV                                                      16

SEQ ID NO: 28           moltype = AA   length = 123
FEATURE                 Location/Qualifiers
REGION                  1..123
                        note = Synthetic polypeptide
source                  1..123
                        mol_type = protein
                        organism = synthetic construct
SEQUENCE: 28
QVQLVQSGAE VKKPGSSVKV SCKASGGTFS SYAISWVRQA PGQGLEWMGG IIPIFGTANY       60
AQKFQGRVTI TADKSTSTAY MELSSLRSED TAVYYCARSP DYSPYYYGM DVWGQGTTVT       120
VSS                                                                    123

SEQ ID NO: 29           moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 29
SGSSSNIGSN TVN                                                         13

SEQ ID NO: 30           moltype = AA   length = 8
FEATURE                 Location/Qualifiers
REGION                  1..8
                        note = Synthetic polypeptide
source                  1..8
                        mol_type = protein
                        organism = synthetic construct
SEQUENCE: 30
YGNSNRPS                                                               8

SEQ ID NO: 31           moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 31
QSYDSSLSGS V                                                           11

SEQ ID NO: 32           moltype = AA   length = 111
FEATURE                 Location/Qualifiers
REGION                  1..111
                        note = Synthetic polypeptide
```

```
source                        1..111
                              mol_type = protein
                              organism = synthetic construct
SEQUENCE: 32
QSVLTQPPSA SGTPGQRVTI SCSGSSSNIG SNTVNWYQQL PGTAPKLLIY GNSNRPSGVP      60
DRFSGSKSGT SASLAISGLQ SEDEADYYCQ SYDSSLSGSV FGGGIKLTVL G              111

SEQ ID NO: 33                 moltype = AA   length = 5
FEATURE                       Location/Qualifiers
REGION                        1..5
                              note = Synthetic polypeptide
source                        1..5
                              mol_type = protein
                              organism = synthetic construct
SEQUENCE: 33
SYWMY                                                                   5

SEQ ID NO: 34                 moltype = AA   length = 17
FEATURE                       Location/Qualifiers
REGION                        1..17
                              note = Synthetic polypeptide
source                        1..17
                              mol_type = protein
                              organism = synthetic construct
SEQUENCE: 34
RIDPNSGSTK YNEKFKN                                                     17

SEQ ID NO: 35                 moltype = AA   length = 11
FEATURE                       Location/Qualifiers
REGION                        1..11
                              note = Synthetic polypeptide
source                        1..11
                              mol_type = protein
                              organism = synthetic construct
SEQUENCE: 35
DYRKGLYAMD Y                                                           11

SEQ ID NO: 36                 moltype = AA   length = 120
FEATURE                       Location/Qualifiers
REGION                        1..120
                              note = Synthetic polypeptide
source                        1..120
                              mol_type = protein
                              organism = synthetic construct
SEQUENCE: 36
EVQLVQSGAE VKKPGATVKI SCKVSGYTFT SYWMYWVRQA RGQRLEWIGR IDPNSGSTKY       60
NEKFKNRFTI SRDNSKNTLY LQMNSLRAED TAVYYCARDY RKGLYAMDYW GQGTTVTVSS      120

SEQ ID NO: 37                 moltype = AA   length = 11
FEATURE                       Location/Qualifiers
REGION                        1..11
                              note = Synthetic polypeptide
source                        1..11
                              mol_type = protein
                              organism = synthetic construct
SEQUENCE: 37
KASQDVGTAV A                                                           11

SEQ ID NO: 38                 moltype = AA   length = 7
FEATURE                       Location/Qualifiers
REGION                        1..7
                              note = Synthetic polypeptide
source                        1..7
                              mol_type = protein
                              organism = synthetic construct
SEQUENCE: 38
WASTRHT                                                                 7

SEQ ID NO: 39                 moltype = AA   length = 9
FEATURE                       Location/Qualifiers
REGION                        1..9
                              note = Synthetic polypeptide
source                        1..9
                              mol_type = protein
                              organism = synthetic construct
SEQUENCE: 39
QQYNSYPLT                                                               9
```

```
SEQ ID NO: 40            moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 40
AIQLTQSPSS LSASVGDRVT ITCKASQDVG TAVAWYLQKP GQSPQLLIYW ASTRHTGVPS    60
RFSGSGSGTD FTFTISSLEA EDAATYYCQQ YNSYPLTFGQ GTKVEIK                 107

SEQ ID NO: 41            moltype = AA  length = 5
FEATURE                  Location/Qualifiers
REGION                   1..5
                         note = Synthetic polypeptide
source                   1..5
                         mol_type = protein
                         organism = synthetic construct
SEQUENCE: 41
TYAIS                                                                 5

SEQ ID NO: 42            moltype = AA  length = 17
FEATURE                  Location/Qualifiers
REGION                   1..17
                         note = Synthetic polypeptide
source                   1..17
                         mol_type = protein
                         organism = synthetic construct
SEQUENCE: 42
GIIPIFGKAH YAQKFQG                                                   17

SEQ ID NO: 43            moltype = AA  length = 14
FEATURE                  Location/Qualifiers
REGION                   1..14
                         note = Synthetic polypeptide
source                   1..14
                         mol_type = protein
                         organism = synthetic construct
SEQUENCE: 43
KFHFVSGSPF GMDV                                                      14

SEQ ID NO: 44            moltype = AA  length = 123
FEATURE                  Location/Qualifiers
REGION                   1..123
                         note = Synthetic polypeptide
source                   1..123
                         mol_type = protein
                         organism = synthetic construct
SEQUENCE: 44
QVQLVQSGAE VKKPGSSVKV SCKTSGDTFS TYAISWVRQA PGQGLEWMGG IIPIFGKAHY    60
AQKFQGRVTI TADESTSTAY MELSSLRSED TAVYFCARKF HFVSGSPFGM DVWGQGTTVT   120
VSS                                                                 123

SEQ ID NO: 45            moltype = AA  length = 11
FEATURE                  Location/Qualifiers
REGION                   1..11
                         note = Synthetic polypeptide
source                   1..11
                         mol_type = protein
                         organism = synthetic construct
SEQUENCE: 45
RASQSVSSYL A                                                         11

SEQ ID NO: 46            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 46
DASNRAT                                                               7
```

```
SEQ ID NO: 47          moltype = AA   length = 8
FEATURE                Location/Qualifiers
REGION                 1..8
                       note = Synthetic polypeptide
source                 1..8
                       mol_type = protein
                       organism = synthetic construct
SEQUENCE: 47
QQRSNWPT                                                                   8

SEQ ID NO: 48          moltype = AA   length = 106
FEATURE                Location/Qualifiers
REGION                 1..106
                       note = Synthetic polypeptide
source                 1..106
                       mol_type = protein
                       organism = synthetic construct
SEQUENCE: 48
EIVLTQSPAT LSLSPGERAT LSCRASQSVS SYLAWYQQKP GQAPRLLIYD ASNRATGIPA          60
RFSGSGSGTD FTLTISSLEP EDFAVYYCQQ RSNWPTFGQG TKVEIK                        106

SEQ ID NO: 49          moltype = AA   length = 13
FEATURE                Location/Qualifiers
REGION                 1..13
                       note = Synthetic polypeptide
source                 1..13
                       mol_type = protein
                       organism = synthetic construct
SEQUENCE: 49
AASGFTITDS FIH                                                            13

SEQ ID NO: 50          moltype = AA   length = 10
FEATURE                Location/Qualifiers
REGION                 1..10
                       note = Synthetic polypeptide
source                 1..10
                       mol_type = protein
                       organism = synthetic construct
SEQUENCE: 50
RIDPYGGTTN                                                                10

SEQ ID NO: 51          moltype = AA   length = 10
FEATURE                Location/Qualifiers
REGION                 1..10
                       note = Synthetic polypeptide
source                 1..10
                       mol_type = protein
                       organism = synthetic construct
SEQUENCE: 51
ARAYSWFSDY                                                                10

SEQ ID NO: 52          moltype = AA   length = 117
FEATURE                Location/Qualifiers
REGION                 1..117
                       note = Synthetic polypeptide
source                 1..117
                       mol_type = protein
                       organism = synthetic construct
SEQUENCE: 52
EVQLVESGGG LVQPGGSLRL SCAASGFTIT DSFIHWVRQA PGKGLEWVAR IDPYGGTTNY          60
ADSVKGRFTI SADTSKNTAY LQMNSLRAED TAVYYCARAY SWFSDYWGQG TLVTVSS            117

SEQ ID NO: 53          moltype = AA   length = 11
FEATURE                Location/Qualifiers
REGION                 1..11
                       note = Synthetic polypeptide
source                 1..11
                       mol_type = protein
                       organism = synthetic construct
SEQUENCE: 53
RAGQDVYKAV A                                                              11

SEQ ID NO: 54          moltype = AA   length = 8
FEATURE                Location/Qualifiers
REGION                 1..8
                       note = Synthetic polypeptide
```

```
source                     1..8
                           mol_type = protein
                           organism = synthetic construct
SEQUENCE: 54
YWSTNLYS                                                                     8

SEQ ID NO: 55              moltype = AA   length = 8
FEATURE                    Location/Qualifiers
REGION                     1..8
                           note = Synthetic polypeptide
source                     1..8
                           mol_type = protein
                           organism = synthetic construct
SEQUENCE: 55
GSTWPLTF                                                                     8

SEQ ID NO: 56              moltype = AA   length = 107
FEATURE                    Location/Qualifiers
REGION                     1..107
                           note = Synthetic polypeptide
source                     1..107
                           mol_type = protein
                           organism = synthetic construct
SEQUENCE: 56
DIQMTQSPSS LSASVGDRVT ITCRAGQDVY KAVAWYQQKP GKAPKLLIYW STNLYSGVPS            60
RFSGSGSGTD FTLTISSLQP EDFATYYCQQ GSTWPLTFGQ GTKVEIK                         107

SEQ ID NO: 57              moltype = AA   length = 13
FEATURE                    Location/Qualifiers
REGION                     1..13
                           note = Synthetic polypeptide
source                     1..13
                           mol_type = protein
                           organism = synthetic construct
SEQUENCE: 57
AASGFTISDF GIH                                                              13

SEQ ID NO: 58              moltype = AA   length = 10
FEATURE                    Location/Qualifiers
REGION                     1..10
                           note = Synthetic polypeptide
source                     1..10
                           mol_type = protein
                           organism = synthetic construct
SEQUENCE: 58
GISPDSGNTN                                                                  10

SEQ ID NO: 59              moltype = AA   length = 11
FEATURE                    Location/Qualifiers
REGION                     1..11
                           note = Synthetic polypeptide
source                     1..11
                           mol_type = protein
                           organism = synthetic construct
SEQUENCE: 59
ARTFFRRSLD Y                                                                11

SEQ ID NO: 60              moltype = AA   length = 118
FEATURE                    Location/Qualifiers
REGION                     1..118
                           note = Synthetic polypeptide
source                     1..118
                           mol_type = protein
                           organism = synthetic construct
SEQUENCE: 60
EVQLVESGGG LVQPGGSLRL SCAASGFTIS DFGIHWVRQA PGKGLEWVAG ISPDSGNTNY            60
ADSVKGRFTI SADTSKNTAY LQMNSLRAED TAVYFCARTF FRRSLDYWGQ GTLVTVSS             118

SEQ ID NO: 61              moltype = AA   length = 11
FEATURE                    Location/Qualifiers
REGION                     1..11
                           note = Synthetic polypeptide
source                     1..11
                           mol_type = protein
                           organism = synthetic construct
SEQUENCE: 61
RASQDVSSGV A                                                                11
```

```
SEQ ID NO: 62            moltype = AA   length = 8
FEATURE                  Location/Qualifiers
REGION                   1..8
                         note = Synthetic polypeptide
source                   1..8
                         mol_type = protein
                         organism = synthetic construct
SEQUENCE: 62
SFANYLYS                                                                    8

SEQ ID NO: 63            moltype = AA   length = 8
FEATURE                  Location/Qualifiers
REGION                   1..8
                         note = Synthetic polypeptide
source                   1..8
                         mol_type = protein
                         organism = synthetic construct
SEQUENCE: 63
GSNLPFTF                                                                    8

SEQ ID NO: 64            moltype = AA   length = 107
FEATURE                  Location/Qualifiers
REGION                   1..107
                         note = Synthetic polypeptide
source                   1..107
                         mol_type = protein
                         organism = synthetic construct
SEQUENCE: 64
DIQMTQSPSS LSASVGDRVT ITCRASQDVS SGVAWYQQKP GKAPKLLISF ANYLYSGVPS           60
RFSGSGSGTD FTLTISSLQP EDFATYYCQQ GSNLPFTFGQ GTKVEIK                        107

SEQ ID NO: 65            moltype = AA   length = 13
FEATURE                  Location/Qualifiers
REGION                   1..13
                         note = Synthetic polypeptide
source                   1..13
                         mol_type = protein
                         organism = synthetic construct
SEQUENCE: 65
AASGFTISNS FIH                                                             13

SEQ ID NO: 66            moltype = AA   length = 10
FEATURE                  Location/Qualifiers
REGION                   1..10
                         note = Synthetic polypeptide
source                   1..10
                         mol_type = protein
                         organism = synthetic construct
SEQUENCE: 66
DISPYSGYTN                                                                 10

SEQ ID NO: 67            moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 67
ARTPAWGYMD Y                                                               11

SEQ ID NO: 68            moltype = AA   length = 118
FEATURE                  Location/Qualifiers
REGION                   1..118
                         note = Synthetic polypeptide
source                   1..118
                         mol_type = protein
                         organism = synthetic construct
SEQUENCE: 68
EVQLVESGGG LVQPGGSLRL SCAASGFTIS NSFIHWVRQA PGKGLEWVAD ISPYSGYTNY           60
ADSVKGRFTI SADTSKNTAY LQMNSLRAED TAVYYCARTP AWGYMDYWGQ GTLVTVSS            118
```

```
SEQ ID NO: 69            moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 69
RASQDVSSSV A                                                            11

SEQ ID NO: 70            moltype = AA   length = 8
FEATURE                  Location/Qualifiers
REGION                   1..8
                         note = Synthetic polypeptide
source                   1..8
                         mol_type = protein
                         organism = synthetic construct
SEQUENCE: 70
SWATSLYS                                                                8

SEQ ID NO: 71            moltype = AA   length = 8
FEATURE                  Location/Qualifiers
REGION                   1..8
                         note = Synthetic polypeptide
source                   1..8
                         mol_type = protein
                         organism = synthetic construct
SEQUENCE: 71
YNNFPYTF                                                                8

SEQ ID NO: 72            moltype = AA   length = 107
FEATURE                  Location/Qualifiers
REGION                   1..107
                         note = Synthetic polypeptide
source                   1..107
                         mol_type = protein
                         organism = synthetic construct
SEQUENCE: 72
DIQMTQSPSS LSASVGDRVT ITCRASQDVS SSVAWYQQKP GKAQKLLISW ATSLYSGVPS        60
RFSGSGSGTD FTLTISSLQP EDFATYYCQQ YNNFPYTFGQ GTKVEIK                     107

SEQ ID NO: 73            moltype = AA   length = 160
FEATURE                  Location/Qualifiers
REGION                   1..160
                         note = Synthetic polypeptide
source                   1..160
                         mol_type = protein
                         organism = synthetic construct
SEQUENCE: 73
SPGQGTQSEN SCTHFPGNLP NMLRDLRDAF SRVKTFFQMK DQLDNLLLKE SLLEDFKGYL        60
GCQALSEMIQ FYLEEVMPQA ENQDPDIKAH VNSLGENLKT LRLRLRRCHR FLPCENKSKA       120
VEQVKNAFNK LQEKGIYKAM SEFDIFINYI EAYMTMKIRN                             160

SEQ ID NO: 74            moltype = AA   length = 15
FEATURE                  Location/Qualifiers
REGION                   1..15
                         note = Synthetic polypeptide
source                   1..15
                         mol_type = protein
                         organism = synthetic construct
SEQUENCE: 74
LGGGGSGGGG SGGGG                                                        15

SEQ ID NO: 75            moltype = AA   length = 14
FEATURE                  Location/Qualifiers
REGION                   1..14
                         note = Synthetic polypeptide
source                   1..14
                         mol_type = protein
                         organism = synthetic construct
SEQUENCE: 75
GGGGSGGGGS GGGG                                                         14
```

-continued

```
SEQ ID NO: 76            moltype = AA   length = 15
FEATURE                  Location/Qualifiers
REGION                   1..15
                         note = Synthetic polypeptide
source                   1..15
                         mol_type = protein
                         organism = synthetic construct
SEQUENCE: 76
GGGGSGGGGS GGGGS                                                            15

SEQ ID NO: 77            moltype = AA   length = 20
FEATURE                  Location/Qualifiers
REGION                   1..20
                         note = Synthetic polypeptide
source                   1..20
                         mol_type = protein
                         organism = synthetic construct
SEQUENCE: 77
GGGGSGGGGS GGGGSGGGGS                                                       20

SEQ ID NO: 78            moltype = AA   length = 25
FEATURE                  Location/Qualifiers
REGION                   1..25
                         note = Synthetic polypeptide
source                   1..25
                         mol_type = protein
                         organism = synthetic construct
SEQUENCE: 78
GGGGSGGGGS GGGGSGGGGS GGGGS                                                 25

SEQ ID NO: 79            moltype = AA   length = 30
FEATURE                  Location/Qualifiers
REGION                   1..30
                         note = Synthetic polypeptide
source                   1..30
                         mol_type = protein
                         organism = synthetic construct
SEQUENCE: 79
GGGGSGGGGS GGGGSGGGGS GGGGSGGGGS                                            30

SEQ ID NO: 80            moltype = AA   length = 623
FEATURE                  Location/Qualifiers
REGION                   1..623
                         note = Synthetic polypeptide
source                   1..623
                         mol_type = protein
                         organism = synthetic construct
SEQUENCE: 80
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYAST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGKLG GGGSGGGGSG GGGSPGQGTQ SENSCTHFPG   480
NLPNMLRDLR DAFSRVKTFF QMKDQLDNLL LKESLLEDFK GYLGCQALSE MIQFYLEEVM   540
PQAENQDPDI KAHVNSLGEN LKTLRLRLRR CHRFLPCENK SKAVEQVKNA FNKLQEKGIY   600
KAMSEFDIFI NYIEAYMTMK IRN                                          623

SEQ ID NO: 81            moltype = AA   length = 625
FEATURE                  Location/Qualifiers
REGION                   1..625
                         note = Synthetic polypeptide
source                   1..625
                         mol_type = protein
                         organism = synthetic construct
SEQUENCE: 81
EVQLLESGGG LVQPGGSLRL SCAASGFTFS SYIMMWVRQA PGKGLEWVSS IYPSGGITFY    60
ADTVKGRFTI SRDNSKNTLY LQMNSLRAED TAVYYCARIK LGTVTTVDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP CPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK LGGGGSGGGG SGGGGSPGQG TQSENSCTHF   480
```

```
PGNLPNMLRD LRDAFSRVKT FFQMKDQLDN LLLKESLLED FKGYLGCQAL SEMIQFYLEE   540
VMPQAENQDP DIKAHVNSLG ENLKTLRLRL RRCHRFLPCE NKSKAVEQVK NAFNKLQEKG   600
IYKAMSEFDI FINYIEAYMT MKIRN                                        625

SEQ ID NO: 82           moltype = AA  length = 625
FEATURE                 Location/Qualifiers
REGION                  1..625
                        note = Synthetic polypeptide
source                  1..625
                        mol_type = protein
                        organism = synthetic construct
SEQUENCE: 82
EVQLVESGGG LVQPGGSLRL SCAASGFTFS RYWMSWVRQA PGKGLEWVAN IKQDGSEKYY    60
VDSVKGRFTI SRDNAKNSLY LQMNSLRAED TAVYYCAREG GWFGELAFDY WGQGTLVTVS   120
SASTKGPSVF PLAPSSKSTS GGTAALGCLV KDYFPPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYA   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK LGGGGSGGGG SGGGGSPGQG TQSENSCTHF   480
PGNLPNMLRD LRDAFSRVKT FFQMKDQLDN LLLKESLLED FKGYLGCQAL SEMIQFYLEE   540
VMPQAENQDP DIKAHVNSLG ENLKTLRLRL RRCHRFLPCE NKSKAVEQVK NAFNKLQEKG   600
IYKAMSEFDI FINYIEAYMT MKIRN                                        625

SEQ ID NO: 83           moltype = AA  length = 622
FEATURE                 Location/Qualifiers
REGION                  1..622
                        note = Synthetic polypeptide
source                  1..622
                        mol_type = protein
                        organism = synthetic construct
SEQUENCE: 83
EVQLVESGGG LVQPGGSLRL SCAASGFTIT DSFIHWVRQA PGKGLEWVAR IDPYGGTTNY    60
ADSVKGRFTI SADSKNTAY LQMNSLRAED TAVYYCARAY SWFSDYWGQG TLVTVSSAST   120
KGPSVFPPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYASTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKLGG GGSGGGGSGG GGSPGQGTQS ENSCTHFPGN   480
LPNMLRDLRD AFSRVKTFFQ MKDQLDNLLL KESLLEDFKG YLGCQALSEM IQFYLEEVMP   540
QAENQDPDIK AHVNSLGENL KTLRLRLRRC HRFLPCENKS KAVEQVKNAF NKLQEKGIYK   600
AMSEFDIFIN YIEAYMTMKI RN                                           622

SEQ ID NO: 84           moltype = AA  length = 623
FEATURE                 Location/Qualifiers
REGION                  1..623
                        note = Synthetic polypeptide
source                  1..623
                        mol_type = protein
                        organism = synthetic construct
SEQUENCE: 84
EVQLVESGGG LVQPGGSLRL SCAASGFTIS DFGIHWVRQA PGKGLEWVAG ISPDSGNTNY    60
ADSVKGRFTI SADTSKNTAY LQMNSLRAED TAVYFCARTF FRRSLDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYAST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGKLG GGGSGGGGSG GGGSPGQGTQ SENSCTHFPG   480
NLPNMLRDLR DAFSRVKTFF QMKDQLDNLL LKESLLEDFK GYLGCQALSE MIQFYLEEVM   540
PQAENQDPDI KAHVNSLGEN LKTLRLRLRR CHRFLPCENK SKAVEQVKNA FNKLQEKGIY   600
KAMSEFDIFI NYIEAYMTMK IRN                                          623

SEQ ID NO: 85           moltype = AA  length = 623
FEATURE                 Location/Qualifiers
REGION                  1..623
                        note = Synthetic polypeptide
source                  1..623
                        mol_type = protein
                        organism = synthetic construct
SEQUENCE: 85
EVQLVESGGG LVQPGGSLRL SCAASGFTIS NSFIHWVRQA PGKGLEWVAD ISPYSGYTNY    60
ADSVKGRFTI SADTSKNTAY LQMNSLRAED TAVYYCARTP AWGYMDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYAST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
```

```
GNVFSCSVMH EALHNHYTQK SLSLSPGKLG GGGSGGGGSG GGGSPGQGTQ SENSCTHFPG   480
NLPNMLRDLR DAFSRVKTFF QMKDQLDNLL LKESLLEDFK GYLGCQALSE MIQFYLEEVM   540
PQAENQDPDI KAHVNSLGEN LKTLRLRLRR CHRFLPCENK SKAVEQVKNA FNKLQEKGIY   600
KAMSEFDIFI NYIEAYMTMK IRN                                          623

SEQ ID NO: 86           moltype = AA   length = 406
FEATURE                 Location/Qualifiers
REGION                  1..406
                        note = Synthetic polypeptide
source                  1..406
                        mol_type = protein
                        organism = synthetic construct
SEQUENCE: 86
SPGQGTQSEN SCTHFPGNLP NMLRDLRDAF SRVKTFFQMK DQLDNLLLKE SLLEDFKGYL    60
GCQALSEMIQ FYLEEVMPQA ENQDPDIKAH VNSLGENLKT LRLRLRRCHR FLPCENKSKA   120
VEQVKNAFNK LQEKGIYKAM SEFDIFINYI EAYMTMKIRN GGGGSGGGGS GGGGSPKSCD   180
KTHTCPPCPA PELLGGPSVF LFPPKPKDTL MISRTPEVTC VVVDVSHEDP EVKFNWYVDG   240
VEVHNAKTKP REEQYNSTYR VVSVLTVLHQ DWLNGKEYKC KVSNKALPAP IEKTISKAKG   300
QPREPQVYTL PPSRDELTKN QVSLTCLVKG FYPSDIAVEW ESNGQPENNY KTTPPVLDSD   360
GSFFLYSKLT VDKSRWQQGN VFSCSVMHEA LHNHYTQKSL SLSPGK                  406

SEQ ID NO: 87           moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 87
AASGFTISDG YIH                                                      13

SEQ ID NO: 88           moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 88
RIDPLTGRTM                                                          10

SEQ ID NO: 89           moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 89
ARAFSWWPDY                                                          10

SEQ ID NO: 90           moltype = AA   length = 117
FEATURE                 Location/Qualifiers
REGION                  1..117
                        note = Synthetic polypeptide
source                  1..117
                        mol_type = protein
                        organism = synthetic construct
SEQUENCE: 90
EVQLVESGGG LVQPGGSLRL SCAASGFTIS DGYIHWVRQA PGKGLEWVAR IDPLTGRTMY    60
ADSVKGRFTI SADTSKNTAY LQMNSLRAED TAVYYCARAF SWWPDYWGQG TLVTVSS      117

SEQ ID NO: 91           moltype = AA   length = 8
FEATURE                 Location/Qualifiers
REGION                  1..8
                        note = Synthetic polypeptide
source                  1..8
                        mol_type = protein
                        organism = synthetic construct
SEQUENCE: 91
IMSPPPTF                                                             8

SEQ ID NO: 92           moltype = AA   length = 107
FEATURE                 Location/Qualifiers
REGION                  1..107
                        note = Synthetic polypeptide
source                  1..107
                        mol_type = protein
                        organism = synthetic construct
```

```
SEQUENCE: 92
DIQMTQSPSS LSASVGDRVT ITCRAGQDVY KAVAWYQQKP GKAPKLLIYW STNLYSGVPS    60
RFSGSGSGTD FTLTISSLQP EDFATYYCQQ IMSPPPTFGQ GTKVEIK                107

SEQ ID NO: 93           moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 93
AASGFTIDNT YIH                                                      13

SEQ ID NO: 94           moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 94
RIDPVSGRTR                                                          10

SEQ ID NO: 95           moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 95
ARAFSWFPDY                                                          10

SEQ ID NO: 96           moltype = AA   length = 117
FEATURE                 Location/Qualifiers
REGION                  1..117
                        note = Synthetic polypeptide
source                  1..117
                        mol_type = protein
                        organism = synthetic construct
SEQUENCE: 96
EVQLVESGGG LVQPGGSLRL SCAASGFTID NTYIHWVRQA PGKGLEWVAR IDPVSGRTRY    60
ADSVKGRFTI SADTSKNTAD LQMNSLRAED TAVYYCARAF SWFPDYWGQG TLVTVSS     117

SEQ ID NO: 97           moltype = AA   length = 8
FEATURE                 Location/Qualifiers
REGION                  1..8
                        note = Synthetic polypeptide
source                  1..8
                        mol_type = protein
                        organism = synthetic construct
SEQUENCE: 97
FGATPITF                                                             8

SEQ ID NO: 98           moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 98
DIQMTQSPSS LSASVGDRVT ITCRAGQDVY KAVAWYQQKP GKAPKLLIYW STNLYSGVPS    60
RFSGSGSGTD FTLTISSLQP EDFATYYCQQ FGATPITFGQ GTKVEIK                107

SEQ ID NO: 99           moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 99
AASGFTISDA YIH                                                      13
```

```
SEQ ID NO: 100          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 100
RIEPLSGRTD                                                              10

SEQ ID NO: 101          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 101
ARAFSWFMDY                                                              10

SEQ ID NO: 102          moltype = AA   length = 117
FEATURE                 Location/Qualifiers
REGION                  1..117
                        note = Synthetic polypeptide
source                  1..117
                        mol_type = protein
                        organism = synthetic construct
SEQUENCE: 102
EVQLVESGGG LVQPGGSLRL SCAASGFTIS DAYIHWVRQA PGKGLEWVAR IEPLSGRTDY        60
ADSVKGRFTI SADTSKNTAY LQMNSLRAED TAVYYCARAF SWFMDYWGQG TLVTVSS          117

SEQ ID NO: 103          moltype = AA   length = 8
FEATURE                 Location/Qualifiers
REGION                  1..8
                        note = Synthetic polypeptide
source                  1..8
                        mol_type = protein
                        organism = synthetic construct
SEQUENCE: 103
HDKTPTTF                                                                8

SEQ ID NO: 104          moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 104
DIQMTQSPSS LSASVGDRVT ITCRAGQDVY KAVAWYQQKP GKAPKLLIYW STNLYSGVPS        60
RFSGSGSGTD FTLMISSLQP EDFATYYCQQ HDKTPTTFGQ GTKVEIK                     107

SEQ ID NO: 105          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 105
AASGFTIEDS YIH                                                          13

SEQ ID NO: 106          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 106
RIDPITGLTH                                                              10
```

```
SEQ ID NO: 107          moltype = AA  length = 117
FEATURE                 Location/Qualifiers
REGION                  1..117
                        note = Synthetic polypeptide
source                  1..117
                        mol_type = protein
                        organism = synthetic construct
SEQUENCE: 107
EVQLVESGGG LVQPGGSLRL SCAASGFTIE DSYIHWVRQA PGKGLEWVAR IDPITGLTHY   60
ADSVKGRFTI SADTSKNTAY LQMNSLRAED TAVYYCARAF SWFPDYWGQG TLVTVSS     117

SEQ ID NO: 108          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 108
IMEPPVT                                                            7

SEQ ID NO: 109          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 109
DIQMTQSPSS LSASVGDRVT ITCRAGQDVY KAVAWYQQKP GKAPKLLIYW STNLYSGVPS   60
RFSGSGSGTD FTLTISSLQP EDFATYYCQQ IMEPPVTFGQ GTKVEIK                107

SEQ ID NO: 110          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 110
RIDPANGKTT                                                         10

SEQ ID NO: 111          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 111
ARSFSWWADY                                                         10

SEQ ID NO: 112          moltype = AA  length = 117
FEATURE                 Location/Qualifiers
REGION                  1..117
                        note = Synthetic polypeptide
source                  1..117
                        mol_type = protein
                        organism = synthetic construct
SEQUENCE: 112
EVQLVESGGG LVQPGGSLRL SCAASGFTID NTYIHWVRQA PGKGLEWVAR IDPANGKTTY   60
ADSVKGRFTI SADTSKNTAN LQMNSLRAED TAVYYCARSF SWWADYWGQG TLVTVSS     117

SEQ ID NO: 113          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 113
FNLQPTT                                                            7
```

```
SEQ ID NO: 114          moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 114
DIQMTQSPSS LSASVGDRVT ITCRAGQDVY KAVAWYQQKP GKAPKLLIYW STNLYSGVPS    60
RFSGSGSGTD FTLTISSLQP EDFATYYCQQ FNLQPTTFGQ GTKVEIK                 107

SEQ ID NO: 115          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 115
RIDPANGVTR                                                          10

SEQ ID NO: 116          moltype = AA   length = 117
FEATURE                 Location/Qualifiers
REGION                  1..117
                        note = Synthetic polypeptide
source                  1..117
                        mol_type = protein
                        organism = synthetic construct
SEQUENCE: 116
EVQLVESGGG LVQPGGSLRL SCAASGFTID NTYIHWVRQA PGKRLEWVAR IDPANGVTRY    60
ADSVKGRFTI SADTSKNTAY LQMNSLRAED TAVYYCARAF SWFPDYWGQG TLVTVSS     117

SEQ ID NO: 117          moltype = AA   length = 8
FEATURE                 Location/Qualifiers
REGION                  1..8
                        note = Synthetic polypeptide
source                  1..8
                        mol_type = protein
                        organism = synthetic construct
SEQUENCE: 117
YGIAPPTF                                                             8

SEQ ID NO: 118          moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 118
DIQMTQSPSS LSASVGDRVT ITCRAGQDVY KAVAWYQQKP GKAPKLLIYW STNLYSGVPS    60
RFSGSGSGTD FTLTISSLQP EDFATYYCQQ YGIAPPTFGQ GTKVEIK                 107

SEQ ID NO: 119          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 119
AASGFTITDG YIH                                                      13

SEQ ID NO: 120          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 120
RIDPYNGRTN                                                          10
```

-continued

```
SEQ ID NO: 121         moltype = AA    length = 117
FEATURE                Location/Qualifiers
REGION                 1..117
                       note = Synthetic polypeptide
source                 1..117
                       mol_type = protein
                       organism = synthetic construct
SEQUENCE: 121
EVQLVESGGG LVQPGGSLRL SCAASGFTIT DGYIHWVRQA PGKGLEWVAR IDPYNGRTNY    60
ADSVKGRFTI SADTSKNTAY LQMNSLRAED TAVYYCARAF SWFPDYWGQG TLVTVSS      117

SEQ ID NO: 122         moltype = AA    length = 8
FEATURE                Location/Qualifiers
REGION                 1..8
                       note = Synthetic polypeptide
source                 1..8
                       mol_type = protein
                       organism = synthetic construct
SEQUENCE: 122
HGNAPITF                                                              8

SEQ ID NO: 123         moltype = AA    length = 107
FEATURE                Location/Qualifiers
REGION                 1..107
                       note = Synthetic polypeptide
source                 1..107
                       mol_type = protein
                       organism = synthetic construct
SEQUENCE: 123
DIQMTQSPSS LSASVGDRVT ITCRAGQDVY KAVAWYQQKP GKAPKLLIYW STNLYSGVPS    60
RFSGSGSGTD FTLTISSLQP EDFATYYCQQ HGNAPITFGQ GTKVEIK                 107

SEQ ID NO: 124         moltype = AA    length = 13
FEATURE                Location/Qualifiers
REGION                 1..13
                       note = Synthetic polypeptide
source                 1..13
                       mol_type = protein
                       organism = synthetic construct
SEQUENCE: 124
AASGFTIDDT YIH                                                       13

SEQ ID NO: 125         moltype = AA    length = 10
FEATURE                Location/Qualifiers
REGION                 1..10
                       note = Synthetic polypeptide
source                 1..10
                       mol_type = protein
                       organism = synthetic construct
SEQUENCE: 125
RIDPANGMTR                                                           10

SEQ ID NO: 126         moltype = AA    length = 117
FEATURE                Location/Qualifiers
REGION                 1..117
                       note = Synthetic polypeptide
source                 1..117
                       mol_type = protein
                       organism = synthetic construct
SEQUENCE: 126
EVQLVESGGG LVQPGGSLRL SCAASGFTID DTYIHWVRQA PGKGLEWVAR IDPANGMTRY    60
ADSVKGRFMI SADTSKNTAY LQMNSLRAED TAVYYCARAF SWFPDYWGQG TLVTVSS      117

SEQ ID NO: 127         moltype = AA    length = 622
FEATURE                Location/Qualifiers
REGION                 1..622
                       note = Synthetic polypeptide
source                 1..622
                       mol_type = protein
                       organism = synthetic construct
SEQUENCE: 127
EVQLVESGGG LVQPGGSLRL SCAASGFTIS DGYIHWVRQA PGKGLEWVAR IDPLTGRTMY    60
ADSVKGRFTI SADTSKNTAY LQMNSLRAED TAVYYCARAF SWWPDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYASTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
```

```
NVFSCSVMHE ALHNHYTQKS LSLSPGKLGG GGSGGGGSGG GGSPGQGTQS ENSCTHFPGN   480
LPNMLRDLRD AFSRVKTFFQ MKDQLDNLLL KESLLEDFKG YLGCQALSEM IQFYLEEVMP   540
QAENQDPDIK AHVNSLGENL KTLRLRLRRC HRFLPCENKS KAVEQVKNAF NKLQEKGIYK   600
AMSEFDIFIN YIEAYMTMKI RN                                           622

SEQ ID NO: 128          moltype = AA   length = 214
FEATURE                 Location/Qualifiers
REGION                  1..214
                        note = Synthetic polypeptide
source                  1..214
                        mol_type = protein
                        organism = synthetic construct
SEQUENCE: 128
DIQMTQSPSS LSASVGDRVT ITCRAGQDVY KAVAWYQQKP GKAPKLLIYW STNLYSGVPS    60
RFSGSGSGTD FTLTISSLQP EDFATYYCQQ IMSPPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 129          moltype = AA   length = 622
FEATURE                 Location/Qualifiers
REGION                  1..622
                        note = Synthetic polypeptide
source                  1..622
                        mol_type = protein
                        organism = synthetic construct
SEQUENCE: 129
EVQLVESGGG LVQPGGSLRL SCAASGFTID NTYIHWVRQA PGKGLEWVAR IDPVSGRTRY    60
ADSVKGRFTI SADTSKNTAD LQMNSLRAED TAVYYCARAF SWFPDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYASTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKLGG GGSGGGGSGG GGSPGQGTQS ENSCTHFPGN   480
LPNMLRDLRD AFSRVKTFFQ MKDQLDNLLL KESLLEDFKG YLGCQALSEM IQFYLEEVMP   540
QAENQDPDIK AHVNSLGENL KTLRLRLRRC HRFLPCENKS KAVEQVKNAF NKLQEKGIYK   600
AMSEFDIFIN YIEAYMTMKI RN                                           622

SEQ ID NO: 130          moltype = AA   length = 214
FEATURE                 Location/Qualifiers
REGION                  1..214
                        note = Synthetic polypeptide
source                  1..214
                        mol_type = protein
                        organism = synthetic construct
SEQUENCE: 130
DIQMTQSPSS LSASVGDRVT ITCRAGQDVY KAVAWYQQKP GKAPKLLIYW STNLYSGVPS    60
RFSGSGSGTD FTLTISSLQP EDFATYYCQQ FGATPITFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 131          moltype = AA   length = 622
FEATURE                 Location/Qualifiers
REGION                  1..622
                        note = Synthetic polypeptide
source                  1..622
                        mol_type = protein
                        organism = synthetic construct
SEQUENCE: 131
EVQLVESGGG LVQPGGSLRL SCAASGFTIS DAYIHWVRQA PGKGLEWVAR IEPLSGRTDY    60
ADSVKGRFTI SADTSKNTAY LQMNSLRAED TAVYYCARAF SWFMDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYASTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKLGG GGSGGGGSGG GGSPGQGTQS ENSCTHFPGN   480
LPNMLRDLRD AFSRVKTFFQ MKDQLDNLLL KESLLEDFKG YLGCQALSEM IQFYLEEVMP   540
QAENQDPDIK AHVNSLGENL KTLRLRLRRC HRFLPCENKS KAVEQVKNAF NKLQEKGIYK   600
AMSEFDIFIN YIEAYMTMKI RN                                           622

SEQ ID NO: 132          moltype = AA   length = 214
FEATURE                 Location/Qualifiers
REGION                  1..214
                        note = Synthetic polypeptide
source                  1..214
                        mol_type = protein
                        organism = synthetic construct
```

```
SEQUENCE: 132
DIQMTQSPSS LSASVGDRVT ITCRAGQDVY KAVAWYQQKP GKAPKLLIYW STNLYSGVPS    60
RFSGSGSGTD FTLMISSLQP EDFATYYCQQ HDKTPTTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 133           moltype = AA  length = 622
FEATURE                  Location/Qualifiers
REGION                   1..622
                         note = Synthetic polypeptide
source                   1..622
                         mol_type = protein
                         organism = synthetic construct
SEQUENCE: 133
EVQLVESGGG LVQPGGSLRL SCAASGFTIE DSYIHWVRQA PGKGLEWVAR IDPITGLTHY    60
ADSVKGRFTI SADTSKNTAY LQMNSLRAED TAVYYCARAF SWFPDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYASTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKLGG GGSGGGGSGG GGSPGQGTQS ENSCTHFPGN   480
LPNMLRDLRD AFSRVKTFFQ MKDQLDNLLL KESLLEDFKG YLGCQALSEM IQFYLEEVMP   540
QAENQDPDIK AHVNSLGENL KTLRLRLRRC HRFLPCENKS KAVEQVKNAF NKLQEKGIYK   600
AMSEFDIFIN YIEAYMTMKI RN                                            622

SEQ ID NO: 134           moltype = AA  length = 214
FEATURE                  Location/Qualifiers
REGION                   1..214
                         note = Synthetic polypeptide
source                   1..214
                         mol_type = protein
                         organism = synthetic construct
SEQUENCE: 134
DIQMTQSPSS LSASVGDRVT ITCRAGQDVY KAVAWYQQKP GKAPKLLIYW STNLYSGVPS    60
RFSGSGSGTD FTLTISSLQP EDFATYYCQQ IMEPPVTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 135           moltype = AA  length = 596
FEATURE                  Location/Qualifiers
REGION                   1..596
                         note = Synthetic polypeptide
source                   1..596
                         mol_type = protein
                         organism = synthetic construct
SEQUENCE: 135
EVQLVESGGG LVQPGGSLRL SCAASGFTID NTYIHWVRQA PGKGLEWVAR IDPANGKTTY    60
ADSVKGRFTI SADTSKNTAN LQMNSLRAED TAVYYCARSF SWWADYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYASTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKLGG GGSGGGGSGG GGSPGQGTQS ENSCTHFPGN   480
LPNMLRDLRD AFSRVKTFFQ MKDQLDNLLL KESLLEDFKG YLGCQALSEM IQFYLEEVMP   540
QAENQDPDIK AHVNSLGENL KTLRLRLRRC HRFLPCENKS KAVEQVKNAF NKLQEK      596

SEQ ID NO: 136           moltype = AA  length = 214
FEATURE                  Location/Qualifiers
REGION                   1..214
                         note = Synthetic polypeptide
source                   1..214
                         mol_type = protein
                         organism = synthetic construct
SEQUENCE: 136
DIQMTQSPSS LSASVGDRVT ITCRAGQDVY KAVAWYQQKP GKAPKLLIYW STNLYSGVPS    60
RFSGSGSGTD FTLTISSLQP EDFATYYCQQ FNLQPTTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 137           moltype = AA  length = 622
FEATURE                  Location/Qualifiers
REGION                   1..622
                         note = Synthetic polypeptide
source                   1..622
                         mol_type = protein
                         organism = synthetic construct
```

```
SEQUENCE: 137
EVQLVESGGG LVQPGGSLRL SCAASGFTID NTYIHWVRQA PGKRLEWVAR IDPANGVTRY    60
ADSVKGRFTI SADTSKNTAY LQMNSLRAED TAVYYCARAF SWFPDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYASTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKLGG GGSGGGGSGG GGSPGQGTQS ENSCTHFPGN   480
LPNMLRDLRD AFSRVKTFFQ MKDQLDNLLL KESLLEDFKG YLGCQALSEM IQFYLEEVMP   540
QAENQDPDIK AHVNSLGENL KTLRLRLRRC HRFLPCENKS KAVEQVKNAF NKLQEKGIYK   600
AMSEFDIFIN YIEAYMTMKI RN                                             622

SEQ ID NO: 138          moltype = AA   length = 214
FEATURE                 Location/Qualifiers
REGION                  1..214
                        note = Synthetic polypeptide
source                  1..214
                        mol_type = protein
                        organism = synthetic construct
SEQUENCE: 138
DIQMTQSPSS LSASVGDRVT ITCRAGQDVY KAVAWYQQKP GKAPKLLIYW STNLYSGVPS    60
RFSGSGSGTD FTLTISSLQP EDFATYYCQQ YGIAPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 139          moltype = AA   length = 622
FEATURE                 Location/Qualifiers
REGION                  1..622
                        note = Synthetic polypeptide
source                  1..622
                        mol_type = protein
                        organism = synthetic construct
SEQUENCE: 139
EVQLVESGGG LVQPGGSLRL SCAASGFTIT DGYIHWVRQA PGKGLEWVAR IDPYNGRTNY    60
ADSVKGRFTI SADTSKNTAY LQMNSLRAED TAVYYCARAF SWFPDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYASTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKLGG GGSGGGGSGG GGSPGQGTQS ENSCTHFPGN   480
LPNMLRDLRD AFSRVKTFFQ MKDQLDNLLL KESLLEDFKG YLGCQALSEM IQFYLEEVMP   540
QAENQDPDIK AHVNSLGENL KTLRLRLRRC HRFLPCENKS KAVEQVKNAF NKLQEKGIYK   600
AMSEFDIFIN YIEAYMTMKI RN                                             622

SEQ ID NO: 140          moltype = AA   length = 214
FEATURE                 Location/Qualifiers
REGION                  1..214
                        note = Synthetic polypeptide
source                  1..214
                        mol_type = protein
                        organism = synthetic construct
SEQUENCE: 140
DIQMTQSPSS LSASVGDRVT ITCRAGQDVY KAVAWYQQKP GKAPKLLIYW STNLYSGVPS    60
RFSGSGSGTD FTLTISSLQP EDFATYYCQQ HGNAPITFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 141          moltype = AA   length = 622
FEATURE                 Location/Qualifiers
REGION                  1..622
                        note = Synthetic polypeptide
source                  1..622
                        mol_type = protein
                        organism = synthetic construct
SEQUENCE: 141
EVQLVESGGG LVQPGGSLRL SCAASGFTID DTYIHWVRQA PGKGLEWVAR IDPANGMTRY    60
ADSVKGRFMI SADTSKNTAY LQMNSLRAED TAVYYCARAF SWFPDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYASTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKLGG GGSGGGGSGG GGSPGQGTQS ENSCTHFPGN   480
LPNMLRDLRD AFSRVKTFFQ MKDQLDNLLL KESLLEDFKG YLGCQALSEM IQFYLEEVMP   540
QAENQDPDIK AHVNSLGENL KTLRLRLRRC HRFLPCENKS KAVEQVKNAF NKLQEKGIYK   600
AMSEFDIFIN YIEAYMTMKI RN                                             622
```

```
SEQ ID NO: 142          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 142
DIQMTQSPSS LSASVGDRVT ITCRAGQDVY KAVAWYQQKP GKAPKLLIYW STNLYSGVPS   60
RFSGSGSGTD FTLTISSLQP EDFATYYCQQ GSTWPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 143          moltype = AA  length = 448
FEATURE                 Location/Qualifiers
REGION                  1..448
                        note = Synthetic polypeptide
source                  1..448
                        mol_type = protein
                        organism = synthetic construct
SEQUENCE: 143
EVQLVESGGG LVQPGGSLRL SCAASGFTFS DSWIHWVRQA PGKGLEWVAW ISPYGGSTYY   60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 144          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 144
DIQMTQSPSS LSASVGDRVT ITCRASQDVS TAVAWQQKPG KAPKLLIYSA SFLYSGVPSR   60
FSGSGSGTDF TLTISSLQPE DFATYYCQQY LYHPATFGQG TKVEIKRRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 145          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 145
EVQLLESGGG LVQPGGSLRL SCAASGFTFS SYIMMWVRQA PGKGLEWVSS IYPSGGITFY   60
ADTVKGRFTI SRDNSKNTLY LQMNSLRAED TAVYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 146          moltype = AA  length = 216
FEATURE                 Location/Qualifiers
REGION                  1..216
                        note = Synthetic polypeptide
source                  1..216
                        mol_type = protein
                        organism = synthetic construct
SEQUENCE: 146
QSALTQPASV SGSPGQSITI SCTGTSSDVG GYNYVSWYQQ HPGKAPKLMI YDVSNRPSGV   60
SNRFSGSKSG NTASLTISGL QAEDEADYYC SSYTSSSTRV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                           216
```

```
SEQ ID NO: 147         moltype = AA   length = 450
FEATURE                Location/Qualifiers
REGION                 1..450
                       note = Synthetic polypeptide
source                 1..450
                       mol_type = protein
                       organism = synthetic construct
SEQUENCE: 147
EVQLVESGGG LVQPGGSLRL SCAASGFTFS RYWMSWVRQA PGKGLEWVAN IKQDGSEKYY    60
VDSVKGRFTI SRDNAKNSLY LQMNSLRAED TAVYYCAREG GWFGELAFDY WGQGTLVTVS   120
SASTKGPSVF PLAPSSKSTS GGTAALGCLV KDYFPPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYA   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 148         moltype = AA   length = 215
FEATURE                Location/Qualifiers
REGION                 1..215
                       note = Synthetic polypeptide
source                 1..215
                       mol_type = protein
                       organism = synthetic construct
SEQUENCE: 148
EIVLTQSPGT LSLSPGERAT LSCRASQRVS SSYLAWYQQK PGQAPRLLIY DASSRATGIP    60
DRFSGSGSGT DFTLTISRLE PEDFAWYYCQ QYGSLPWTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 149         moltype = AA   length = 447
FEATURE                Location/Qualifiers
REGION                 1..447
                       note = Synthetic polypeptide
source                 1..447
                       mol_type = protein
                       organism = synthetic construct
SEQUENCE: 149
EVQLVESGGG LVQPGGSLRL SCAASGFTIT DSFIHWVRQA PGKGLEWVAR IDPYGGTTNY    60
ADSVKGRFTI SADTSKNTAY LQMNSLRAED TAVYYCARAY SWFSDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYASTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 150         moltype = AA   length = 448
FEATURE                Location/Qualifiers
REGION                 1..448
                       note = Synthetic polypeptide
source                 1..448
                       mol_type = protein
                       organism = synthetic construct
SEQUENCE: 150
EVQLVESGGG LVQPGGSLRL SCAASGFTIS DFGIHWVRQA PGKGLEWVAG ISPDSGNTNY    60
ADSVKGRFTI SADTSKNTAY LQMNSLRAED TAVYFCARTF FRRSLDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYAST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                      448

SEQ ID NO: 151         moltype = AA   length = 214
FEATURE                Location/Qualifiers
REGION                 1..214
                       note = Synthetic polypeptide
source                 1..214
                       mol_type = protein
                       organism = synthetic construct
SEQUENCE: 151
DIQMTQSPSS LSASVGDRVT ITCRASQDVS SGVAWYQQKP GKAPKLLISF ANYLSGVPS     60
RFSGSGSGTD FTLTISSLQP EDFATYYCQQ GSNLPFTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

```
SEQ ID NO: 152           moltype = AA  length = 448
FEATURE                  Location/Qualifiers
REGION                   1..448
                         note = Synthetic polypeptide
source                   1..448
                         mol_type = protein
                         organism = synthetic construct
SEQUENCE: 152
EVQLVESGGG LVQPGGSLRL SCAASGFTIS NSFIHWVRQA PGKGLEWVAD ISPYSGYTNY   60
ADSVKGRFTI SADTSKNTAY LQMNSLRAED TAVYYCARTP AWGYMDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 153           moltype = AA  length = 214
FEATURE                  Location/Qualifiers
REGION                   1..214
                         note = Synthetic polypeptide
source                   1..214
                         mol_type = protein
                         organism = synthetic construct
SEQUENCE: 153
DIQMTQSPSS LSASVGDRVT ITCRASQDVS SSVAWYQQKP GKAQKLLISW ATSLYSGVPS   60
RFSGSGSGTD FTLTISSLQP EDFATYYCQQ YNNFPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 154           moltype = AA  length = 447
FEATURE                  Location/Qualifiers
REGION                   1..447
                         note = Synthetic polypeptide
source                   1..447
                         mol_type = protein
                         organism = synthetic construct
SEQUENCE: 154
EVQLVESGGG LVQPGGSLRL SCAASGFTIS DGYIHWVRQA PGKGLEWVAR IDPLTGRTMY   60
ADSVKGRFTI SADTSKNTAY LQMNSLRAED TAVYYCARAF SWWPDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYASTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 155           moltype = AA  length = 447
FEATURE                  Location/Qualifiers
REGION                   1..447
                         note = Synthetic polypeptide
source                   1..447
                         mol_type = protein
                         organism = synthetic construct
SEQUENCE: 155
EVQLVESGGG LVQPGGSLRL SCAASGFTID NTYIHWVRQA PGKGLEWVAR IDPVSGRTRY   60
ADSVKGRFTI SADTSKNTAD LQMNSLRAED TAVYYCARAF SWFPDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYASTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 156           moltype = AA  length = 447
FEATURE                  Location/Qualifiers
REGION                   1..447
                         note = Synthetic polypeptide
source                   1..447
                         mol_type = protein
                         organism = synthetic construct
SEQUENCE: 156
EVQLVESGGG LVQPGGSLRL SCAASGFTIS DAYIHWVRQA PGKGLEWVAR IEPLSGRTDY   60
ADSVKGRFTI SADTSKNTAY LQMNSLRAED TAVYYCARAF SWFMDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYASTY  300
RVVSVLTVLH QDWLNGKEYK CKVSNKALPA PIEKTISKAK GQPREPQVYT LPPSREEMTK  360
```

```
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 157          moltype = AA  length = 447
FEATURE                 Location/Qualifiers
REGION                  1..447
                        note = Synthetic polypeptide
source                  1..447
                        mol_type = protein
                        organism = synthetic construct
SEQUENCE: 157
EVQLVESGGG LVQPGGSLRL SCAASGFTIE DSYIHWVRQA PGKGLEWVAR IDPITGLTHY  60
ADSVKGRFTI SADTSKNTAY LQMNSLRAED TAVYYCARAF SWFPDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYASTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 158          moltype = AA  length = 447
FEATURE                 Location/Qualifiers
REGION                  1..447
                        note = Synthetic polypeptide
source                  1..447
                        mol_type = protein
                        organism = synthetic construct
SEQUENCE: 158
EVQLVESGGG LVQPGGSLRL SCAASGFTID NTYIHWVRQA PGKGLEWVAR IDPANGKTTY  60
ADSVKGRFTI SADTSKNTAN LQMNSLRAED TAVYYCARSF SWWADYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYASTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 159          moltype = AA  length = 447
FEATURE                 Location/Qualifiers
REGION                  1..447
                        note = Synthetic polypeptide
source                  1..447
                        mol_type = protein
                        organism = synthetic construct
SEQUENCE: 159
EVQLVESGGG LVQPGGSLRL SCAASGFTID NTYIHWVRQA PGKRLEWVAR IDPANGVTRY  60
ADSVKGRFTI SADTSKNTAY LQMNSLRAED TAVYYCARAF SWFPDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYASTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 160          moltype = AA  length = 447
FEATURE                 Location/Qualifiers
REGION                  1..447
                        note = Synthetic polypeptide
source                  1..447
                        mol_type = protein
                        organism = synthetic construct
SEQUENCE: 160
EVQLVESGGG LVQPGGSLRL SCAASGFTIT DGYIHWVRQA PGKGLEWVAR IDPYNGRTNY  60
ADSVKGRFTI SADTSKNTAY LQMNSLRAED TAVYYCARAF SWFPDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYASTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 161          moltype = AA  length = 447
FEATURE                 Location/Qualifiers
REGION                  1..447
                        note = Synthetic polypeptide
source                  1..447
                        mol_type = protein
                        organism = synthetic construct
```

```
SEQUENCE: 161
EVQLVESGGG LVQPGGSLRL SCAASGFTID DTYIHWVRQA PGKGLEWVAR IDPANGMTRY    60
ADSVKGRFMI SADTSKNTAY LQMNSLRAED TAVYYCARAF SWFPDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYASTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 162             moltype = DNA  length = 741
FEATURE                    Location/Qualifiers
misc_feature               1..741
                           note = Synthetic polynucleotide
source                     1..741
                           mol_type = other DNA
                           organism = synthetic construct
SEQUENCE: 162
atggccgata ttcaaatgac ccagagcccg agcagcctga gcgcgagcgt gggagatcgc    60
gtgaccatta cctgccgtgc gggccaggat gtttacaaag ctgtcgcatg gtatcagcag   120
aaaccaggca aagcgccgaa acttctgata tactggtcca ctaacctgta tagcggcgtg   180
ccgtcgcgtt tttcgggcag tggcagcggc acggacttta ccctgacgat atcttcctta   240
caaccggagg attttgcgac ctactactgt caacagggct ccacttggcc gttgaccttc   300
ggtcaaggca ccaaagtgga aatcaaacgt ggtggttctt ctagatcttc ctcctctggt   360
ggcggtggct cgggcggtgg tggggagtg cagctggtgg aatcgggagg cggtctggtg   420
caacctggcg gcagccttcg tctgagctgt gcggcgagcg gttccacat tactgattct   480
ttcattcatt gggtgcgtca agctcccggc aaggggctgg agtgggtcgc gaggattgat   540
ccctacggcg gtactacaaa ctatgccgac agcgtgaaag tcgctttac gattagtgat   600
gacaccagca aaaataccgc gtacctgcag atgaatagcc tgcgtgcgga agacacagcg   660
gtgtattatt gcgcgcgtgc gtactcttgg ttctccgatt attggggca gggcacccctt   720
gttaccgtga gctcggcgtc a                                             741

SEQ ID NO: 163             moltype = DNA  length = 744
FEATURE                    Location/Qualifiers
misc_feature               1..744
                           note = Synthetic polynucleotide
source                     1..744
                           mol_type = other DNA
                           organism = synthetic construct
SEQUENCE: 163
atggccgata ttcaaatgac ccagagcccg agcagcctga gcgcgagcgt gggagatcgc    60
gtgaccatta cctgccgtgc gagccaggat gttagtagtg gggtcgcatg gtatcagcag   120
aaaccaggca aagcgccgaa acttctgata tccttgcca attacctgta tagcggcgtg   180
ccgtcgcgtt tttcgggcag tggcagcggc acggacttta ccctgacgat atcttcctta   240
caaccggagg attttgcgac ctactactgt caacagggtt ccaacctccc gttcaccttc   300
ggtcaaggca ccaaagtgga aatcaaacgc ggtggttcct ctagatcttc cacctctggt   360
ggcggtggct cgggcggtgg tggggaagtg cagctggtgg aatcgggagg cggtctggtg   420
caacctggcg gcagccttcg tctgagctgt gcggcgagcg gttccacat tagcgatttt   480
gggattcatt gggtgcgtca agctcccggc aaggggctgg agtgggtcgc ggggatttcc   540
cccgacagtg gtaacacaaa ctatgccgac agcgtgaaag tcgctttac gattagtgcg   600
gacaccagca aaaataccgc gtacctgcag atgaatagcc tgcgtgcgga agacacagcg   660
gtgtatttt gcgcgcgtac tttttttagg cggagtctgg attattgggg cagggcacc   720
cttgttaccg tgagctcggc gtca                                          744

SEQ ID NO: 164             moltype = DNA  length = 744
FEATURE                    Location/Qualifiers
misc_feature               1..744
                           note = Synthetic polynucleotide
source                     1..744
                           mol_type = other DNA
                           organism = synthetic construct
SEQUENCE: 164
atggccgata ttcaaatgac ccagatcccg agcagcctga gcgcgagcgt gggagatcgc    60
gtgaccatta cctgccgtgc gagccaggat gttagcagtt ccgtcgcatg gtatcagcag   120
aaaccaggca aagcgcagaa acttctgata tcctgggcaa cttctctgta tagcggcgtg   180
ccgtcgcgtt tttcgggcag tggcagcggc acggacttta ccctgacgat atcttcctta   240
caaccggagg attttgcgac ctactactgt caacagtaca taactttcc gtacaccttc   300
ggtcaaggca ccaaagtgga aatcaaacgc ggtagttcct ctagatcttc ctcctctggt   360
ggcggtggct cgggcggtgg tggggaagtg cagctggtgg aatcgggagg cggtctggtg   420
caacctggcg gcagccttcg tctgagctgt gcggcgagcg gttccacat tagcaactct   480
tttattcatt gggtgcgtca agctcccggc aaggggctgg agtgggtcgc ggacatttct   540
ccctacagtg gttatacaaa ttatgccgac agcgtgaaag tcgctttac gattagtgcg   600
gacaccagca aaaataccgc gtacctgcag atgaatagcc tgcgtgcgga agacacagcg   660
gtgtattatt gcgcgcgtac tcctgcttgg gggtatatgg attattgggg cagggcacc   720
cttgttaccg tgagctcggc gtca                                          744
```

```
SEQ ID NO: 165           moltype = DNA   length = 741
FEATURE                  Location/Qualifiers
misc_feature             1..741
                         note = Synthetic polynucleotide
source                   1..741
                         mol_type = other DNA
                         organism = synthetic construct
SEQUENCE: 165
atggccgata ttcaaatgac ccagagcccg agcagcctga gcgcgagcgt gggagatcgc    60
gtgaccatta cctgccgtgc gggccaggat gtttacaaag ctgtcgcatg gtatcagcag   120
aaaccaggca aagcgccgaa acttctgata tactggtcca ctaacctgta tagcggcgtg   180
ccgtcgcgtt tttcgggcag tggcagcggc acggacttta ccctgacgat atcttcctta   240
caaccggagg attttgcgac ctactactgt caacagatta tgagtcctcc gcctaccttc   300
ggtcaaggca ccaaagtgga aatcaaacgt ggtggttcct ctagatcttc ctcctctggt   360
ggcggtggct cgggcggtgg tggggaagtg cagctggtgg aatcgggagg cggtctggtg   420
caacctggcg gcagccttcg tctgagctgt gcggcgagcg ggttcaccat ttctgatggg   480
tatattcatt gggtgcgtca agctcccggc aaggggctgg agtgggtcgc gaggattgat   540
cccttactg tcgtacaat gtatgccgac agcgtgaaag tcgctttac gattagtgcg       600
gacaccagca aaaataccgc gtacctgcag atgaatagcc tgcgtgcgga agacacagcg   660
gtgtattatt gcgcgcgtgc ttttcttgg tggcctgatt attgggggca gggcacccc     720
gttaccgtga gctcggcgtc a                                              741

SEQ ID NO: 166           moltype = DNA   length = 741
FEATURE                  Location/Qualifiers
misc_feature             1..741
                         note = Synthetic polynucleotide
source                   1..741
                         mol_type = other DNA
                         organism = synthetic construct
SEQUENCE: 166
atggccgata ttcaaatgac ccagagcccg agcagcctga gcgcgagcgt gggagatcgc    60
gtgaccatta cctgccgtgc gggccaggat gtttacaaag ctgtcgcatg gtatcagcag   120
aaaccaggca aagcgccgaa acttctgata tactggtcca ctaacctgta tagcggcgtg   180
ccgtcgcgtt tttcgggcag tggcagcggc acggacttta ccctgacgat atcttcctta   240
caaccggagg attttgcgac ctactactgt caacagtttg gggcgactcc gattaccttc   300
ggtcaaggca ccaaagtgga aatcaaacgt ggtggttccg ctagatcttc ctcctctggt   360
ggcggtggct cgggcggtgg tggggaagtg cagctggtgg aatcgggagg cggtctggtg   420
caacctggcg gcagccttcg tctgagctgt gcggcgagcg ggttcaccat tgataatact   480
tatattcatt gggtgcgtca agctcccggc aaggggctgg agtgggtcgc gaggattgat   540
cccgttagtg tcgtacacg ttatgccgac agcgtgaaag tcgctttac gattagtgcg      600
gacaccagca aaaataccgc ggacctgcag atgaatagcc tgcgtgcgga agacacagcg   660
gtgtattatt gcgcgcgtgc ttttagttgg tttccggatt attgggggca gggcacccct   720
gttaccgtga gctcggcgtc a                                              741

SEQ ID NO: 167           moltype = DNA   length = 741
FEATURE                  Location/Qualifiers
misc_feature             1..741
                         note = Synthetic polynucleotide
source                   1..741
                         mol_type = other DNA
                         organism = synthetic construct
SEQUENCE: 167
atggccgata ttcaaatgac ccagagcccg agcagcctga gcgcgagcgt gggagatcgc    60
gtgaccatta cctgccgtgc gggccaggat gtttacaaag ctgtcgcatg gtatcagcag   120
aaaccaggca aagcgccgaa acttctgata tactggtcca ctaacctgta tagcggcgtg   180
ccgtcgcgtt tttcgggcag tggcagcggc acggacttta ccctgatgat atcttcctta   240
caaccggagg attttgcgac ctactactgt caacagcatg ataagactcc gactaccttc   300
ggtcaaggca ccaaagtgga aatcaaacgt ggtggttccc ctagatcttc ctcctctggt   360
ggcggtggct cgggcggtgg tggggaagtg cagctggtgg aatcgggagg cggtctggtg   420
caacctggcg gcagccttcg tctgagctgt gcggcgagcg ggttcaccat ttctgatgct   480
tatattcatt gggtgcgtca ggctcccggg aaggggctgg agtgggtcgc gaggattgag   540
cccctgtctg tcgtacaga ttatgccgac agcgtgaaag tcgctttac gattagtgcg      600
gacaccagca aaaataccgc gtacctgcag atgaatagcc tgcgtgcgga agacacagcg   660
gtgtattatt gcgcgcgtgc ttttagttgg tttatggatt attgggggca gggcacccct   720
gttaccgtga gctcggcgtc a                                              741

SEQ ID NO: 168           moltype = DNA   length = 741
FEATURE                  Location/Qualifiers
misc_feature             1..741
                         note = Synthetic polynucleotide
source                   1..741
                         mol_type = other DNA
                         organism = synthetic construct
SEQUENCE: 168
atggccgata ttcaaatgac ccagagcccg agcagcctga gcgcgagcgt gggagatcgc    60
gtgaccatta cctgccgtgc gggccaggat gtttacaaag ctgtcgcatg gtatcagcag   120
aaaccaggta aagcgccgaa acttctgata tactggtcca ctaacctgta tagcggcgtg   180
ccgtcgcgtt tttcgggcag tggcagcggc acggacttta ccctgacgat atcttcctta   240
```

```
caaccggagg attttgcgac ctactactgt caacagatta tggagccgcc ggttaccttc    300
ggtcaaggca ccaaagtgga aatcaaacgt ggtggttccg ctagatcttc ctcctctggt    360
ggcggtggct cgggcggtgg tggggaagtg cagctggtgg aatcgggagg cggtctggtg    420
caacctggcg gcagccttcg tctgagctgt gcggcgagcg ggttcaccat tgaggattcg    480
tatattcatt gggtgcgtca agctcccggc aaggggctgg agtgggtcgc gaggattgat    540
cccattacgg gtttgacaca ttatgccgac agcgtgaaag gtcgctttac gattagtgcg    600
gacaccagca aaaataccgc gtacctgcag atgaatagcc tgcgtgcgga agacacagcg    660
gtgtattatt gcgcgcgtgc ttttagttgg tttccggatt attgggggca gggcacccttt    720
gttaccgtga gctcggcgtc a                                              741

SEQ ID NO: 169          moltype = DNA  length = 741
FEATURE                 Location/Qualifiers
misc_feature            1..741
                        note = Synthetic polynucleotide
source                  1..741
                        mol_type = other DNA
                        organism = synthetic construct
SEQUENCE: 169
atggccgata ttcaaatgac ccagagcccg agcagcctga gcgcgagcgt gggagatcgc     60
gtgaccatta cctgccgtgc gggccaggat gtttacaaag ctgtcgcatg gtatcagcag    120
aaaccaggca aagcgccgaa acttctgata tactggtcca ctaacctgta tagcggcgtg    180
ccgtcgcgtt tttcgggcag tggcagcggc acggacttta ccctgacgat atcttcctta    240
caaccggagg attttgcgac ctactactgt caacagttta atctgcagcc gactaccttc    300
ggtcaaggca ccaaagtgga aatcaaacgt ggtggttcct ctagatcttc ctcctctggt    360
ggcggtggct cgggcggtgg tggggaagtg cagctggtgg aatcgggagg cggtctggtg    420
caacctggcg gcagccttcg tctgagctgt gcggcgagcg ggttcaccat tgataatacg    480
tatattcatt gggtgcgtca agctcccggc aaggggctgg agtgggtcgc gaggattgat    540
cccgcgaatg gtaagacaac ttatgccgac agcgtgaaag gtcgctttac gattagtgcg    600
gacaccagca aaaataccgc gaacctgcag atgaatagcc tgcgtgcgga agacacagcg    660
gtgtattatt gcgcgcgttc ttttttcgtgg tgggctgatt attgggggca gggcacccttt   720
gttaccgtga gctcggcgtc a                                              741

SEQ ID NO: 170          moltype = DNA  length = 741
FEATURE                 Location/Qualifiers
misc_feature            1..741
                        note = Synthetic polynucleotide
source                  1..741
                        mol_type = other DNA
                        organism = synthetic construct
SEQUENCE: 170
atggccgata ttcaaatgac ccagagcccg agcagcctga gcgcgagcgt gggagatcgc     60
gtgaccatta cctgccgtgc gggccaggat gtttacaaag ctgtcgcatg gtatcagcag    120
aaaccaggca aagcgccgaa acttctgata tactggtcca ctaacctgta tagcggcgtg    180
ccgtcgcgtt tttcgggcag tggcagcggc acggacttta ccctgacgat atcttcctta    240
caaccggagg attttgcgac ctactactgt caacagtatg gtattgctcc gcctaccttc    300
ggtcaaggca ccaaagtgga aatcaaacgt ggtggttcct ctagatcttc ctcctctggt    360
ggcggtggct cgggcggtgg tggggaagtg cagctggtgg aatcgggagg cggtctggtg    420
caacctggcg gcagccttcg tctgagctgt gcggcgagcg ggttcaccat tgataatact    480
tatattcatt gggtgcgtca agctcccggc aagaggctgg agtgggtcgc gaggattgat    540
cccgctaatg gtgtgacacg ttatgccgac agcgtgaaag gtcgctttac gattagtgcg    600
gacaccagca aaaataccgc gtacctgcag atgaatagcc tgcgtgcgga agacacagcg    660
gtgtattatt gcgcgcgtgc ttttctttgg tttcctgatt attgggggca gggcacccttt    720
gttaccgtga gctcggcgtc a                                              741

SEQ ID NO: 171          moltype = DNA  length = 741
FEATURE                 Location/Qualifiers
misc_feature            1..741
                        note = Synthetic polynucleotide
source                  1..741
                        mol_type = other DNA
                        organism = synthetic construct
SEQUENCE: 171
atggccgata ttcaaatgac ccagagcccg agcagcctga gcgcgagcgt gggagatcgc     60
gtgaccatta cctgccgtgc gggccaggat gtttacaaag ctgtcgcatg gtatcagcag    120
aaaccaggca aagcgccgaa acttctgata tactggtcca ctaacctgta tagcggcgtg    180
ccgtcgcgtt tttcgggcag tggcagcggc acggacttta ccctgacgat atcttcctta    240
caaccggagg attttgcgac ctactactgt caacagcatg taatgctcc gattaccttc    300
ggtcaaggca ccaaagtgga aatcaaacgt ggtggttcct ctagatcttc ctcctctggt    360
ggcggtggct cgggcggtgg tggggaagtg cagctggtgg aatcgggagg cggtctggtg    420
caacctggcg gcagccttcg tctgagctgt gcggcgagcg ggttcaccat tactgatggt    480
tatattcatt gggtgcgtca agctcccggc aaggggctgg agtgggtcgc gaggattgat    540
cccctataatg gtcgtacaaa ttatgccgac agcgtgaaag gtcgctttac gattagtgcg    600
gacaccagca aaaataccgc gtacctgcag atgaatagcc tgcgtgcgga agacacagcg    660
gtgtattatt gcgcgcgtgc ttttctttgg tttcctgatt attgggggca gggcacccttt    720
gttaccgtga gctcggcgtc a                                              741
```

```
SEQ ID NO: 172          moltype = DNA  length = 741
FEATURE                 Location/Qualifiers
misc_feature            1..741
                        note = Synthetic polynucleotide
source                  1..741
                        mol_type = other DNA
                        organism = synthetic construct
SEQUENCE: 172
atggccgata ttcaaatgac ccagagcccg agcagcctga gcgcgagcgt gggagatcgc   60
gtgaccatta cctgccgtgc gggccaggat gtttacaaag ctgtcgcatg gtatcagcag  120
aaaccaggca aagcgccgaa acttctgata tactggtcca ctaacctgta tagcggcgtg  180
ccgtcgcgtt tttcgggcag tggcagcggc acggacttta ccctgacgat atcttcctta  240
caaccggagg attttgcgac ctactactgt caacaggcct ccacttggcc gttgaccttc  300
ggtcaaggca ccaaagtgga aatcaaacgc ggtggttcct ctagatcttc ctcctctggt  360
ggcggtggct cgggcggtgg tggggaagtg cagctggtgg aatcgggagg cggtctggtg  420
caacctggcg gcagccttcg tctgagctgt gcggcgagcg ggttcaccat tgatgatact  480
tatattcatt gggtgcgtca agctcccggc aaggggctga gtgggtcgc gaggattgat  540
cccgcgaatg gtatgacaag gtatgccgac agcgtgaagg gtcgctttat gattagtcgc  600
gacaccagca aaaataccgc gtacctgcag atgaatagcc tgcgtgcgga agacacagcg  660
gtgtattatt gcgcgcgtgc tttttcttgg tttcctgatt attgggggca gggcacccttt  720
gttaccgtga gctcggcgtc a                                            741

SEQ ID NO: 173          moltype = AA  length = 290
FEATURE                 Location/Qualifiers
source                  1..290
                        mol_type = protein
                        organism = Homo sapiens
SEQUENCE: 173
MRIFAVFIFM TYWHLLNAFT VTVPKDLYVV EYGSNMTIEC KFPVEKQLDL AALIVYWEME   60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET            290

SEQ ID NO: 174          moltype = AA  length = 221
FEATURE                 Location/Qualifiers
source                  1..221
                        mol_type = protein
                        organism = Homo sapiens
SEQUENCE: 174
FTVTVPKDLY VVEYGSNMTI ECKFPVEKQL DLAALIVYWE MEDKNIIQFV HGEEDLKVQH   60
SSYRQRARLL KDQLSLGNAA LQITDVKLQD AGVYRCMISY GGADYKRITV KVNAPYNKIN  120
QRILVVDPVT SEHELTCQAE GYPKAEVIWT SSDHQVLSGK TTTTNSKREE KLFNVTSTLR  180
INTTTNEIFY CTFRRLDPEE NHTAELVIPE LPLAHPPNER T                     221

SEQ ID NO: 175          moltype = AA  length = 143
FEATURE                 Location/Qualifiers
source                  1..143
                        mol_type = protein
                        organism = Homo sapiens
SEQUENCE: 175
LDSPDRPWNP PTFSPALLVV TEGDNATFTC SFSNTSESFV LNWYRMSPSN QTDKLAAFPE   60
DRSQPGQDCR FRVTQLPNGR DFHMSVVRAR RNDSGTYLCG AISLAPKAQI KESLRAELRV  120
TERRAEVPTA HPSPSPRPAG QFQ                                         143

SEQ ID NO: 176          moltype = AA  length = 239
FEATURE                 Location/Qualifiers
source                  1..239
                        mol_type = protein
                        organism = Macaca fascicularis
SEQUENCE: 176
MRIFAVFIFT IYWHLLNAFT VTVPKDLYVV EYGSNMTIEC KFPVEKQLDL TSLIVYWEME   60
DKNIIQFVHG EEDLKVQHSN YRQRAQLLKD QLSLGNAALR ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL LNVTSTLRIN TTANEIFYCI FRRLDPEENH TAELVIPELP LALPPNERT   239

SEQ ID NO: 177          moltype = DNA  length = 38
FEATURE                 Location/Qualifiers
misc_feature            1..38
                        note = Synthetic polynucleotide
source                  1..38
                        mol_type = other DNA
                        organism = synthetic construct
SEQUENCE: 177
aatcacgatg tgatattcaa atgcccaga gcccgagc                            38
```

| SEQ ID NO: 178 | moltype = DNA length = 33 |
|---|---|
| FEATURE | Location/Qualifiers |
| misc_feature | 1..33 |
| | note = Synthetic polynucleotide |
| source | 1..33 |
| | mol_type = other DNA |
| | organism = synthetic construct |
| SEQUENCE: 178 | |
| aatcgtacgt ttgatttcca ctttggtgcc ttg | 33 |

| SEQ ID NO: 179 | moltype = DNA length = 39 |
|---|---|
| FEATURE | Location/Qualifiers |
| misc_feature | 1..39 |
| | note = Synthetic polynucleotide |
| source | 1..39 |
| | mol_type = other DNA |
| | organism = synthetic construct |
| SEQUENCE: 179 | |
| aatacgcgtg tcctgtccga agtgcagctg gtggaatcg | 39 |

| SEQ ID NO: 180 | moltype = DNA length = 27 |
|---|---|
| FEATURE | Location/Qualifiers |
| misc_feature | 1..27 |
| | note = Synthetic polynucleotide |
| source | 1..27 |
| | mol_type = other DNA |
| | organism = synthetic construct |
| SEQUENCE: 180 | |
| aatgctagcc gagctcacgg taacaag | 27 |

ANTI-PD-L1 ANTIBODIES AND ANTI-PD-L1/IL10 FUSION PROTEINS

CROSS REFERENCE TO RELATED APPLICATIONS

This application is a continuation under 35 U.S.C. § 365 of International Application Number PCT/US2021/032268, filed May 13, 2021, which claims the benefit under 35 U.S.C. § 119(e) to U.S. Provisional Patent Application Ser. No. 63/024,855, filed on May 14, 2020, the entirety of each of which is incorporated herein by reference.

FIELD OF THE INVENTION

The present disclosure relates to antibodies and fusion proteins which bind to the PD-L1 protein and methods of using such antibodies and fusion proteins.

REFERENCE TO SEQUENCE LISTING

The official copy of the Sequence Listing is submitted concurrently with the specification as an XML formatted file via EFS-Web with a file name of "09793-006WO1_SeqList_ST26.xml", a creation date of Jul. 21, 2022, and a size of 254,888 bytes. The Sequence Listing filed via EFS-Web is part of the specification and is incorporated in its entirety by reference herein. This XML formatted Sequence Listing discloses the identical sequences disclosed in the ASCII formatted text file "09793-006WO1_SeqList_ST25.txt" that was filed in the parent PCT application on May 13, 2021.

BACKGROUND OF THE INVENTION

Cancers represent a large group of diseases that involve abnormal cell growth with the potential to invade or spread to other parts of the body and constitute a primary cause of death. Because cancer cells are transformed (carcinogenesis) from normal cells, the antigenic surface proteins and/or glycoproteins presented by cancer cells are identical to or are highly similar to antigens that are present on normal, non-tumor cells in the host organism. The host organism's immune system therefore can have difficulty detecting and distinguishing cancer cells from normal cells. Additionally, cancer cells can adopt another mechanism to avoid host immune system detection.

Programmed death-ligand 1 (PD-L1) is a transmembrane protein that binds to the inhibitory checkpoint molecule, PD1 and thereby suppresses the adaptive immune response during pregnancy, autoimmune disease, and other disease states, such as hepatitis. Additionally, PD-L1 is highly expressed in cancer tissue and its level of expression has been found to correlate strongly with tumor aggressiveness. The over-expression of PD-L1 and its binding to its receptor protein, PD1 is believed to be critical to the mechanism by which cancer cells avoid destruction by the immune system of the host organism.

Interleukin 10 or "IL10" (also known as cytokine synthesis inhibitory factor, CSIF, IL-10, IL10A, GVHDS, or TGIF) is a cytokine that has multiple effects in immunoregulation and inflammation. IL10 is known to downregulate the expression of Th1 cytokines, MHC class II antigens, and co-stimulatory molecules on macrophages. IL10 is also known to enhance B cell survival, proliferation, and antibody production. IL10 can block NF-κB activity, and is involved in the regulation of the JAK-STAT signaling pathway. IL10 is capable of inhibiting synthesis of pro-inflammatory cytokines such as IFN-γ, IL-2, IL-3, TNFα and GM-CSF made by cells such as macrophages and Th1 T cells. It also displays a potent ability to suppress the antigen-presentation capacity of antigen presenting cells; however, it is also stimulatory towards certain T cells (Th2) and mast cells and stimulates B cell maturation and antibody production.

IL10 has been recognized as a potential inhibitor of tumor metastasis and an immunostimulatory agent useful in immuno-oncology treatments. In transgenic mice expression of IL10 or dosing with IL10 have been observed to control of primary tumor growth and decrease metastatic burden. A PEGylated version of recombinant murine IL10 has been shown to induce IFNγ and CD8+ T cell dependent anti-tumor immunity in mouse models. PEGylated recombinant human IL10 has been shown to enhance CD8+ T cell secretion of the cytotoxic molecules Granzyme B and Perforin and potentiate T cell receptor dependent IFNγ secretion. In clinical trials the PEGylated recombinant human IL10 (PEG-rHuIL-10, AM0010) has been found to exhibit substantial anti-tumor efficacy, eliciting a dose titratable induction of the immune stimulatory cytokines IFNγ, IL-18, IL-7, GM-CSF, and IL-4. Treated patients also exhibited an increase of peripheral CD8+ T cells expressing markers of activation, such as PD1, lymphocyte activation gene 3 (LAG3)+ and increased Fas Ligand (FasL), and a decrease in serum TGFβ. These findings suggest that IL10 treatment results in a predominantly immunostimulatory effect in humans.

SUMMARY OF THE INVENTION

The present disclosure provides anti-PD-L1 antibodies that specifically bind human PD-L1 with high affinity. The antibodies are capable of decreasing, inhibiting, and/or fully-blocking immune regulatory effects mediated by PD-L1 binding to the immune checkpoint molecule PD1. The present disclosure also provides fusions of an anti-PD-L1 antibody with one or two IL10 polypeptides. These anti-PD-L1/IL10 fusion proteins of the present disclosure are capable of providing a combined therapeutic effect of blocking immune regulatory effects mediated by PD-L1 binding to PD1 and providing immunostimulatory effects mediated by IL10.

In at least one embodiment, the present disclosure provides an anti-PD-L1 antibody comprising (i) a first light chain complementary determining region (CDR-L1), a second light chain complementary determining region (CDR-L2), and a third light chain complementary determining region (CDR-L3), and/or (ii) a first heavy chain complementary determining region (CDR-H1), a second heavy chain complementary determining region (CDR-H2), and a third heavy chain complementary determining region (CDR-H3), wherein:
  (a) CDR-H1 comprises an amino acid sequence selected from SEQ ID NO: 49, 57, 65, 87, 93, 99, 105, 119, and 124;
  (b) CDR-H2 comprises an amino acid sequence selected from SEQ ID NO: 50, 58, 66, 88, 94, 100, 106, 110, 115, 120, and 125;
  (c) CDR-H3 comprises an amino acid sequence selected from SEQ ID NO: 51, 59, 67, 89, 95, 101, and 111;
  (d) CDR-L1 comprises an amino acid sequence selected from SEQ ID NO: 53, 61, and 69;
  (e) CDR-L2 comprises an amino acid sequence selected from SEQ ID NO: 54, 62, and 70;

(f) CDR-L3 comprises an amino acid sequence selected from SEQ ID NO: 55, 63, 71, 91, 97, 103, 108, 113, 117, and 122.

In at least one embodiment, the present disclosure provides an anti-PD-L1 antibody wherein:
(a) CDR-H1 comprises the amino acid sequence of SEQ ID NO: 49, CDR-H2 comprises the amino acid sequence of SEQ ID NO: 50, and CDR-H3 comprises the amino acid sequence of SEQ ID NO: 51;
(b) CDR-H1 comprises the amino acid sequence of SEQ ID NO: 57, CDR-H2 comprises the amino acid sequence of SEQ ID NO: 58, and CDR-H3 comprises the amino acid sequence of SEQ ID NO: 59;
(c) CDR-H1 comprises the amino acid sequence of SEQ ID NO: 65, CDR-H2 comprises the amino acid sequence of SEQ ID NO: 66, and CDR-H3 comprises the amino acid sequence of SEQ ID NO: 67;
(d) CDR-H1 comprises the amino acid sequence of SEQ ID NO: 87, CDR-H2 comprises the amino acid sequence of SEQ ID NO: 88, and CDR-H3 comprises the amino acid sequence of SEQ ID NO: 89;
(e) CDR-H1 comprises the amino acid sequence of SEQ ID NO: 93, CDR-H2 comprises the amino acid sequence of SEQ ID NO: 94, and CDR-H3 comprises the amino acid sequence of SEQ ID NO: 95;
(f) CDR-H1 comprises the amino acid sequence of SEQ ID NO: 99, CDR-H2 comprises the amino acid sequence of SEQ ID NO: 100, and CDR-H3 comprises the amino acid sequence of SEQ ID NO: 101;
(g) CDR-H1 comprises the amino acid sequence of SEQ ID NO: 105, CDR-H2 comprises the amino acid sequence of SEQ ID NO: 106, and CDR-H3 comprises the amino acid sequence of SEQ ID NO: 95;
(h) CDR-H1 comprises the amino acid sequence of SEQ ID NO: 93, CDR-H2 comprises the amino acid sequence of SEQ ID NO: 110, and CDR-H3 comprises the amino acid sequence of SEQ ID NO: 111;
(i) CDR-H1 comprises the amino acid sequence of SEQ ID NO: 93, CDR-H2 comprises the amino acid sequence of SEQ ID NO: 115, and CDR-H3 comprises the amino acid sequence of SEQ ID NO: 95;
(j) CDR-H1 comprises the amino acid sequence of SEQ ID NO: 119, CDR-H2 comprises the amino acid sequence of SEQ ID NO: 120, and CDR-H3 comprises the amino acid sequence of SEQ ID NO: 95; or
(k) CDR-H1 comprises the amino acid sequence of SEQ ID NO: 124, CDR-H2 comprises the amino acid sequence of SEQ ID NO: 125, and CDR-H3 comprises the amino acid sequence of SEQ ID NO: 95.

In at least one embodiment, the present disclosure provides an anti-PD-L1 antibody wherein:
(a) CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 55;
(b) CDR-L1 comprises the amino acid sequence of SEQ ID NO: 61, CDR-L2 comprises the amino acid sequence of SEQ ID NO: 62, and CDR-L3 comprises the amino acid sequence of SEQ ID NO: 63;
(c) CDR-L1 comprises the amino acid sequence of SEQ ID NO: 69, CDR-L2 comprises the amino acid sequence of SEQ ID NO: 70, and CDR-L3 comprises the amino acid sequence of SEQ ID NO: 71;
(d) CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 91;
(e) CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 97;
(f) CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 103;
(g) CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 108;
(h) CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 113;
(i) CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 117; or
(j) CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 122.

In at least one embodiment, the present disclosure provides an anti-PD-L1 antibody wherein:
(a) CDR-H1 comprises the amino acid sequence of SEQ ID NO: 49, CDR-H2 comprises the amino acid sequence of SEQ ID NO: 50, CDR-H3 comprises the amino acid sequence of SEQ ID NO: 51, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 55;
(b) CDR-H1 comprises the amino acid sequence of SEQ ID NO: 57, CDR-H2 comprises the amino acid sequence of SEQ ID NO: 58, CDR-H3 comprises the amino acid sequence of SEQ ID NO: 59, CDR-L1 comprises the amino acid sequence of SEQ ID NO: 61, CDR-L2 comprises the amino acid sequence of SEQ ID NO: 62, and CDR-L3 comprises the amino acid sequence of SEQ ID NO: 63;
(c) CDR-H1 comprises the amino acid sequence of SEQ ID NO: 65, CDR-H2 comprises the amino acid sequence of SEQ ID NO: 66, CDR-H3 comprises the amino acid sequence of SEQ ID NO: 67, CDR-L1 comprises the amino acid sequence of SEQ ID NO: 69, CDR-L2 comprises the amino acid sequence of SEQ ID NO: 70, and CDR-L3 comprises the amino acid sequence of SEQ ID NO: 71;
(d) CDR-H1 comprises the amino acid sequence of SEQ ID NO: 87, CDR-H2 comprises the amino acid sequence of SEQ ID NO: 88, CDR-H3 comprises the amino acid sequence of SEQ ID NO: 89, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 91;
(e) CDR-H1 comprises the amino acid sequence of SEQ ID NO: 93, CDR-H2 comprises the amino acid sequence of SEQ ID NO: 94, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 97;

(f) CDR-H1 comprises the amino acid sequence of SEQ ID NO: 99, CDR-H2 comprises the amino acid sequence of SEQ ID NO: 100, CDR-H3 comprises the amino acid sequence of SEQ ID NO: 101, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 103;

(g) CDR-H1 comprises the amino acid sequence of SEQ ID NO: 105, CDR-H2 comprises the amino acid sequence of SEQ ID NO: 106, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 108;

(h) CDR-H1 comprises the amino acid sequence of SEQ ID NO: 93, CDR-H2 comprises the amino acid sequence of SEQ ID NO: 110, CDR-H3 comprises the amino acid sequence of SEQ ID NO: 111, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 113;

(i) CDR-H1 comprises the amino acid sequence of SEQ ID NO: 93, CDR-H2 comprises the amino acid sequence of SEQ ID NO: 115, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 117;

(j) CDR-H1 comprises the amino acid sequence of SEQ ID NO: 119, CDR-H2 comprises the amino acid sequence of SEQ ID NO: 120, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 122; or (k) CDR-H1 comprises the amino acid sequence of SEQ ID NO: 124, CDR-H2 comprises the amino acid sequence of SEQ ID NO: 125, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 55.

In at least one embodiment, the present disclosure provides an anti-PD-L1 antibody wherein the antibody comprises a heavy chain variable domain ($V_H$) amino acid sequence having at least 90% identity to a sequence selected from SEQ ID NO: 52, 60, 68, 90, 96, 102, 107, 112, 116, 121, and 126; and/or a light chain variable domain ($V_L$) amino acid sequence having at least 90% identity to a sequence selected from SEQ ID NO: 56, 64, 72, 92, 98, 104, 109, 114, 118, and 123; optionally, wherein:

(a) the antibody comprises a $V_H$ amino acid sequence having at least 90% identity to SEQ ID NO: 52; and/or a $V_L$ amino acid sequence having at least 90% identity to SEQ ID NO: 56;

(b) the antibody comprises a $V_H$ amino acid sequence having at least 90% identity to SEQ ID NO: 60; and/or a $V_L$ amino acid sequence having at least 90% identity to SEQ ID NO: 64;

(c) the antibody comprises a $V_H$ amino acid sequence having at least 90% identity to SEQ ID NO: 68; and/or a $V_L$ amino acid sequence having at least 90% identity to SEQ ID NO: 72;

(d) the antibody comprises a $V_H$ amino acid sequence having at least 90% identity to SEQ ID NO: 90; and/or a $V_L$ amino acid sequence having at least 90% identity to SEQ ID NO: 92;

(e) the antibody comprises a $V_H$ amino acid sequence having at least 90% identity to SEQ ID NO: 96; and/or a $V_L$ amino acid sequence having at least 90% identity to SEQ ID NO: 98;

(f) the antibody comprises a $V_H$ amino acid sequence having at least 90% identity to SEQ ID NO: 102; and/or a $V_L$ amino acid sequence having at least 90% identity to SEQ ID NO: 104;

(g) the antibody comprises a $V_H$ amino acid sequence having at least 90% identity to SEQ ID NO: 107; and/or a $V_L$ amino acid sequence having at least 90% identity to SEQ ID NO: 109;

(h) the antibody comprises a $V_H$ amino acid sequence having at least 90% identity to SEQ ID NO: 112; and/or a $V_L$ amino acid sequence having at least 90% identity to SEQ ID NO: 114;

(i) the antibody comprises a $V_H$ amino acid sequence having at least 90% identity to SEQ ID NO: 116; and/or a $V_L$ amino acid sequence having at least 90% identity to SEQ ID NO: 118;

(j) the antibody comprises a $V_H$ amino acid sequence having at least 90% identity to SEQ ID NO: 121; and/or a $V_L$ amino acid sequence having at least 90% identity to SEQ ID NO: 123; or (k) the antibody comprises a $V_H$ amino acid sequence having at least 90% identity to SEQ ID NO: 126; and/or a $V_L$ amino acid sequence having at least 90% identity to SEQ ID NO: 56.

In at least one embodiment, the present disclosure provides an anti-PD-L1 antibody wherein the antibody comprises a heavy chain (HC) amino acid sequence having at least 90% identity to a sequence selected from SEQ ID NO: 149, 150, 152, 154, 155, 156, 157, 158, 159, 160, and 161, and/or a light chain (LC) amino acid sequence having at least 90% identity to a sequence selected from SEQ ID NO: 128, 130, 132, 134, 136, 138, 140, 142, 151, and 153; optionally, wherein the antibody comprises:

(a) the HC amino acid sequence of SEQ ID NO: 149, and the LC amino acid sequence of SEQ ID NO: 142;

(b) the HC amino acid sequence of SEQ ID NO: 150, and LC amino acid sequence of SEQ ID NO: 151;

(c) the HC amino acid sequence of SEQ ID NO: 152, and the LC amino acid sequence of SEQ ID NO: 153;

(d) the HC amino acid sequence of SEQ ID NO: 154, and the LC amino acid sequence of SEQ ID NO: 128;

(e) the HC amino acid sequence of SEQ ID NO: 155, and the LC amino acid sequence of SEQ ID NO: 130;

(f) the HC amino acid sequence of SEQ ID NO: 156, and the LC amino acid sequence of SEQ ID NO: 132;

(g) the HC amino acid sequence of SEQ ID NO: 157, and the LC amino acid sequence of SEQ ID NO: 134;

(h) the HC amino acid sequence of SEQ ID NO: 158, and the LC amino acid sequence of SEQ ID NO: 136;

(i) the HC amino acid sequence of SEQ ID NO: 159, and the LC amino acid sequence of SEQ ID NO: 138;

(j) the HC amino acid sequence of SEQ ID NO: 160, and the LC amino acid sequence of SEQ ID NO: 140; or (k) the HC amino acid sequence of SEQ ID NO: 161, and the LC amino acid sequence of SEQ ID NO: 142.

In at least one embodiment, the present disclosure provides an anti-PD-L1 antibody wherein the antibody comprises a heavy chain (HC) fused via a linker to a cytokine selected from IL2, IL7, IL10, IL12, IL15, IL21, or IFN-α; optionally, wherein the linker comprises an amino acid sequence selected from SEQ ID NO: 74, 75, 76, 77, 78, and 79.

In at least one embodiment of the anti-PD-L1 antibody comprising a HC fused via a linker to a cytokine, the cytokine is IL10; optionally, wherein:
(a) the HC fused to the IL10 polypeptide comprises an HC-IL10 fusion amino acid sequence having at least 90% identity to a sequence selected from SEQ ID NO: 83, 84, 85, 127, 129, 131, 133, 135, 137, 139, and 141;
(b) the IL10 comprises an amino acid sequence of SEQ ID NO: 73; and/or
(c) the IL10 is a naturally-occurring or engineered variant of IL10 that retains its cytokine activity;
(d) the IL10 is a synthetically modified version of IL10 that retains its cytokine activity; and/or
(e) the IL10 comprises one, two, or four IL10 polypeptides.

In at least one embodiment, the present disclosure provides an anti-PD-L1 antibody comprising a HC fused via a linker to an IL10 polypeptide, wherein the antibody comprises (i) a first light chain complementary determining region (CDR-L1), a second light chain complementary determining region (CDR-L2), and a third light chain complementary determining region (CDR-L3), and (ii) a first heavy chain complementary determining region (CDR-H1), a second heavy chain complementary determining region (CDR-H2), and a third heavy chain complementary determining region (CDR-H3), wherein:
(a) CDR-H1 comprises the amino acid sequence of SEQ ID NO: 1, CDR-H2 comprises the amino acid sequence of SEQ ID NO: 2, CDR-H3 comprises the amino acid sequence of SEQ ID NO: 3, CDR-L1 comprises the amino acid sequence of SEQ ID NO: 5, CDR-L2 comprises the amino acid sequence of SEQ ID NO: 6, and CDR-L3 comprises the amino acid sequence of SEQ ID NO: 7;
(b) CDR-H1 comprises the amino acid sequence of SEQ ID NO: 9, CDR-H2 comprises the amino acid sequence of SEQ ID NO: 10, CDR-H3 comprises the amino acid sequence of SEQ ID NO: 11, CDR-L1 comprises the amino acid sequence of SEQ ID NO: 13, CDR-L2 comprises the amino acid sequence of SEQ ID NO: 14, and CDR-L3 comprises the amino acid sequence of SEQ ID NO: 15;
(c) CDR-H1 comprises the amino acid sequence of SEQ ID NO: 17, CDR-H2 comprises the amino acid sequence of SEQ ID NO: 18, CDR-H3 comprises the amino acid sequence of SEQ ID NO: 19, CDR-L1 comprises the amino acid sequence of SEQ ID NO: 21, CDR-L2 comprises the amino acid sequence of SEQ ID NO: 22, and CDR-L3 comprises the amino acid sequence of SEQ ID NO: 23;
(d) CDR-H1 comprises the amino acid sequence of SEQ ID NO: 25, CDR-H2 comprises the amino acid sequence of SEQ ID NO: 26, CDR-H3 comprises the amino acid sequence of SEQ ID NO: 27, CDR-L1 comprises the amino acid sequence of SEQ ID NO: 29, CDR-L2 comprises the amino acid sequence of SEQ ID NO: 30, and CDR-L3 comprises the amino acid sequence of SEQ ID NO: 31;
(e) CDR-H1 comprises the amino acid sequence of SEQ ID NO: 33, CDR-H2 comprises the amino acid sequence of SEQ ID NO: 34, CDR-H3 comprises the amino acid sequence of SEQ ID NO: 35, CDR-L1 comprises the amino acid sequence of SEQ ID NO: 37, CDR-L2 comprises the amino acid sequence of SEQ ID NO: 38, and CDR-L3 comprises the amino acid sequence of SEQ ID NO: 39;
(f) CDR-H1 comprises the amino acid sequence of SEQ ID NO: 41, CDR-H2 comprises the amino acid sequence of SEQ ID NO: 42, CDR-H3 comprises the amino acid sequence of SEQ ID NO: 43, CDR-L1 comprises the amino acid sequence of SEQ ID NO: 45, CDR-L2 comprises the amino acid sequence of SEQ ID NO: 46, and CDR-L3 comprises the amino acid sequence of SEQ ID NO: 47;
(g) CDR-H1 comprises the amino acid sequence of SEQ ID NO: 49, CDR-H2 comprises the amino acid sequence of SEQ ID NO: 50, CDR-H3 comprises the amino acid sequence of SEQ ID NO: 51, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 55;
(h) CDR-H1 comprises the amino acid sequence of SEQ ID NO: 57, CDR-H2 comprises the amino acid sequence of SEQ ID NO: 58, CDR-H3 comprises the amino acid sequence of SEQ ID NO: 59, CDR-L1 comprises the amino acid sequence of SEQ ID NO: 61, CDR-L2 comprises the amino acid sequence of SEQ ID NO: 62, and CDR-L3 comprises the amino acid sequence of SEQ ID NO: 63;
(i) CDR-H1 comprises the amino acid sequence of SEQ ID NO: 65, CDR-H2 comprises the amino acid sequence of SEQ ID NO: 66, CDR-H3 comprises the amino acid sequence of SEQ ID NO: 67, CDR-L1 comprises the amino acid sequence of SEQ ID NO: 69, CDR-L2 comprises the amino acid sequence of SEQ ID NO: 70, and CDR-L3 comprises the amino acid sequence of SEQ ID NO: 71;
(j) CDR-H1 comprises the amino acid sequence of SEQ ID NO: 87, CDR-H2 comprises the amino acid sequence of SEQ ID NO: 88, CDR-H3 comprises the amino acid sequence of SEQ ID NO: 89, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 91;
(k) CDR-H1 comprises the amino acid sequence of SEQ ID NO: 93, CDR-H2 comprises the amino acid sequence of SEQ ID NO: 94, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 97;
(l) CDR-H1 comprises the amino acid sequence of SEQ ID NO: 99, CDR-H2 comprises the amino acid sequence of SEQ ID NO: 100, CDR-H3 comprises the amino acid sequence of SEQ ID NO: 101, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 103;
(m) CDR-H1 comprises the amino acid sequence of SEQ ID NO: 105, CDR-H2 comprises the amino acid sequence of SEQ ID NO: 106, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 108;
(n) CDR-H1 comprises the amino acid sequence of SEQ ID NO: 93, CDR-H2 comprises the amino acid sequence of SEQ ID NO: 110, CDR-H3 comprises the amino acid sequence of SEQ ID NO: 111, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 113;
(o) CDR-H1 comprises the amino acid sequence of SEQ ID NO: 93, CDR-H2 comprises the amino acid sequence of SEQ ID NO: 115, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 117;
(p) CDR-H1 comprises the amino acid sequence of SEQ ID NO: 119, CDR-H2 comprises the amino acid sequence of SEQ ID NO: 120, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 122; or
(q) CDR-H1 comprises the amino acid sequence of SEQ ID NO: 124, CDR-H2 comprises the amino acid sequence of SEQ ID NO: 125, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 55.

In at least one embodiment, the present disclosure provides an anti-PD-L1 antibody comprising a HC fused via a linker to an IL10 polypeptide, wherein the antibody comprises a heavy chain variable domain ($V_H$) amino acid sequence having at least 90% identity to a sequence selected from SEQ ID NO: 4, 12, 20, 28, 36, 44, 52, 60, 68, 90, 96, 102, 107, 112, 116, 121, and 126; and/or a light chain variable domain ($V_L$) amino acid sequence having at least 90% identity to a sequence selected from SEQ ID NO: 8, 16, 24, 32, 40, 48, 56, 64, 72, 92, 98, 104, 109, 114, 118, and 123; optionally, wherein:
(a) the antibody comprises a $V_H$ amino acid sequence having at least 90% identity to SEQ ID NO: 4; and/or a $V_L$ amino acid sequence having at least 90% identity to SEQ ID NO: 8;
(b) the antibody comprises a $V_H$ amino acid sequence having at least 90% identity to SEQ ID NO: 12; and/or a $V_L$ amino acid sequence having at least 90% identity to SEQ ID NO: 16;
(c) the antibody comprises a $V_H$ amino acid sequence having at least 90% identity to SEQ ID NO: 20; and/or a $V_L$ amino acid sequence having at least 90% identity to SEQ ID NO: 24;
(d) the antibody comprises a $V_H$ amino acid sequence having at least 90% identity to SEQ ID NO: 28; and/or a $V_L$ amino acid sequence having at least 90% identity to SEQ ID NO: 32;
(e) the antibody comprises a $V_H$ amino acid sequence having at least 90% identity to SEQ ID NO: 36; and/or a $V_L$ amino acid sequence having at least 90% identity to SEQ ID NO: 40;
(f) the antibody comprises a $V_H$ amino acid sequence having at least 90% identity to SEQ ID NO: 44; and/or a $V_L$ amino acid sequence having at least 90% identity to SEQ ID NO: 48;
(g) the antibody comprises a $V_H$ amino acid sequence having at least 90% identity to SEQ ID NO: 52; and/or a $V_L$ amino acid sequence having at least 90% identity to SEQ ID NO: 56;
(h) the antibody comprises a $V_H$ amino acid sequence having at least 90% identity to SEQ ID NO: 60; and/or a $V_L$ amino acid sequence having at least 90% identity to SEQ ID NO: 64;
(i) the antibody comprises a $V_H$ amino acid sequence having at least 90% identity to SEQ ID NO: 68; and/or a $V_L$ amino acid sequence having at least 90% identity to SEQ ID NO: 72;
(j) the antibody comprises a $V_H$ amino acid sequence having at least 90% identity to SEQ ID NO: 90; and/or a $V_L$ amino acid sequence having at least 90% identity to SEQ ID NO: 92;
(k) the antibody comprises a $V_H$ amino acid sequence having at least 90% identity to SEQ ID NO: 96; and/or a $V_L$ amino acid sequence having at least 90% identity to SEQ ID NO: 98;
(l) the antibody comprises a $V_H$ amino acid sequence having at least 90% identity to SEQ ID NO: 102; and/or a $V_L$ amino acid sequence having at least 90% identity to SEQ ID NO: 104;
(m) the antibody comprises a $V_H$ amino acid sequence having at least 90% identity to SEQ ID NO: 107; and/or a $V_L$ amino acid sequence having at least 90% identity to SEQ ID NO: 109;
(n) the antibody comprises a $V_H$ amino acid sequence having at least 90% identity to SEQ ID NO: 112; and/or a $V_L$ amino acid sequence having at least 90% identity to SEQ ID NO: 114;
(o) the antibody comprises a $V_H$ amino acid sequence having at least 90% identity to SEQ ID NO: 116; and/or a $V_L$ amino acid sequence having at least 90% identity to SEQ ID NO: 118;
(p) the antibody comprises a $V_H$ amino acid sequence having at least 90% identity to SEQ ID NO: 121; and/or a $V_L$ amino acid sequence having at least 90% identity to SEQ ID NO: 123; or
(q) the antibody comprises a $V_H$ amino acid sequence having at least 90% identity to SEQ ID NO: 126; and/or a $V_L$ amino acid sequence having at least 90% identity to SEQ ID NO: 56.

In at least one embodiment, the present disclosure provides an anti-PD-L1 antibody comprising a HC fused via a linker to an IL10 polypeptide, wherein the antibody comprises a HC-IL10 fusion amino acid sequence having at least 90% identity to a sequence selected from SEQ ID NO: 80, 81, 82, 83, 84, 85, 127, 129, 131, 133, 135, 137, 139, and 141, and a light chain (LC) amino acid sequence having at least 90% identity to a sequence selected from SEQ ID NO: 128, 130, 132, 134, 136, 138, 140, 142, 144, 146, and 148; optionally, wherein
(a) the HC-IL10 fusion amino acid sequence of SEQ ID NO: 80, and the LC amino acid sequence of SEQ ID NO: 144;
(b) the HC-IL10 fusion amino acid sequence of SEQ ID NO: 81, and the LC amino acid sequence of SEQ ID NO: 146;
(c) the HC-IL10 fusion amino acid sequence of SEQ ID NO: 82, and LC amino acid sequence of SEQ ID NO: 148;

(d) the HC-IL10 fusion amino acid sequence of SEQ ID NO: 83, and the LC amino acid sequence of SEQ ID NO: 142;
(e) the HC-IL10 fusion amino acid sequence of SEQ ID NO: 84, and the LC amino acid sequence of SEQ ID NO: 151;
(f) the HC-IL10 fusion amino acid sequence of SEQ ID NO: 85, and LC amino acid sequence of SEQ ID NO: 153;
(g) the HC-IL10 fusion amino acid sequence of SEQ ID NO: 127, and the LC amino acid sequence of SEQ ID NO: 128;
(h) the HC-IL10 fusion amino acid sequence of SEQ ID NO: 129, and the LC amino acid sequence of SEQ ID NO: 130;
(i) the HC-IL10 fusion amino acid sequence of SEQ ID NO: 131, and the LC amino acid sequence of SEQ ID NO: 132;
(j) the HC-IL10 fusion amino acid sequence of SEQ ID NO: 133, and the LC amino acid sequence of SEQ ID NO: 134;
(k) the HC-IL10 fusion amino acid sequence of SEQ ID NO: 135, and the LC amino acid sequence of SEQ ID NO: 136;
(l) the HC-IL10 fusion amino acid sequence of SEQ ID NO: 137, and the LC amino acid sequence of SEQ ID NO: 138;
(m) the HC-IL10 fusion amino acid sequence of SEQ ID NO: 139, and the LC amino acid sequence of SEQ ID NO: 140; or
(n) the HC-IL10 fusion amino acid sequence of SEQ ID NO: 141, and the LC amino acid sequence of SEQ ID NO: 142.

In at least one embodiment, the present disclosure provides an anti-PD-L1 antibody wherein:
(a) the antibody binds to human PD-L1 with a binding affinity of $1 \times 10-8$ M or less, $1 \times 10-9$ M or less, $1 \times 10-10$ M or less; optionally, wherein the binding affinity is measured by equilibrium dissociation constant (KD) to a huPD-L1 polypeptide of SEQ ID NO: 174;
(b) the antibody binds to cynomolgus PD-L1 with a binding affinity of $1 \times 10-8$ M or less, $1 \times 10-9$ M or less, $1 \times 10-10$ M or less; optionally, wherein the binding affinity is measured by equilibrium dissociation constant (KD) to a cynoPD-L1 polypeptide of SEQ ID NO: 176;
(c) the protein increases MC/9 cell proliferation by at least 25%, at least 50%, at least 100%, at least 150%, at least 200% or more;
(d) the protein increases IFNγ and granzyme B production from activated CD8 T cells by at least 25%, at least 50%, at least 100%, or more; and/or
(e) the antibody decreases tumor volume in a syngeneic mouse tumor model measured at 28 days by at least 25%, at least 50%, at least 75%, or more, wherein the mouse tumor model is selected from: CT26 colon cancer, EMT6 breast cancer.

The present disclosure also provides embodiments of the anti-PD-L1 antibodies disclosed herein, including embodiments wherein: (i) the antibody is a human, humanized, or chimeric antibody; (ii) the antibody comprises a fusion to recombinant protein; optionally, a fusion to an IL10 polypeptide; (iii) the antibody is a full length antibody of class IgG, optionally, wherein the class IgG antibody has an isotype selected from IgG1, IgG2, IgG3, and IgG4; (iv) the antibody comprises an Fc region variant, optionally an Fc region variant that alters effector function and/or a variant that alters antibody half-life; (v) the antibody is an antibody fragment, optionally selected from the group consisting of F(ab')$_2$, Fab', Fab, Fv, single domain antibody (VHH), and scFv; (vi) the antibody comprises an immunoconjugate, optionally, wherein the immunoconjugate comprises a therapeutic agent for treatment of a PD-L1-mediated disease or condition; or (vii) the antibody is a multi-specific antibody, optionally a bispecific antibody.

In at least one embodiment the present disclosure provides an isolated polynucleotide or vector encoding an anti-PD-L1 antibody of the present disclosure. In at least one embodiment the present disclosure provides an isolated host cell comprising a polynucleotide or vector encoding an anti-PD-L1 antibody of the present disclosure. In at least one embodiment, the present disclosure also provides a method of producing an anti-PD-L1 antibody of present disclosure comprising culturing a host cell comprising a polynucleotide or vector encoding an anti-PD-L1 antibody so that an antibody is produced.

In at least one embodiment, the present disclosure provides a pharmaceutical composition comprising an anti-PD-L1 antibody of the present disclosure and a pharmaceutically acceptable carrier; optionally, wherein the composition further comprises an IL10 polypeptide, a chemotherapeutic agent, and/or an antibody comprising a specificity for an immune checkpoint molecule.

In at least one embodiment, the present disclosure provides a method of treating a PD-L1-mediated disease in a subject, the method comprising administering to the subject a therapeutically effective amount of an anti-PD-L1 antibody of the present disclosure, or administering to the subject a therapeutically effective amount of a pharmaceutical composition of the present disclosure; optionally, wherein the disease is cancer; optionally, wherein the cancer is selected from colon cancer, pancreatic cancer, ovarian cancer, liver cancer, renal cancer, breast cancer, lung cancer, gastric cancer, head and neck cancer, and oral cancer.

In at least one embodiment, the present disclosure provides a method for treating cancer in a subject, comprising administering to the subject a PD-L1 antagonist and an IL-10 agonist; optionally, wherein the PD-L1 antagonist comprises an anti-PD-L1 antibody, a shRNA, a siRNA, a miRNA, a small molecule inhibitor of PD-L1, or a combination thereof; optionally, wherein the IL-10 agonist is IL-10, an IL-10 receptor binding protein, or a combination thereof; optionally, wherein the PD-L1 antagonist is an anti-PD-L1 antibody of the present disclosure; optionally, wherein the PD-L1 antagonist and the IL10 agonist comprise an anti-PD-L1 antibody having a HC fused via a linker to an IL10 polypeptide; optionally, wherein the method further comprises administering to the subject a T cell therapy.

BRIEF DESCRIPTION OF THE FIGURES

FIG. 1A: SDS-PAGE image of Avelumab, Avelumab/IL10. FIG. 1B: SDS-PAGE image of Durvalumab and Durvalumab/IL-10. FIG. 1C: SDS-PAGE image of the anti-PD-L1 antibodies, PHS102, PHS206, PHS219, and the anti-PD-L1/IL10 fusions: PHS102/IL10, PHS206/IL10, and PHS219/IL10. N: non-reducing, R: reducing.

FIG. 2A: blocking the binding of PD1 to PD-L1 exhibited by the exemplary anti-PD-L1 antibodies, Atezolizumab, PHS102, PHS206, and PHS219. FIG. 2B: blocking the binding of PD1 to PD-L1 exhibited by the exemplary anti-PD-L1/IL10 fusions, Atezolizumab/IL10, PHS102/IL10, PHS206/IL10, and PHS219/IL10. FIG. 2C: blocking the binding of PD1 to PD-L1 exhibited by the exemplary anti-PD-L1/IL10 fusions, Avelumab/IL10, and Durvalumab/IL10.

FIG. 3A shows results for cells incubated with serial dilutions of anti-PD-L1 antibodies prepared as in Example 1. FIG. 3B shows results for cells incubated with serial dilutions of the corresponding anti-PD-L1/IL10 fusion proteins prepared as in Example 1. Cell surface binding was analyzed by flow cytometry and expressed as Geometric MFI.

FIG. 5A: CD4 T cells were co-cultured with allogeneic mature dendritic cells (DC) in the presence of anti-PD-L1 antibodies or IgG control at 0.67 µg/mL. FIG. 5B: CD4 T cells were co-cultured with allogeneic mature dendritic cells (DC) in the presence of various anti-PDL1/IL10 fusion proteins (or IL10-Fc control) at 0.2 µg/mL. After 2 days, supernatants were taken for analysis of IL-2 production by ELISA. Mean±SD is shown. *p<0.05, p<0.01, *p<0.001, ****p<0.0001.

DETAILED DESCRIPTION

Figure 1A:
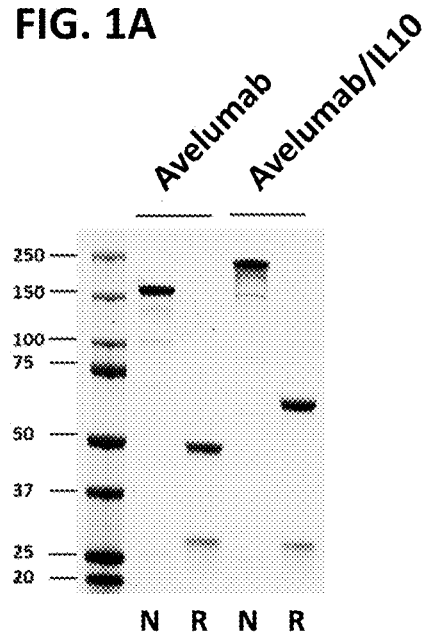
FIG. 1A, FIG. 1B, and FIG. 1C depict SDS-PAGE gel images of exemplary anti-PD-L1 antibodies in full-length IgG format, and anti-PD-L1/IL10 fusion proteins, that were generated, cloned, expressed, and purified as described in Example 1.

The present disclosure provides antibodies, including humanized antibodies, that specifically bind PD-L1 with high affinity and thereby inhibit, decrease, and/or fully block the function of PD-L1 as a protein ligand involved in immune regulation, particularly the function of PD-L1 as a ligand for the immune checkpoint molecule, PD1. It is believed that inhibition of the PD-L1/PD1 immune checkpoint signaling can potentiate an anti-tumor T-cell response. In clinical trials, anti-tumor effects in patients of PD-L1 inhibitors have been limited when administered as sole agents, and it is believed that there needs to be a combined use of these inhibitors with other anti-tumor therapeutic approaches. IL10 is a cytokine with anti-inflammatory and CD8+ T-cell activation properties. A strong IL-10 signal can promote tumor-specific CD8+ T-cell proliferation, revitalize exhausted T-cells, and thereby increase T-cell cytotoxicity. The present disclosure contemplates the use of anti-PD-L1 antibodies in combination with IL10 agonist, including as an anti-PD-L1 antibody fusion with human IL10 polypeptide. As disclosed herein, the combination PD-L1 inhibition, to reduce PD-L1/PD1 signaled immunosuppression, and a concentrated dose of IL10, to enhance CD8+ T-cell cytotoxicity in the TME, can provide an improved therapeutic approach to cancer treatment.

Accordingly, it is contemplated that any of the compositions or formulations comprising an anti-PD-L1 antibody of the present disclosure (including anti-PD-L1 antibodies fused to IL10 polypeptides) can be used as therapeutics for treatment of diseases mediated by the function of PD-L1 or its target receptor protein, PD1, such as cancer. Further, it is contemplated that the anti-PD-L1 antibodies of the present disclosure can be used as a therapeutic in combination with other therapeutics, such as antibodies that activate CD8+ T-cells, and/or other target immune checkpoint molecules including, but not limited to, PD1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, and ICOS.

Overview of Terminology and Techniques

For the descriptions herein and the appended claims, the singular forms "a", and "an" include plural referents unless the context clearly indicates otherwise. Thus, for example, reference to "a protein" includes more than one protein, and reference to "a compound" refers to more than one compound. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in Sambrook et al., *Molecular Cloning-A Laboratory Manual* (2nd Ed.), Vols. 1-3, Cold Spring Harbor Laboratory, Cold Spring Harbor, N.Y., 1989 (hereinafter "Sambrook"); *Current Protocols in Molecular Biology*, F. M. Ausubel et al., eds., Current Protocols, a joint venture between Greene Publishing Associates, Inc. and John Wiley & Sons, Inc. (supplemented through 2011) (hereinafter "Ausubel"); *Antibody Engineering*, Vols. 1 and 2, R. Kontermann and S. Dubel, eds., Springer-Verlag, Berlin and Heidelberg (2010); *Monoclonal Antibodies: Methods and Protocols*, V. Ossipow and N. Fischer, eds., 2nd Ed., Humana Press (2014); *Therapeutic Antibodies: From Bench to Clinic*, Z. An, ed., J. Wiley & Sons, Hoboken, N.J. (2009); and *Phage Display*, Tim Clackson and Henry B. Lowman, eds., Oxford University Press, United Kingdom (2004).

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for the purpose of describing particular embodiments only and is not intended to be limiting. For purposes of interpreting this disclosure, the following description of terms will apply and, where appropriate, a term used in the singular form will also include the plural form and vice versa.

"PD-L1" (or "PDL1"), as used herein, refers to the transmembrane protein, programmed death-ligand 1, and as used herein encompasses the PD-L1 proteins of human, cynomolgus monkey, mouse, and any isoforms of these proteins Amino acid sequences of various exemplary PD-L1 proteins are known in the art and are provided in Table 1 below and the attached Sequence Listing.

"PD-L1 mediated condition" or "PD-L1 mediated disease," as used herein, encompasses any medical condition associated with the specific binding of PD-L1 to the receptor and immune checkpoint molecule, PD1 (or "PD-1"). For example, specific binding of PD-L1 to PD1 on T-cells acts to inhibit their activation as part of an immune response. Accordingly, PD-L1 mediated diseases can include, but are not limited to, any disease or condition mediated by and/or responsive to antagonists or inhibitors of PD-L1, and/or PD1, including but not limited to cancers.

"IL10" or "IL-10," as used herein, refers to the cytokine, interleukin 10, also known as cytokine synthesis inhibitory factor (CSIF), and is intended to also include naturally-occurring variants, engineered variants, and/or synthetically modified versions of interleukin 10 that retain its cytokine functions Amino acid sequences of various exemplary IL10 polypeptides and recombinant IL10 fusion constructs are provided in Table 2 below and the attached Sequence Listing. Other exemplary engineered and/or modified IL10 polypeptides that retain cytokine functions are known in the art (see e.g., U.S. Pat. No. 7,749,490 B2; US 2017/0015747 A1; Naing, A. et al. "PEGylated IL-10 (Pegilodecakin) Induces Systemic Immune Activation, CD8+ T Cell Invigoration and Polyclonal T Cell Expansion in Cancer Patients." *Cancer Cell* 34, 775-791.e3 (2018); Gorby, C. et al. "Engineered IL-10 variants elicit potent immunomodulatory effects at low ligand doses." Sci Signal 13, (2020); Yoon, S. I. et al. "Epstein-Barr virus IL-10 engages IL-10R1 by a two-step mechanism leading to altered signaling properties." J Biol Chem 287, 26586-26595 (2012)).

"Fusion protein," as used herein, refers to two or more protein and/or polypeptide molecules that are linked (or "fused") in a configuration that does not occur naturally. An exemplary fusion protein of the present disclosure includes the "IL10-Fc" fusion protein that comprises an IL10 polypeptide covalently linked through a polypeptide linker sequence at its C-terminus to an immunoglobulin Fc region polypeptide. Fusion proteins of the present disclosure also include "antibody fusions" that comprise a full-length IgG antibody (with both a heavy chain and a light chain polypeptide) that is covalently linked through a polypeptide linker sequence at its heavy chain C-terminus to an IL10 polypeptide.

"Polypeptide linker" or "linker sequence" as used herein refers to a chain of two or more amino acids with each end of the chain covalently attached to a different polypeptide molecule, thereby functioning to conjugate or fuse the different polypeptides. Typically, polypeptide linkers comprise polypeptide chains of 5 to 30 amino acids. A wide range of polypeptide linkers are known in the art and can be used in the compositions and methods of the present disclosure. Exemplary polypeptide linkers include in the compositions and methods of the present disclosure include, (GGGGS)$_n$, (SSSSG)$_n$, (GGGG)(SGGGG)$_n$, (EAAAK)$_n$, (XP)$_n$, ENLYFQ(-G/S), typically, where n is 2 to 6, and other specific linker sequences as disclosed elsewhere herein.

"Antibody," as used herein, refers to a molecule comprising one or more polypeptide chains that specifically binds to, or is immunologically reactive with, a particular antigen. Exemplary antibodies of the present disclosure include monoclonal antibodies, polyclonal antibodies, chimeric antibodies, humanized antibodies, human antibodies, antibody fusions, multispecific antibodies (e.g., bispecific antibodies), monovalent antibodies (e.g., single-arm antibodies), multivalent antibodies, antigen-binding fragments (e.g., Fab', F(ab')$_2$, Fab, Fv, rIgG, and scFv fragments), and synthetic antibodies (or antibody mimetics).

"Anti-PD-L1 antibody" or "antibody that binds PD-L1" refers to an antibody that binds PD-L1 with sufficient affinity such that the antibody is useful as a therapeutic and/or diagnostic agent for targeting PD-L1. In some embodiments, the extent of binding of an anti-PD-L1 specific antibody to an unrelated, non-PD-L1 antigen is less than about 20%, less than about 15%, less than about 10%, or less than about 5% of the binding of the antibody to PD-L1 as measured by, e.g., radioimmunoassay (RIA) or surface plasmon resonance (SPR). In some embodiments, an anti-PD-L1 antibody of the present disclosure has a dissociation constant ($K_D$) of <1 µM, <100 nM, <10 nM, <1 nM, <0.1 nM, <0.01 nM, or <1 pM (e.g., $10^{-8}$ M or less, e.g., from $10^{-8}$ M to $10^{-13}$ M, e.g., from $10^{-9}$ M to $10^{-13}$ M).

"Full-length antibody," "intact antibody," or "whole antibody" are used herein interchangeably to refer to an antibody having a structure substantially similar to a native antibody structure or having heavy chains that contain an Fc region as defined herein.

"Antibody fusion" refers to an antibody that is covalently conjugated (or fused) to a polypeptide or protein, typically via a linker to a terminus of the antibody's light chain (LC) or heavy chain (HC). Exemplary antibody fusions of the present disclosure include an anti-PD-L1 antibody fused to a recombinant IL10 polypeptide via a 15 amino acid polypeptide linker (e.g., SEQ ID NO: 74) from the C-terminus of the antibody heavy chain to the N-terminus of the IL10 polypeptide. Antibody fusions are labeled herein with a "antibody/polypeptide" nomenclature to indicate the fusion components, such as "Ab/IL10" or "anti-PD-L1/IL10." As described elsewhere herein, an antibody fusion of the present disclosure can include a full-length IgG antibody, comprising a dimeric complex of heavy chain-light chain pairs, where each heavy chain C-terminus is linked through a polypeptide linker sequence to an IL10 polypeptide.

"Antibody fragment" refers to a portion of a full-length antibody which is capable of binding the same antigen as the full-length antibody. Examples of antibody fragments include, but are not limited to, Fv, Fab, Fab', Fab'-SH, F(ab')$_2$; diabodies; linear antibodies; monovalent, or single-armed antibodies; single-chain antibody molecules (e.g., scFv); and multispecific antibodies formed from antibody fragments.

"Class" of an antibody refers to the type of constant domain or constant region possessed by its heavy chain. There are five major classes of antibodies: IgA, IgD, IgE, IgG, and IgM, and several of these are further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and µ, respectively.

"Variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hypervariable regions (HVRs) (see, e.g., Kindt et al., Kuby Immunology, 6$^{th}$ ed., W.H. Freeman and Co., page 91). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (see, e.g., Portolano et al., J. Immunol. 150: 880-887 (1993); Clarkson et al., Nature 352:624-628 (1991)).

"Hypervariable region" or "HVR," as used herein, refers to each of the regions of an antibody variable domain which are hypervariable in sequence and/or form structurally defined loops ("hypervariable loops"). Generally, native antibodies comprise four chains with six HVRs; three in the heavy chain variable domain, $V_H$ (HVR-H1, HVR-H2, HVR-H3), and three in the light chain variable domain, $V_L$ (HVR-L1, HVR-L2, HVR-L3). The HVRs generally comprise amino acid residues from the hypervariable loops and/or from the "complementarity determining regions" (CDRs). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. "Contact" hypervariable regions are based on an analysis of the available complex crystal structures. Residue ranges for hypervariable regions defined under these systems are noted in the table below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B[1] | H26-H35B[1] | H26-H32[1] | H30-H35B[1] |
|  | H31-H35[2] | H26-H35[2] | H26-H32[2] | H30-H35[2] |

| Loop | Kabat[1] | AbM | Chothia[2] | Contact |
|------|----------|-----|---------|---------|
| H2 | H50-H65 | H50-H58 | H53-H55 | H47-H58 |
| H3 | H95-H102 | H95-H102 | H96-H101 | H93-H101 |

[1] Kabat numbering
[2] Chothia numbering

In addition to the systems described above, HVRs and CDRs can be identified using the international ImMunoGeneTics information system, referred to as IMGT/V-Quest, described in Brochet, X. et al., Nucl. Acids Res. 36, W503-508 (2008). PMID: 18503082; and available for use online at www.imgt.org/IMGT_vquest/input. IMGT/V-Quest analyzes alignments to closest germline V gene variable region nucleotide sequences using IMGT unique numbering to identify HVRs and CDRs.

Hypervariable regions (HVRs), as used herein, may include extended or alternative hypervariable regions as follows: 27-32, 27-36, 24-34, or 24-38 (HVR-L1); 50-52, 54-56, 50-56 or 54-60 (HVR-L2); 89-97 or 93-101 (HVR-L3); 26-33, 26-35, or 31-35 (HVR-H1); 51-58, 50-61, or 50-66 (H2); and 97-110, 97-112, 99-110, or 99-112 (H3) in the $V_H$ domain. The variable domain residues are numbered according to Kabat et al., supra, for each of these definitions.

"Complementarity determining region," or "CDR," as used herein, refers to the regions within the HVRs of the variable domain which have the highest sequence variability and/or are involved in antigen recognition. Generally, native antibodies comprise four chains with six CDRs; three in the heavy chain variable domains, $V_H$ (CDR-H1, CDR-H2, CDR-H3), and three in the light chain variable domains, $V_L$ (CDR-L1, CDR-L2, CDR-L3). Exemplary CDRs occur at variable domain amino acid residue positions: 24-34, 27-32, 27-36, 24-38 (CDR-L1); 50-56, 50-52, 54-56, or 54-60 (CDR-L2); 89-97, or 93-101 (CDR-L3); 31-35, or 26-33 (CDR-H1), 50-66, or 51-58 (CDR-H2); and 99-112, 99-110, 97-112, or 97-110 (CDR-H3).

"Framework" or "FR" refers to variable domain residues other than the HVR residues. The FRs of a variable domain generally consist of four domains: FR1, FR2, FR3, and FR4. Accordingly, the HVR and FR sequences generally appear in the following sequence in $V_H$ (or $V_L$): FR1-H1(L1)-FR2-H2(L2)-FR3-H3(L3)-FR4.

Unless otherwise indicated, the positions of residues in the HVRs, CDRs, FRs, and other residues in the variable domain are numbered herein according to Kabat et al., supra.

"Native antibody" refers to a naturally occurring immunoglobulin molecule. For example, native IgG antibodies are hetero-tetrameric glycoproteins of about 150,000 Daltons, composed of two identical light chains and two identical heavy chains that are disulfide-bonded. From N- to C-terminus, each heavy chain has a variable region ($V_H$), also called a variable heavy domain or a heavy chain variable domain, followed by three constant domains (CH1, CH2, and CH3) Similarly, from N- to C-terminus, each light chain has a variable region ($V_L$), also called a variable light domain or a light chain variable domain, followed by a constant light (CL) domain. The light chain of an antibody may be assigned to one of two types, called kappa (κ) and lambda (λ), based on the amino acid sequence of its constant domain.

"Monoclonal antibody" as used herein refers to an antibody obtained from a substantially homogeneous population of antibodies, i.e., the individual antibodies comprising the population are identical and/or bind the same epitope, except for possible variant antibodies (e.g., variant antibodies contain mutations that occur naturally or arise during production of a monoclonal antibody, and generally are present in minor amounts). In contrast to polyclonal antibody preparations, which typically include different antibodies directed against different determinants (epitopes), each monoclonal antibody of a monoclonal antibody preparation is directed against a single determinant on an antigen. Thus, the term "monoclonal" indicates the character of the antibody as being obtained from a substantially homogeneous population of antibodies and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Chimeric antibody" refers to an antibody in which a portion of the heavy and/or light chain is derived from a particular source or species, while the remainder of the heavy and/or light chain is derived from a different source or species.

"Humanized antibody" refers to a chimeric antibody comprising amino acid sequences from non-human HVRs and amino acid sequences from human FRs. In certain embodiments, a humanized antibody will comprise substantially all of at least one, and typically two, variable domains, in which all or substantially all of the HVRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

"Human antibody" refers to an antibody which possesses an amino acid sequence corresponding to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Human consensus framework" is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In one embodiment, for the $V_L$, the subgroup is subgroup kappa I as in Kabat et al., supra. In one embodiment, for the $V_H$, the subgroup is subgroup III as in Kabat et al., supra.

"Acceptor human framework" as used herein is a framework comprising the amino acid sequence of a light chain variable domain ($V_L$) framework or a heavy chain variable domain ($V_H$) framework derived from a human immunoglobulin framework or a human consensus framework. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Fc region," refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain may vary, the human IgG heavy chain Fc sequence is usually defined to stretch from an amino acid residue at about position Cys226, or from about position Pro230, to the carboxyl-terminus of the Fc sequence. However, the C-terminal lysine (Lys447) of the Fc sequence may or may not be present. The Fc sequence of an immunoglobulin generally comprises two constant domains, a CH2 domain and a CH3 domain, and optionally comprises a CH4 domain.

"Fc receptor" or "FcR," refers to a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see, e.g., Daeron, Annu. Rev. Immunol. 15:203-234 (1997)). FcR, as used herein, also includes the neonatal receptor, FcRn, which is responsible for the transfer of maternal IgGs to the fetus (Guyer et al, J. Immunol. 1 17:587 (1976) and Kim et al, J. Immunol. 24:249 (1994)) and regulation of homeostasis of immunoglobulins. FcRs are reviewed, for example, in Ravetch and Kinet, Annu. Rev. Immunol 9:457-92 (1991); Capel et al, Immunomethods 4:25-34 (1994); and de Haas et al, J. Lab. Clin. Med. 126:330-41 (1995).

"Multispecific antibody" is an antibody having at least two different binding sites, each site with a different binding specificity. A multispecific antibody can be a full length antibody or an antibody fragment, and the different binding sites may bind each to a different antigen or the different binding sites may bind to two different epitopes of the same antigen.

"Fv fragment" refers to an antibody fragment which contains a complete antigen recognition and binding site. This region consists of a dimer of one heavy and one light chain variable domain in tight association, which can be covalent in nature, for example in scFv. It is in this configuration that the three HVRs of each variable domain interact to define an antigen binding site on the surface of the $V_H$-$V_L$ dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

"Fab fragment' refers to an antibody fragment that contains a variable and constant domain of the light chain and a variable domain and the first constant domain (CH1) of the heavy chain. "F(ab')$_2$ fragments" comprise a pair of Fab fragments which are generally covalently linked near their carboxy termini by hinge cysteines between them. Other chemical couplings of antibody fragments also are known in the art.

"Antigen binding arm," as used herein, refers to a component of an antibody that has an ability to specifically bind a target molecule of interest. Typically, the antigen binding arm is a complex of immunoglobulin polypeptide sequences, e.g., HVR and/or variable domain sequences of an immunoglobulin light and heavy chain.

"Single-chain Fv" or "scFv" refer to antibody fragments comprising the $V_H$ and $V_L$ domains of an antibody, wherein these domains are present in a single polypeptide chain. Generally, an Fv polypeptide further comprises a polypeptide linker between the $V_H$ and $V_L$ domains which enables the scFv to form the desired antigen binding structure.

"Affinity" refers to the strength of the sum total of noncovalent interactions between a single binding site of a molecule (e.g., an antibody) and its binding partner (e.g., an antigen). "Binding affinity" refers to intrinsic binding affinity which reflects a 1:1 interaction between members of a binding pair (e.g., antibody and antigen). The affinity of a molecule X for its partner Y can generally be represented by the equilibrium dissociation constant ($K_D$). Affinity can be measured by common methods known in the art, including those described herein. Specific illustrative and exemplary embodiments for measuring binding affinity are described in the following.

"Binds specifically" or "specific binding" refers to binding of an antibody to an antigen with an affinity value of no more than about $1 \times 10^{-7}$ M. In some embodiments, an antibody may have a secondary affinity for an antigen other than the antigen to which it binds specifically, where "secondary affinity" will generally refer to binding of an antibody to a secondary antigen with an affinity value of more than about 10 nM as described elsewhere herein. Where an antibody may have a secondary affinity for a secondary antigen, such an antibody will nevertheless bind specifically to the primary antigen.

"Isolated antibody" refers to an antibody which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic methods (e.g., ion exchange or reverse phase HPLC). For review of methods for assessment of antibody purity, see, e.g., Flatman et al., J. Chromatogr. B 848:79-87.

"Effector function" refer to a biological activity attributed to the Fc region of an antibody, which varies with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

"Immunoconjugate" refers to an antibody conjugated to one or more heterologous molecule(s), including but not limited to a cytotoxic agent.

"Treatment," "treat" or "treating" refers to clinical intervention in an attempt to alter the natural course of a disorder in the individual being treated, and can be performed either for prophylaxis or during the course of clinical pathology. Desired results of treatment can include, but are not limited to, preventing occurrence or recurrence of the disorder, alleviation of symptoms, diminishment of any direct or indirect pathological consequences of the disorder, preventing metastasis, decreasing the rate of progression, amelioration or palliation of a disease state, and remission or improved prognosis. For example, treatment can include administration of a therapeutically effective amount of pharmaceutical formulation comprising an anti-PD-L1 antibody to a subject to delay development or slow progression of a disease or condition mediated by PD-L1 and/or its binding to PD1 or other ligands, or a disease or condition in which PD-L1 may play a role in the pathogenesis and/or progression.

"Pharmaceutical formulation" refers to a preparation in a form that allows the biological activity of the active ingredient(s) to be effective, and which contain no additional components which are toxic to the subjects to which the formulation is administered. A pharmaceutical formulation may include one or more active agents. For example, a pharmaceutical formulation may include an anti-PD-L1 antibody as the sole active agent of the formulation or may include an anti-PD-L1 antibody and one or more additional active agents, an immune activator such as IL10, or an inhibitor of an immune checkpoint molecule.

"Sole active agent," as used herein, refers an active agent in a pharmaceutical formulation that is the only active agent present in that formulation that provides, or would be expected to provide, the relevant pharmacological effect to treat the subject for the condition being treated. A pharmaceutical formulation comprising a sole active agent does not exclude the presence of one or more non-active agents, such as e.g., a pharmaceutically acceptable carrier, in the formulation. A "non-active agent" is an agent that would not be expected to provide, or otherwise significantly contribute to, the relevant pharmacological effect intended to treat the subject for the condition.

"Pharmaceutically acceptable carrier" refers to an ingredient in a pharmaceutical formulation, other than an active ingredient, which is nontoxic to the subject to whom it is administered. A pharmaceutically acceptable carrier includes, but is not limited to, a buffer, excipient, stabilizer, or preservative.

"Immune checkpoint molecule," as used herein, refers to a molecule that functions to regulate an immune system pathway and thereby prevent it from attacking cells unnecessarily. Many immune checkpoint molecules, both inhibitory and co-stimulatory, are targets for immunotherapy (e.g., with blocking antibodies to block immune inhibition or with agonists to promote immune stimulation) in the treatment of cancer and viral infections. Exemplary immune checkpoint molecules targeted for cancer immunotherapy include, but are not limited to, PD1, PD-L1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, ICOS.

"Therapeutically effective amount" refers to the amount of an active ingredient or agent (e.g., a pharmaceutical formulation) to achieve a desired therapeutic or prophylactic result, e.g., to treat or prevent a disease, disorder, or condition in a subject. In the case of a PD-L1 mediated disease or condition, the therapeutically effective amount of the therapeutic agent is an amount that reduces, prevents, inhibits, and/or relieves to some extent one or more of the symptoms associated with the disease, disorder, or condition. For cancer therapy, efficacy in vivo can, for example, be measured by assessing the growth of a primary tumor, occurrence and/or growth of secondary tumor(s), occurrence and/or number of metastases, duration, severity, and/or recurrence of symptoms, the response rate (RR), duration of response, and/or quality of life.

"Concurrently," as used herein, refers to administration of two or more therapeutic agents, where at least part of the administration overlaps in time. Accordingly, concurrent administration includes a dosing regimen when the administration of one or more agent(s) continues after discontinuing the administration of one or more other agent(s).

"Individual" or "subject" refers to a mammal, including but not limited to, domesticated animals (e.g., cows, sheep, cats, dogs, and horses), primates (e.g., humans and non-human primates such as monkeys), rabbits, and rodents (e.g., mice and rats).

DETAILED DESCRIPTION OF VARIOUS EMBODIMENTS

I. PD-L1 and PD1

The sequence and annotation of human PD-L1 (also referred to herein as "huPD-L1" or "hPD-L1) can be found at UniProt entry Q9NZQ7, and the full-length, 290 amino acid isoform 1 sequence of hPD-L1 is set forth herein as SEQ ID NO: 173. A shorter recombinant human PD-L1.ECD segment of SEQ ID NO: 174 was used in the Examples described elsewhere herein.

The sequence and annotation of cynomolgus monkey PD-L1 (also referred to herein as "cynoPD-L1") can be found at NCBI Reference Sequence XP_015292694.1/XP_014973151.1. A shorter recombinant cyno PD-L1.ECD segment of SEQ ID NO: 176 was used in the binding assay of the Examples described elsewhere herein.

The sequence and annotation of the human PD1, which is the cognate receptor to for human PD-1, can be found at UniProt entry Q8IX89. A shorter recombinant human PD1.ECD segment of SEQ ID NO: 175 was used in the Examples described elsewhere herein.

Table 1 below provides a summary description of the sequences of the PD-L1 and PD1 proteins, and the recombinant constructs used in the present disclosure, and their sequence identifiers. The sequences also are included in the accompanying Sequence Listing.

TABLE 1

PD-L1 and PD1 Sequences

| Name | Sequence | SEQ ID NO: |
|---|---|---|
| Human PD-L1, Isoform 1 | MRIFAVFIFMTYWHLLNAFTVTVPKDLYVVEYGSNMTIECKFPVEKQLD LAALIVYWEMEDKNIIQFVHGEEDLKVQHSSYRQRARLLKDQLSLGNAA LQITDVKLQDAGVYRCMISYGGADYKRITVKVNAPYNKINQRILVVDPV TSEHELTCQAEGYPKAEVIWTSSDHQVLSGKTTTTNSKREEKLFNVTST LRINTTTNEIFYCTFRRLDPEENHTAELVIPELPLAHPPNERTHLVILG AILLCLGVALTFIFRLRKGRMMDVKKCGIQDTNSKKQSDTHLEET | 173 |

TABLE 1-continued

PD-L1 and PD1 Sequences

| Name | Sequence | SEQ ID NO: |
|---|---|---|
| Human PD-L1.ECD (sequence used in binding assays) | FTVTVPKDLYVVEYGSNMTIECKFPVEKQLDLAALIVYWEMEDKNIIQF VHGEEDLKVQHSSYRQRARLLKDQLSLGNAALQITDVKLQDAGVYRCMI SYGGADYKRITVKVNAPYNKINQRILVVDPVTSEHELTCQAEGYPKAEV IWTSSDHQVLSGKTTTTNSKREEKLFNVTSTLRINTTTNEIFYCTFRRL DPEENHTAELVIPELPLAHPPNERT | 174 |
| Human PD1.ECD | LDSPDRPWNPPTFSPALLVVTEGDNATFTCSFSNTSESFVLNWYRMSPSN QTDKLAAFPEDRSQPGQDCRFRVTQLPNGRDFHMSVVRARRNDSGTYLCG AISLAPKAQIKESLRAELRVTERRAEVPTAHPSPSPRPAGQFQ | 175 |
| Cynomolgus PD-L1.ECD (used in mAb binding assay) | MRIFAVFIFTIYWHLLNAFTVTVPKDLYVVEYGSNMTIECKFPVEKQLDL TSLIVYWEMEDKNIIQFVHGEEDLKVQHSNYRQRAQLLKDQLSLGNAALR ITDVKLQDAGVYRCMISYGGADYKRITVKVNAPYNKINQRILVVDPVTSE HELTCQAEGYPKAEVIWTSSDHQVLSGKTTTTNSKREEKLLNVTSTLRIN TTANEIFYCIFRRLDPEENHTAELVIPELPLALPPNERT | 176 |

II. IL10

The human IL10 cytokine is a homodimeric protein of two 178 amino acid polypeptide subunits. IL10 signals through a receptor complex consisting of two IL10 receptor-1 (IL-10Rα subunit) and two IL10 receptor-2 (IL-10Rβ subunit) proteins. Consequently, the functional receptor consists of four IL10 receptor molecules. Binding of IL10 to IL-10Rα induces STAT3 signaling via the phosphorylation of the cytoplasmic tails of IL10 receptor by JAK1 and Tyk2. IL10 is primarily produced by monocytes and, to a lesser extent, lymphocytes, namely type-II T helper cells ($T_H2$), mast cells, CD4$^+$CD25$^+$Foxp3$^+$ regulatory T cells, and in a certain subset of activated T cells and B cells. IL10 can be produced by monocytes upon PD1 triggering. Table 2 below provides a summary description of the amino sequences of the human IL10 polypeptide and a recombinant IL10-Fc fusion construct used in the Examples of the present disclosure, and their sequence identifiers. The sequences also are included in the accompanying Sequence Listing.

TABLE 2

Recombinant IL10 polypeptides and polypeptide linkers

| Description | Sequence | SEQ ID NO: |
|---|---|---|
| IL10 | SPGQGTQSENSCTHFPGNLPNMLRDLRDAFSRVKTFFQMKDQLDNLLLKE SLLEDFKGYLGCQALSEMIQFYLEEVMPQAENQDPDIKAHVNSLGENLKT LRLRLRRCHRFLPCENKSKAVEQVKNAFNKLQEKGIYKAMSEFDIFINYI EAYMTMKIRN | 73 |
| IL10-Fc | SPGQGTQSENSCTHFPGNLPNMLRDLRDAFSRVKTFFQMKDQLDNLLLKE SLLEDFKGYLGCQALSEMIQFYLEEVMPQAENQDPDIKAHVNSLGENLKT LRLRLRRCHRFLPCENKSKAVEQVKNAFNKLQEKGIYKAMSEFDIFINYI EAYMTMKIRN*GGGGSGGGGSGGGGS*pkscdkthtcppcpapellggpsvf lfppkpkdtlmisrtpevtcvvvdvshedpevkfnwyvdgvevhnaktkp reeqynstyrvvsvltvlhqdwlngkeykckvsnkalpapiektiskakg qprepqvytlppsrdeltknqvsltclvkgfypsdiavewesngqpenny kttppvldsdgsfflyskltvdksrwqqgnvfscsvmhealhnhytqksl slspgk | 86 |
| Linker | LGGGGSGGGGSGGGG | 74 |
| Linker | GGGGSGGGGSGGGG | 75 |
| Linker | GGGGSGGGGSGGGGS | 76 |
| Linker | GGGGSGGGGSGGGGSGGGGS | 77 |
| Linker | GGGGSGGGGSGGGGSGGGGSGGGGS | 78 |
| Linker | GGGGSGGGGSGGGGSGGGGSGGGGSGGGGS | 79 |

IL-10: UPPERCASE UNDERLINED
Linker: *UPPERCASE ITALICS*
human IgG1 Fc fragment: bold lower case

In addition to the naturally-occurring human IL10, a variety of engineered and/or synthetically modified IL10 polypeptides that retain the cytokine functions of IL10 are known in the art. The PEGylated IL10, Pegilodecakin, has been shown to retain the anti-tumor immune surveillance function of naturally-occurring human IL10. See, Naing, A. et al. "PEGylated IL-10 (Pegilodecakin) Induces Systemic Immune Activation, CD8+ T Cell Invigoration and Polyclonal T Cell Expansion in Cancer Patients." *Cancer Cell*

34, 775-791. (2018). The engineered IL-10 variant R5A11 has been shown to have higher affinity to IL10R2, exhibit enhanced signaling activities in human CD8+ T-cells, and enhances the anti-tumor function of CAR-T cells. See, Gorby, C. et al. "Engineered IL-10 variants elicit potent immunomodulatory effects at low ligand doses." Sci Signal 13, (2020). The IL-10 from Epstein-Barr virus has weaker binding to the IL-10R1, but retains the immunosuppressive cytokine activities of human IL10, while having lost the ability to induce immunostimulatory activities with some cells. See, Yoon, S. I. et al. "Epstein-Barr virus IL-10 engages IL-10R1 by a two-step mechanism leading to altered signaling properties." J Biol Chem 287, 26586-26595 (2012). U.S. Pat. No. 7,749,490 B2 and US 2017/0015747 A1 described engineered IL10 mutants (e.g., F129S-IL10) that exhibit less immunostimulatory activity in MC/9 cell proliferation assay. Generally, it is contemplated that any engineered or modified version of IL10 polypeptide that retains some IL10 cytokine function can be used in any of the anti-PD-L1/IL10 fusion protein compositions and methods of the present disclosure.

III. Anti-PD-L1 Antibodies

In some embodiments, the present disclosure provides structures of anti-PD-L1 antibodies in terms of the amino acid and encoding nucleotide sequences of the various well-known immunoglobulin features (e.g., CDRs, FRs, $V_H$, $V_L$ domains, and full-length heavy and light chains). Table 3 below provides a summary description of anti-PD-L1 antibody sequences of the present disclosure, including antibody fusions, and their sequence identifiers. The sequences are included in the accompanying Sequence Listing.

TABLE 3

Anti-PD-L1 antibody (including antibody fusion) sequences

| Protein Name | Description | Sequence | SEQ ID NO: |
|---|---|---|---|
| Atezolizumab; YW243.55.S70; MPDL3280A | CDR1-H1 | GFTFSDSWIH | 1 |
|  | CDR1-H2 | AWISPYGGSTYYADSVKG | 2 |
|  | CDR1-H3 | RHWPGGFDY | 3 |
|  | $V_H$ domain | EVQLVESGGGLVQPGGSLRLSCAASGFTFSDSWIHWVRQAPGK GLEWVAWISPYGGSTYYADSVKGRFTISADTSKNTAYLQMNSL RAEDTAVYYCARRHWPGGFDYWGQGTLVTVSA | 4 |
|  | Heavy Chain | EVQLVESGGGLVQPGGSLRLSCAASGFTFSDSWIHWVRQAPGK GLEWVAWISPYGGSTYYADSVKGRFTISADTSKNTAYLQMNSL RAEDTAVYYCARRHWPGGFDYWGQGTLVTVSSastkgpsvfpla psskstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsreemtknqvsltclvkgfypsdiavewesngqp ennykttppvldsdgsfflyskltvdksrwqqgnvfscsvmhe alhnhytqkslslspgk | 143 |
|  | CDR1-L1 | RASQDVSTAVA | 5 |
|  | CDR1-L2 | SASFLYS | 6 |
|  | CDR1-L3 | QQYLYHPAT | 7 |
|  | $V_L$ domain | DIQMTQSPSSLSASVGDRVTITCRASQDVSTAVAWQQKPGKAP KLLIYSASFLYSGVPSRFSGSGSGTDFTLTISSLQPEDFATYY CQQYLYHPATFGQGTKVEIKR | 8 |
|  | Light Chain | DIQMTQSPSSLSASVGDRVTITCRASQDVSTAVAWQQKPGKAP KLLIYSASFLYSGVPSRFSGSGSGTDFTLTISSLQPEDFATYY CQQYLYHPATFGQGTKVEIKRrtvaapsvfifppsdeqlksgt asvvcllnnfypreakvqwkvdnalqsgnsqesvteqdskdst yslsstltlskadyekhkvyacevthqglsspvtksfnrgec | 144 |
| Avelumab; A09-246-2; MSB0010718C | CDR1-H1 | SYIMM | 9 |
|  | CDR1-H2 | SIYPSGGITFYADTVKG | 10 |
|  | CDR1-H3 | IKLGTVTTVDY | 11 |
|  | $V_H$ domain | EVQLLESGGGLVQPGGSLRLSCAASGFTFSSYIMMWVRQAPGK GLEWVSSIYPSGGITFYADTVKGRFTISRDNSKNTLYLQMNSL RAEDTAVYYCARIKLGTVTTVDYWGQGTLVTVSS | 12 |
|  | Heavy Chain | EVQLLESGGGLVQPGGSLRLSCAASGFTFSSYIMMWVRQAPGK GLEWVSSIYPSGGITFYADTVKGRFTISRDNSKNTLYLQMNSL RAEDTAVYYCARIKLGTVTTVDYWGQGTLVTVSSastkgpsvf plapsskstsggtaalgclvkdyfpepvtvswnsgaltsgvht fpavlqssglyslssvvtvpssslgtqtyicnvnhkpsntkvd kkvepkscdkthtcppcpapellggpsvflfppkpkdtlmisr tpevtcvvvdvshedpevkfnwyvdgvevhnaktkpreeqyns tyrvvsvltvlhqdwlngkeykckvsnkalpapiektiskakg qprepqvytlppsreemtknqvsltclvkgfypsdiavewesn gqpennykttppvldsdgsfflyskltvdksrwqqgnvfscsv mhealhnhytqkslslspgk | 145 |
|  | CDR1-L1 | TGTSSDVGGYNYVS | 13 |
|  | CDR1-L2 | DVSNRPS | 14 |
|  | CDR1-L3 | SSYTSSSTRV | 15 |
|  | $V_L$ domain | QSALTQPASVSGSPGQSITISCTGTSSDVGGYNYVSWYQQHPG KAPKLMIYDVSNRPSGVSNRFSGSKSGNTASLTISGLQAEDEA DYYCSSYTSSSTRVFGTGTKVTVL | 16 |

TABLE 3-continued

Anti-PD-L1 antibody (including antibody fusion) sequences

| Protein Name | Description | Sequence | SEQ ID NO: |
|---|---|---|---|
| | Light Chain | QSALTQPASVSGSPGQSITISCTGTSSDVGGYNYVSWYQQHPG KAPKLMIYDVSNRPSGVSNRFSGSKSGNTASLTISGLQAEDEA DYYCSSYTSSSTRVFGTGTKVTVLgqpkanptvtlfppsseel qankatlvclisdfypgavttvawkadgspvkagvettkpskqs nnkyaassylsltpeqwkshrsyscqvthegstvektvaptec s | 146 |
| Durvalumab; MEDI4736; 2.14H9 | CDR1-H1 | GFTFSRYWMS | 17 |
| | CDR1-H2 | NIKQDGSEKYYVDSVKG | 18 |
| | CDR1-H3 | EGGWFGELAFDY | 19 |
| | V$_H$ domain | EVQLVESGGGLVQPGGSLRLSCAASGFTFSRYWMSWVRQAPGK GLEWVANIKQDGSEKYYVDSVKGRFTISRDNAKNSLYLQMNSL RAEDTAVYYCAREGGWFGELAFDYWGQGTLVTVSS | 20 |
| | Heavy Chain | EVQLVESGGGLVQPGGSLRLSCAASGFTFSRYWMSWVRQAPGK GLEWVANIKQDGSEKYYVDSVKGRFTISRDNAKNSLYLQMNSL RAEDTAVYYCAREGGWFGELAFDYWGQGTLVTVSSastkgpsv fplapsskstsggtaalgclvkdyfppvtvswnsgaltsgvht fpavlqssglyslssvvtvpssslgtqtyicnvnhkpsntkvd kkvepkscdkthtcppcpapellggpsvflfppkpkdtlmisr tpevtcvvvdvshedpevkfnwyvdgvevhnakttkpreeqyas tyrvvsvltvlhqdwlngkeykckvsnkalpapiektiskakg qprepqvytlppsreemtknqvsltclvkgfypsdiavewesn gqpennykttppvldsdgsfflysklvdksrwqqgnvfscsv mhealhnhytqkslslspgk | 147 |
| | CDR1-L1 | RASQRVSSSYLA | 21 |
| | CDR1-L2 | DASSRAT | 22 |
| | CDR1-L3 | QQYGSLPWT | 23 |
| | V$_L$ domain | EIVLTQSPGTLSLSPGERATLSCRASQRVSSSYLAWYQQKPGQ APRLLIYDASSRATGIPDRFSGSGSGTDFTLTISRLEPEDFAW YYCQQYGSLPWTFGQGTKVEIK | 24 |
| | Light Chain | EIVLTQSPGTLSLSPGERATLSCRASQRVSSSYLAWYQQKPGQ APRLLIYDASSRATGIPDRFSGSGSGTDFTLTISRLEPEDFAW YYCQQYGSLPWTFGQGTKVEIKrtvaapsvfifppsdeqlksg tasvvcllnnfypreakvqwkvdnalqsgnsqesvteqdskds tyslsstltlskadyekhkvyacevthqglsspvtksfnrgec | 148 |
| Lodapolimab; LY3300054; Antibody A | CDR1-H1 | KASGGTFSSYAIS | 25 |
| | CDR1-H2 | GIIPIFGTANYAQKFQG | 26 |
| | CDR1-H3 | ARSPDYSPYYYYGMDV | 27 |
| | V$_H$ domain | QVQLVQSGAEVKKPGSSVKVSCKASGGTFSSYAISWVRQAPGQ GLEWMGGIIPIFGTANYAQKFQGRVTITADKSTSTAYMELSSL RSEDTAVYYCARSPDYSPYYYYGMDVWGQGTTVTVSS | 28 |
| | CDR1-L1 | SGSSSNIGSNTVN | 29 |
| | CDR1-L2 | YGNSNRPS | 30 |
| | CDR1-L3 | QSYDSSLSGSV | 31 |
| | V$_L$ domain | QSVLTQPPSASGTPGQRVTISCSGSSSNIGSNTVNWYQQLPGT APKLLIYGNSNRPSGVPDRFSGSKSGTSASLAISGLQSEDEAD YYCQSYDSSLSGSVFGGGIKLTVLG | 32 |
| FAZ053; BAP058-hum13 | CDR1-H1 | SYWMY | 33 |
| | CDR1-H2 | RIDPNSGSTKYNEKFKN | 34 |
| | CDR1-H3 | DYRKGLYAMDY | 35 |
| | V$_H$ domain | EVQLVQSGAEVKKPGATVKISCKVSGYTFTSYWMYWVRQARGQ RLEWIGRIDPNSGSTKYNEKFKNRFTISRDNSKNTLYLQMNSL RAEDTAVYYCARDYRKGLYAMDYWGQGTTVTVSS | 36 |
| | CDR1-L1 | KASQDVGTAVA | 37 |
| | CDR1-L2 | WASTRHT | 38 |
| | CDR1-L3 | QQYNSYPLT | 39 |
| | V$_L$ domain | AIQLTQSPSSLSASVGDRVTITCKASQDVGTAVAWYLQKPGQS PQLLIYWASTRHTGVPSRFSGSGSGTDFTFTISSLEAEDAATY YCQQYNSYPLTFGQGTKVEIK | 40 |
| MDX-1105; BMS-936559; 12A4 | CDR1-H1 | TYAIS | 41 |
| | CDR1-H2 | GIIPIFGKAHYAQKFQG | 42 |
| | CDR1-H3 | KFHFVSGSPFGMDV | 43 |
| | V$_H$ domain | QVQLVQSGAEVKKPGSSVKVSCKTSGDTFSTYAISWVRQAPGQ GLEWMGGIIPIFGKAHYAQKFQGRVTITADESTSTAYMELSSL RSEDTAVYFCARKFHFVSGS PFGMDVWGQGTTVTVSS | 44 |
| | CDR1-L1 | RASQSVSSYLA | 45 |
| | CDR1-L2 | DASNRAT | 46 |
| | CDR1-L3 | QQRSNWPT | 47 |
| | V$_L$ domain | EIVLTQSPATLSLSPGERATLSCRASQSVSSYLAWYQQKPGQAP RLLIYDASNRATGIPARFSGSGSGTDFTLTISSLEPEDFAVYY CQQRSNWPTFGQGTKVEIK | 48 |

TABLE 3-continued

Anti-PD-L1 antibody (including antibody fusion) sequences

| Protein Name | Description | Sequence | SEQ ID NO: |
|---|---|---|---|
| PHS102 | CDR1-H1 | AASGFTITDSFIH | 49 |
| | CDR1-H2 | RIDPYGGTTN | 50 |
| | CDR1-H3 | ARAYSWFSDY | 51 |
| | $V_H$ domain | EVQLVESGGGLVQPGGSLRLSCAASGFTITDSFIHWVRQAPGK GLEWVARIDPYGGTTNYADSVKGRFTISADTSKNTAYLQMNSL RAEDTAVYYCARAYSWFSDYWGQGTLVTVSS | 52 |
| | Heavy Chain | EVQLVESGGGLVQPGGSLRLSCAASGFTITDSFIHWVRQAPGK GLEWVARIDPYGGTTNYADSVKGRFTISADTSKNTAYLQMNSL RAEDTAVYYCARAYSWFSDYWGQGTLVTVSSastkgpsvfplap sskstsggtaalgclvkdyfpepvtvswnsgaltsgvhtfpav lqssglyslssvvtvpssslgtqtyicnvnhkpsntkvdkkve pkscdkthtcppcpapellggpsvflfppkpkdtlmisrtpev tcvvvdvshedpevkfnwyvdgvevhnaktkpreeqyastyrv vsvltvlhqdwlngkeykckvsnkalpapiektiskakgqpre pqvytlppsreemtknqvsltclvkgfypsdiavewesngqpe nnykttppvldsdgsfflysklt vdksrwqqgnvfscsvmhea lhnhytqkslslspgk | 149 |
| | CDR1-L1 | RAGQDVYKAVA | 53 |
| | CDR1-L2 | YWSTNLYS | 54 |
| | CDR1-L3 | GSTWPLTF | 55 |
| | $V_L$ domain | DIQMTQSPSSLSASVGDRVTITC<u>RAGQDVYKAVA</u>WYQQKPGKA PKLLI<u>YWSTNLYS</u>GVPSRFSGSGSGTDFTLTISSLQPEDFATY YCQQ<u>GSTWPLTF</u>GQGTKVEIK | 56 |
| | Light Chain | DIQMTQSPSSLSASVGDRVTITC<u>RAGQDVYKAVA</u>WYQQKPGKA PKLLI<u>YWSTNLYS</u>GVPSRFSGSGSGTDFTLTISSLQPEDFATY YCQQ<u>GSTWPLTF</u>GQGTKVEIKrtvaapsvfifppsdeqlksgt asvvcllnnfypreakvqwkvdnalqsgnsqesvteqdskdst yslsstltlskadyekhkvyacevthqglsspvtksfnrgec | 142 |
| | scFv (DNA) | ATGGCCGATATTCAAATGACCCAGAGCCCGAGCAGCCTGAGCG CGAGCGTGGGAGATCGCGTGACCATTACCTGCCGTGCGGGCCA GGATGTTTACAAAGCTGTCGCATGGTATCAGCAGAAACCAGGC AAAGCGCCGAAACTTCTGATATACTGGTCCACTAACCTGTATA GCGGCGTGCCGTCGCGTTTTTCGGGCAGTGGCAGCGGCACGGA CTTTACCCTGACGATATCTTCCTTACAACCGGAGGATTTTGCG ACCTACTACTGTCAACAGGGCTCCACTTGGCCGTTGACCTTCG GTCAAGGCACCAAAGTGGAAATCAAACGTGGTGGTTCTTCTAG ATCTTCCTCCTCTGGTGGCGGTGGCTCGGGCGGTGGTGGGGGA GTGCAGCTGGTGGAATCGGGAGGCGGTCTGGTGCAACCTGGCG GCAGCCTTCGTCTGAGCTGTGCGGCGAGCGGGTTCACCATTAC TGATTCTTTCATTCATTGGGTGCGTCAAGCTCCCGGCAAGGGG CTGGAGTGGGTCGCGAGGATTGATCCCTACGGCGGTACTACAA ACTATGCCGACAGCGTGAAAGGTCGCTTTACGATTAGTGCGGA CACCAGCAAAAATACCGCGTACCTGCAGATGAATAGCCTGCGT GCGGAAGACACAGCGGTGTATTATTGCGCGCGTGCGTACTCTT GGTTCTCCGATTATTGGGGCAGGGCACCCTTGTTACCGTGAG CTCGGCGTCA | 162 |
| PHS206 | CDR1-H1 | AASGFTISDFGIH | 57 |
| | CDR1-H2 | GISPDSGNTN | 58 |
| | CDR1-H3 | ARTFFRRSLDY | 59 |
| | $V_H$ domain | EVQLVESGGGLVQPGGSLRLSCAASGFTISDFGIHWVRQAPGK GLEWVAGISPDSGNTNYADSVKGRFTISADTSKNTAYLQMNSL RAEDTAVYFCARTFFRRSLDYWGQGTLVTVSS | 60 |
| | Heavy Chain | EVQLVESGGGLVQPGGSLRLSCAASGFTISDFGIHWVRQAPGK GLEWVAGISPDSGNTNYADSVKGRFTISADTSKNTAYLQMNSL RAEDTAVYFCARTFFRRSLDYWGQGTLVTVSSastkgpsvfpla psskstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsreemtknqvsltclvkgfypsdiavewesngqp ennykttppvldsdgsfflyskltvdksrwqqgnvfscsvmhe alhnhytqkslslspgk | 150 |
| | CDR1-L1 | RASQDVSSGVA | 61 |
| | CDR1-L2 | SFANYLYS | 62 |
| | CDR1-L3 | GSNLPFTF | 63 |
| | $V_L$ domain | DIQMTQSPSSLSASVGDRVTITCRASQDVSSGVAWYQQKPGKA PKLLISFANYLYSGVPSRFSGSGSGTDFTLTISSLQPEDFATY YCQQGSNLPFTFGQGTKVEIK | 64 |

TABLE 3-continued

Anti-PD-L1 antibody (including antibody fusion) sequences

| Protein Name | Description | Sequence | SEQ ID NO: |
|---|---|---|---|
| | Light Chain | DIQMTQSPSSLSASVGDRVTITCRASQDVSSGVAWYQQKPGKA PKLLISFANYLYSGVPSRFSGSGSGTDFTLTISSLQPEDFATY YCQQGSNLPFTFGQGTKVEIKrtvaapsvfifppsdeqlksgt asvvcllnnfypreakvqwkvdnalqsgnsqesvteqdskdst yslsstltlskadyekhkvyacevthqglsspvtksfnrgec | 151 |
| | scFv (DNA) | ATGGCCGATATTCAAATGACCCAGAGCCCGAGCAGCCTGAGCG CGAGCGTGGGAGATCGCGTGACCATTACCTGCCGTGCGAGCCA GGATGTTAGTAGTGGGGTCGCATGGTATCAGCAGAAACCAGGC AAAGCGCCGAAACTTCTGATATCCTTCGCCAATTACCTGTATA GCGGCGTGCCGTCGCGTTTTTCGGGCAGTGGCAGCGGCACGGA CTTTACCCTGACGATATCTTCCTTACAACCGGAGGATTTTGCG ACCTACTACTGTCAACAGGGTTCCAACCTCCCGTTCACCTTCG GTCAAGGCACCAAAGTGGAAATCAAACGCGGTGGTTCCTCTAG ATCTTCCACCTCTGGTGGCGGTGGCTCGGGCGGTGGTGGGGAA GTGCAGCTGGTGGAATCGGGAGGCGGTCTGGTGCAACCTGGCG GCAGCCTTCGTCTGAGCTGTGCGGCGAGCGGGTTCACCATTAG CGATTTTGGGATTCATTGGGTGCGTCAAGCTCCCGGCAAGGGG CTGGAGTGGGTCGCGGGGATTTCCCCCGACAGTGGTAACACAA ACTATGCCGACAGCGTGAAAGGTCGCTTTACGATTAGTGCGGA CACCAGCAAAAATACCGCGTACCTGCAGATGAATAGCCTGCGT GCGGAAGACACAGCGGTGTATTTTGCGCGCGTACTTTTTTTA GGCGGAGTCTGGATTATTGGGGGCAGGGCACCCTTGTTACCGT GAGCTCGGCGTCA | 163 |
| PHS219 | CDR1-H1 | AASGFTISNSFIH | 65 |
| | CDR1-H2 | DISPYSGYTN | 66 |
| | CDR1-H3 | ARTPAWGYMDY | 67 |
| | V$_H$ domain | EVQLVESGGGLVQPGGSLRLSCAASGFTISNSFIHWVRQAPGK GLEWVADISPYSGYTNYADSVKGRFTISADTSKNTAYLQMNSL RAEDTAVYYCARTPAWGYMDYWGQGTLVTVSS | 68 |
| | Heavy Chain | EVQLVESGGGLVQPGGSLRLSCAASGFTISNSFIHWVRQAPGK GLEWVADISPYSGYTNYADSVKGRFTISADTSKNTAYLQMNSL RAEDTAVYYCARTPAWGYMDYWGQGTLVTVSSastkgpsvfpla psskstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsreemtknqvsltclvkgfypsdiavewesngqp ennykttppvldsdgsfflysklvdksrwqqgnvfscsvmhe alhnhytqkslslspgk | 152 |
| | CDR1-L1 | RASQDVSSSVA | 69 |
| | CDR1-L2 | SWATSLYS | 70 |
| | CDR1-L3 | YNNFPYTF | 71 |
| | V$_L$ domain | DIQMTQSPSSLSASVGDRVTITCRASQDVSSSVAWYQQKPGKA QKLLISWATSLYSGVPSRFSGSGSGTDFTLTISSLQPEDFATY YCQQYNNFPYTFGQGTKVEIK | 72 |
| | Light Chain | DIQMTQSPSSLSASVGDRVTITCRASQDVSSSVAWYQQKPGKA QKLLISWATSLYSGVPSRFSGSGSGTDFTLTISSLQPEDFATY YCQQYNNFPYTFGQGTKVEIKrtvaapsvfifppsdeqlksgt asvvcllnnfypreakvqwkvdnalqsgnsqesvteqdskdst yslsstltlskadyekhkvyacevthqglsspvtksfnrgec | 153 |
| | scFv (DNA) | ATGGCCGATATTCAAATGACCCAGATCCCGAGCAGCCTGAGCG CGAGCGTGGGAGATCGCGTGACCATTACCTGCCGTGCGAGCCA GGATGTTAGCAGTTCCGTCGCATGGTATCAGCAGAAACCAGGC AAAGCGCAGAAACTTCTGATATCCTGGGCAACTTCTCTGTATA GCGGCGTGCCGTCGCGTTTTTCGGGCAGTGGCAGCGGCACGGA CTTTACCCTGACGATATCTTCCTTACAACCGGAGGATTTTGCG ACCTACTACTGTCAACAGTACAATAACTTTCCGTACACCTTCG GTCAAGGCACCAAAGTGGAAATCAAACGCGGTAGTTCCTCTAG ATCTTCCTCCTCTGGTGGCGGTGGCTCGGGCGGTGGTGGGGAA GTGCAGCTGGTGGAATCGGGAGGCGGTCTGGTGCAACCTGGCG GCAGCCTTCGTCTGAGCTGTGCGGCGAGCGGGTTCACCATTAG CAACTCTTTTATTCATTGGGTGCGTCAAGCTCCCGGCAAGGGG CTGGAGTGGGTCGCGGACATTTCTCCCTACAGTGGTTATACAA ATTATGCCGACAGCGTGAAAGGTCGCTTTACGATTAGTGCGGA CACCAGCAAAAATACCGCGTACCTGCAGATGAATAGCCTGCGT GCGGAAGACACAGCGGTGTATTATTGCGCGCGTACTCCTGCTT GGGGGTATATGGATTATTGGGGGCAGGGCACCCTTGTTACCGT GAGCTCGGCGTCA | 164 |
| PHS102.HSYPP31F | CDR1-H1 | AASGFTIEDSYIH | 105 |
| | CDR1-H2 | RIDPITGLTH | 106 |
| | CDR1-H3 | ARAFSWFPDY | 95 |
| | V$_H$ domain | EVQLVESGGGLVQPGGSLRLSCAASGFTIEDSYIHWVRQAPGK | 107 |

TABLE 3-continued

Anti-PD-L1 antibody (including antibody fusion) sequences

| Protein Name | Description | Sequence | SEQ ID NO: |
|---|---|---|---|
| | | GLEWVARIDPITGLTHYADSVKGRFTISADTSKNTAYLQMNSL RAEDTAVYYCARAFSWFPDYWGQGTLVTVSS | |
| | Heavy Chain | EVQLVESGGGLVQPGGSLRLSCAASGFTIEDSYIHWVRQAPGK GLEWVARIDPITGLTHYADSVKGRFTISADTSKNTAYLQMNSL RAEDTAVYYCARAFSWFPDYWGQGTLVTVSSastkgpsvfpla psskstsggtaalgclvkdyfpepvtvswnsgaltsgvhtfpa vlqssglyslssvvtvpssslgtqtyicnvnhkpsntkvdkkv epksedkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsreemtknqvsltclvkgfypsdiavewesngqp ennykttppvldsdgsfflysklтvdksrwqqgnvfscsvmhe alhnhytqkslslspgk | 157 |
| | CDR1-L1 | RAGQDVYKAVA | 53 |
| | CDR1-L2 | YWSTNLYS | 54 |
| | CDR1-L3 | IMEPPVT | 108 |
| | V$_L$ domain | DIQMTQSPSSLSASVGDRVTITCRAGQDVYKAVAWYQQKPGKA PKLLIYWSTNLYSGVPSRFSGSGSGTDFTLTISSLQPEDFATY YCQQIMEPPVTFGQGTKVEIK | 109 |
| | Light Chain | DIQMTQSPSSLSASVGDRVTITCRAGQDVYKAVAWYQQKPGKA PKLLIYWSTNLYSGVPSRFSGSGSGTDFTLTISSLQPEDFATY YCQQIMEPPVTFGQGTKVEIKrtvaapsvfifppsdeqlksgt asvvcllnnfypreakvqwkvdnalqsgnsqesvteqdskdst yslssтltlskadyekhkvyacevthqglsspvtksfnrgec | 134 |
| | scFv (DNA) | ATGGCCGATATTCAAATGACCCAGAGCCCGAGCAGCCTGAGCG CGAGCGTGGGAGATCGCGTGACCATTACCTGCCGTGCGGGCCA GGATGTTTACAAAGCTGTCGCATGGTATCAGCAGAAACCAGGT AAAGCGCCGAAACTTCTGATATACTGGTCCACTAACCTGTATA GCGGCGTGCCGTCGCGTTTTTCGGGCAGTGGCAGCGGCACGGA CTTTACCCTGACGATATCTTCCTTACAACCGGAGGATTTTGCG ACCTACTACTGTCAACAGATTATGGAGCCGCCGGTTACCTTCG GTCAAGGCACCAAAGTGGAAATCAAACGTGGTGGTTCCGCTAG ATCTTCCTCTGGTGGCGGTGGCTCGGGCGGTGGTGGGGAA GTGCAGCTGGTGGAATCGGGAGGCGGTCTGGTGCAACCTGGCG GCAGCCTTCGTCTGAGCTGTGCGGCGAGCGGGTTCACCATTGA GGATTCGTATATTCATTGGGTGCGTCAAGCTCCCGGCAAGGGG CTGGAGTGGGTCGCGAGGATTGATCCCATTACGGGTTTGACAC ATTATGCCGACAGCGTGAAAGGTCGCTTTACGATTAGTGCGGA CACCAGCAAAAATACCGCGTACCTGCAGATGAATAGCCTGCGT GCGGAAGACACAGCGGTGTATTATTGCGCGCGTGCTTTTAGTT GGTTTCCGGATTATTGGGGCAGGGCACCCTTGTTACCGTGAG CTCGGCGTCA | 168 |
| PHS102.HSYPP411C | CDR1-H1 | AASGFTIDNTYIH | 93 |
| | CDR1-H2 | RIDPANGKTT | 110 |
| | CDR1-H3 | ARSFSWWADY | 111 |
| | V$_H$ domain | EVQLVESGGGLVQPGGSLRLSCAASGFTIDNTYIHWVRQAPGK GLEWVARIDPANGKTTYADSVKGRFTISADTSKNTANLQMNSL RAEDTAVYYCARSFSWWADYWGQGTLVTVSS | 112 |
| | Heavy Chain | EVQLVESGGGLVQPGGSLRLSCAASGFTIDNTYIHWVRQAPGK GLEWVARIDPANGKTTYADSVKGRFTISADTSKNTANLQMNSL RAEDTAVYYCARSFSWWADYWGQGTLVTVSSastkgpsvfpla psskstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsreemtknqvsltclvkgfypsdiavewesngqp ennykttppvldsdgsfflysklтvdksrwqqgnvfscsvmhe alhnhytqkslslspgk | 158 |
| | CDR1-L1 | RAGQDVYKAVA | 53 |
| | CDR1-L2 | YWSTNLYS | 54 |
| | CDR1-L3 | FNLQPTT | 113 |
| | V$_L$ domain | DIQMTQSPSSLSASVGDRVTITCRAGQDVYKAVAWYQQKPGKA PKLLIYWSTNLYSGVPSRFSGSGSGTDFTLTISSLQPEDFATY YCQQFNLQPTTFGQGTKVEIK | 114 |
| | Light Chain | DIQMTQSPSSLSASVGDRVTITCRAGQDVYKAVAWYQQKPGKA PKLLIYWSTNLYSGVPSRFSGSGSGTDFTLTISSLQPEDFATY YCQQFNLQPTTFGQGTKVEIKrtvaapsvfifppsdeqlksgt asvvcllnnfypreakvqwkvdnalqsgnsqesvteqdskdst yslssтltlskadyekhkvyacevthqglsspvtksfnrgec | 136 |
| | scFv (DNA) | ATGGCCGATATTCAAATGACCCAGAGCCCGAGCAGCCTGAGCG CGAGCGTGGGAGATCGCGTGACCATTACCTGCCGTGCGGGCCA GGATGTTTACAAAGCTGTCGCATGGTATCAGCAGAAACCAGGC AAAGCGCCGAAACTTCTGATATACTGGTCCACTAACCTGTATA | 169 |

TABLE 3-continued

Anti-PD-L1 antibody (including antibody fusion) sequences

| Protein Name | Description | Sequence | SEQ ID NO: |
|---|---|---|---|
| | | GCGGCGTGCCGTCGCGTTTTTCGGGCAGTGGCAGCGGCACGGA CTTTACCCTGACGATATCTTCCTTACAACCGGAGGATTTTGCG ACCTACTACTGTCAACAGTTTAATCTGCAGCCGACTACCTTCG GTCAAGGCACCAAAGTGGAAATCAAACGTGGTGGTTCCTCTAG ATCTTCCTCCTCTGGTGGCGGTGGCTCGGGCGGTGGTGGGGAA GTGCAGCTGGTGGAATCGGGAGGCGGTCTGGTGCAACCTGGCG GCAGCCTTCGTCTGAGCTGTGCGGCGAGCGGGTTCACCATTGA TAATACGTATATTCATTGGGTGCGTCAAGCTCCCGGCAAGGGG CTGGAGTGGGTCGCGAGGATTGATCCCGCGAATGGTAAGACAA CTTATGCCGACAGCGTGAAAGGTCGCTTTACGATTAGTGCGGA CACCAGCAAAAATACCGCGAACCTGCAGATGAATAGCCTGCGT GCGGAAGACACAGCGGTGTATTATTGCGCGCGTGCTTTTTCGT GGTGGGCTGATTATTGGGGGCAGGGCACCCTTGTTACCGTGAG CTCGGCGTCA | |
| PHS102.YP7G | CDR1-H1 | AASGFTIDDTYIH | 124 |
| | CDR1-H2 | RIDPANGMTR | 125 |
| | CDR1-H3 | ARAFSWFPDY | 95 |
| | V<sub>H</sub> domain | EVQLVESGGGLVQPGGSLRLSCAASGFTIDDTYIHWVRQAPGK GLEWVARIDPANGMTRYADSVKGRFMISADTSKNTAYLQMNSL RAEDTAVYYCARAFSWFPDYWGQGTLVTVSS | 126 |
| | Heavy Chain | EVQLVESGGGLVQPGGSLRLSCAASGFTIDDTYIHWVRQAPGK GLEWVARIDPANGMTRYADSVKGRFMISADTSKNTAYLQMNSL RAEDTAVYYCARAFSWFPDYWGQGTLVTVSSastkgpsvfpla psssksstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsreemtknqvsltclvkgfypsdiavewesngqp ennykttppvldsdgsfflysklfvdksrwqqgnvfscsvmhe alhnhytqkslslspgk | 161 |
| | CDR1-L1 | RAGQDVYKAVA | 53 |
| | CDR1-L2 | YWSTNLYS | 54 |
| | CDR1-L3 | GSTWPLTF | 55 |
| | V<sub>L</sub> domain | DIQMTQSPSSLSASVGDRVTITCRAGQDVYKAVAWYQQKPGKA PKLLIYWSTNLYSGVPSRFSGSGSGTDFTLTISSLQPEDFATY YCQQGSTWPLTFGQGTKVEIK | 56 |
| | Light Chain | DIQMTQSPSSLSASVGDRVTITCRAGQDVYKAVAWYQQKPGKA PKLLIYWSTNLYSGVPSRFSGSGSGTDFTLTISSLQPEDFATY YCQQGSTWPLTFGQGTKVEIKrtvaapsvfifppsdeqlksgt asvvcllnnfypreakvqwkvdnalqsgnsqesvteqdskdst yslsstltlskadyekhkvyacevthqglsspvtksfnrgec | 142 |
| | scFv (DNA) | ATGGCCGATATTCAAATGACCCAGAGCCCGAGCAGCCTGAGCG CGAGCGTGGGAGATCGCGTGACCATTACCTGCCGTGCGGGCCA GGATGTTTACAAAGCTGTCGCATGGTATCAGCAGAAACCAGGC AAAGCGCCGAAACTTCTGATATACTGGTCCACTAACCTGTATA GCGGCGTGCCGTCGCGTTTTTCGGGCAGTGGCAGCGGCACGGA CTTTACCCTGACGATATCTTCCTTACAACCGGAGGATTTTGCG ACCTACTACTGTCAACAGGGCTCCACTTGGCCGTTGACCTTCG GTCAAGGCACCAAAGTGGAAATCAAACGTGGTGGTTCCTCTAG ATCTTCCTCCTCTGGTGGCGGTGGCTCGGGCGGTGGTGGGGAA GTGCAGCTGGTGGAATCGGGAGGCGGTCTGGTGCAACCTGGCG GCAGCCTTCGTCTGAGCTGTGCGGCGAGCGGGTTCACCATTGA TGATACTTATATTCATTGGGTGCGTCAAGCTCCCGGCAAGGGG CTGGAGTGGGTCGCGAGGATTGATCCCGCGAATGGTATGACAA GGTATGCCGACAGCGTGAAGGGTCGCTTTATGATTAGTGCGGA CACCAGCAAAAATACCGCGTACCTGCAGATGAATAGCCTGCGT GCGGAAGACACAGCGGTGTATTATTGCGCGCGTGCTTTTTCTT GGTTTCCTGATTATTGGGGGCAGGGCACCCTTGTTACCGTGAG CTCGGCGTCA | 172 |
| PHS102.YP11F | CDR1-H1 | AASGFTIDNTYIH | 93 |
| | CDR1-H2 | RIDPVSGRTR | 94 |
| | CDR1-H3 | ARAFSWFPDY | 95 |
| | V<sub>H</sub> domain | EVQLVESGGGLVQPGGSLRLSCAASGFTIDNTYIHWVRQAPGK GLEWVARIDPVSGRTRYADSVKGRFTISADTSKNTADLQMNSL RAEDTAVYYCARAFSWFPDYWGQGTLVTVSS | 96 |
| | Heavy Chain | EVQLVESGGGLVQPGGSLRLSCAASGFTIDNTYIHWVRQAPGK GLEWVARIDPVSGRTRYADSVKGRFTISADTSKNTADLQMNSL RAEDTAVYYCARAFSWFPDYWGQGTLVTVSSastkgpsvfpla psssksstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr | 155 |

TABLE 3-continued

Anti-PD-L1 antibody (including antibody fusion) sequences

| Protein Name | Description | Sequence | SEQ ID NO: |
|---|---|---|---|
| | | vvsvltvlhqdwlngkeykckvsnkalpapiektiskakgqpr epqvytlppsreemtknqvsltclvkgfypsdiavewesngqp ennykttppvldsdgsfflyskltvdksrwqqgnvfscsvmhe alhnhytqkslslspgk | |
| | CDR1-L1 | RAGQDVYKAVA | 53 |
| | CDR1-L2 | YWSTNLYS | 54 |
| | CDR1-L3 | FGATPITF | 97 |
| | V$_L$ domain | DIQMTQSPSSLSASVGDRVTITCRAGQDVYKAVAWYQQKPGKA PKLLIYWSTNLYSGVPSRFSGSGSGTDFTLTISSLQPEDFATY YCQQFGATPITFGQGTKVEIK | 98 |
| | Light Chain | DIQMTQSPSSLSASVGDRVTITCRAGQDVYKAVAWYQQKPGKA PKLLIYWSTNLYSGVPSRFSGSGSGTDFTLTISSLQPEDFATY YCQQFGATPITFGQGTKVEIKrtvaapsvfifppsdeqlksgt asvvcllnnfypreakvqwkvdnalqsgnsqesvteqdskdst yslsstltlskadyekhkvyacevthqglsspvtksfnrgec | 130 |
| | scFv (DNA) | ATGGCCGATATTCAAATGACCCAGAGCCCGAGCAGCCTGAGCG CGAGCGTGGGAGATCGCGTGACCATTACCTGCCGTGCGGGCCA GGATGTTTACAAAGCTGTCGCATGGTATCAGCAGAAACCAGGC AAAGCGCCGAAACTTCTGATATACTGGTCCACTAACCTGTATA GCGGCGTGCCGTCGCGTTTTTCGGGCAGTGGCAGCGGCACGGA CTTTACCCTGACGATATCTTCCTTACAACCGGAGGATTTTGCG ACCTACTACTGTCAACAGTTTGGGGCGACTCCGATTACCTTCG GTCAAGGCACCAAAGTGGAAATCAAACGTGGTGGTTCCGCTAG ATCTTCCTCCTCTGGTGGCGGTGGCTCGGGCGGTGGTGGGGAA GTGCAGCTGGTGGAATCGGGAGGCGGTCTGGTGCAACCTGGCG GCAGCCTTCGTCTGAGCTGTGCGGCGAGCGGGTTCACCATTGA TAATACTTATATTCATTGGGTGCGTCAAGCTCCCGGCAAGGGG CTGGAGTGGGTCGCGAGGATTGATCCCGTTAGTGGTCGTACAC GTTATGCCGACAGCGTGAAAGGTCGCTTTACGATTAGTGCGGA CACCAGCAAAAATACCGCGGACCTGCAGATGAATAGCCTGCGT GCGGAAGACACAGCGGTGTATTATTGCGCGCGTGCTTTTAGTT GGTGGCCGGATTATTGGGGGCAGGGCACCCTTGTTACCGTGAG CTCGGCGTCA | 166 |
| PHS102.YT6D | CDR1-H1 | AASGFTISDGYIH | 87 |
| | CDR1-H2 | RIDPLTGRTM | 88 |
| | CDR1-H3 | ARAFSWWPDY | 89 |
| | V$_H$ domain | EVQLVESGGGLVQPGGSLRLSC<u>AASGFTISDGYIH</u>WVRQAPGK GLEWVA<u>RIDPLTGRTM</u>YADSVKGRFTISADTSKNTAYLQMNSL RAEDTAVYYC<u>ARAFSWWPDY</u>WGQGTLVTVSS | 90 |
| | Heavy Chain | EVQLVESGGGLVQPGGSLRLSCAASGFTISDGYIHWVRQAPGK GLEWVARIDPLTGRTMYADSVKGRFTISADTSKNTAYLQMNSL RAEDTAVYYCARAFSWWPDYWGQGTLVTVSSastkgpsvfpla psskstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsreemtknqvsltclvkgfypsdiavewesngqp ennykttppvldsdgsfflyskltvdksrwqqgnvfscsvmhe alhnhytqkslslspgk | 154 |
| | CDR1-L1 | RAGQDVYKAVA | 53 |
| | CDR1-L2 | YWSTNLYS | 54 |
| | CDR1-L3 | IMSPPPTF | 91 |
| | V$_L$ domain | DIQMTQSPSSLSASVGDRVTITC<u>RAGQDVYKAVA</u>WYQQKPGKA PKLLI<u>YWSTNLYS</u>GVPSRFSGSGSGTDFTLTISSLQPEDFATY YCQQ<u>IMSPPPTF</u>GQGTKVEIK | 92 |
| | Light Chain | DIQMTQSPSSLSASVGDRVTITCRAGQDVYKAVAWYQQKPGKA PKLLIYWSTNLYSGVPSRFSGSGSGTDFTLTISSLQPEDFATY YCQQIMSPPPTFGQGTKVEIKrtvaapsvfifppsdeqlksgt asvvcllnnfypreakvqwkvdnalqsgnsqesvteqdskdst yslsstltlskadyekhkvyacevthqglsspvtksfnrgec | 128 |
| | scFv (DNA) | ATGGCCGATATTCAAATGACCCAGAGCCCGAGCAGCCTGAGCG CGAGCGTGGGAGATCGCGTGACCATTACCTGCCGTGCGGGCCA GGATGTTTACAAAGCTGTCGCATGGTATCAGCAGAAACCAGGC AAAGCGCCGAAACTTCTGATATACTGGTCCACTAACCTGTATA GCGGCGTGCCGTCGCGTTTTTCGGGCAGTGGCAGCGGCACGGA CTTTACCCTGACGATATCTTCCTTACAACCGGAGGATTTTGCG ACCTACTACTGTCAACAGATTATGAGTCCTCCGCCTACCTTCG GTCAAGGCACCAAAGTGGAAATCAAACGTGGTGGTTCCTCTAG ATCTTCCTCCTCTGGTGGCGGTGGCTCGGGCGGTGGTGGGGAA GTGCAGCTGGTGGAATCGGGAGGCGGTCTGGTGCAACCTGGCG GCAGCCTTCGTCTGAGCTGTGCGGCGAGCGGGTTCACCATTTC TGATGGGTATATTCATTGGGTGCGTCAAGCTCCCGGCAAGGGG CTGGAGTGGGTCGCGAGGATTGATCCCCTTACTGGTCGTACAA | 165 |

TABLE 3-continued

Anti-PD-L1 antibody (including antibody fusion) sequences

| Protein Name | Description | Sequence | SEQ ID NO: |
|---|---|---|---|
| | | TGTATGCCGACAGCGTGAAAGGTCGCTTTACGATTAGTGCGGA<br>CACCAGCAAAAATACCGCGTACCTGCAGATGAATAGCCTGCGT<br>GCCGGAAGACACAGCGGTGTATTATTGCGCGCGTGCTTTTTCTT<br>GGTTGGCCTGATTATTGGGGGCAGGGCACCCTTGTTACCGTGAG<br>CTCGGCGTCA | |
| PHS102.YT7A | CDR1-H1 | AASGFTIDNTYIH | 93 |
| | CDR1-H2 | RIDPANGVTR | 115 |
| | CDR1-H3 | ARAFSWFPDY | 95 |
| | V<sub>H</sub> domain | EVQLVESGGGLVQPGGSLRLSCAASGFTIDNTYIHWVRQAPGK<br>RLEWVARTDPANGVTRYADSVKGRFTISADTSKNTAYLQMNSL<br>RAEDTAVYYCARAFSWFPDYWGQGTLVTVSS | 116 |
| | Heavy Chain | EVQLVESGGGLVQPGGSLRLSCAASGFTIDNTYIHWVRQAPGK<br>RLEWVARIDPANGVTRYADSVKGRFTISADTSKNTAYLQMNSL<br>RAEDTAVYYCARAFSWFPDYWGQGTLVTVSSastkgpsvfpla<br>psskstsggtaalgclvkdyfpepvtvswnsgaltsgvhtfpa<br>vlqssglyslssvvtvpssslgtqtyicnvnhkpsntkvdkkv<br>epkscdkthtcppcpapellggpsvflfppkpkdtlmisrtpe<br>vtcvvvdvshedpevkfnwyvdgvevhnaktkpreeqyastyr<br>vvsvltvlhqdwlngkeykckvsnkalpapiektiskakgqpr<br>epqvytlppsreemtknqvsltclvkgfypsdiavewesngqp<br>ennykttppvldsdgsfflyskltvdksrwqqgnvfscsvmhe<br>alhnhytqkslslspgk | 159 |
| | CDR1-L1 | RAGQDVYKAVA | 53 |
| | CDR1-L2 | YWSTNLYS | 54 |
| | CDR1-L3 | YGIAPPTF | 117 |
| | V<sub>L</sub> domain | DIQMTQSPSSLSASVGDRVTITCRAGQDVYKAVAWYQQKPGKA<br>PKLLIYWSTNLYSGVPSRFSGSGSGTDFTLTISSLQPEDFATY<br>YCQQYGIAPPTFGQGTKVEIK | 118 |
| | Light Chain | DIQMTQSPSSLSASVGDRVTITCRAGQDVYKAVAWYQQKPGKA<br>PKLLIYWSTNLYSGVPSRFSGSGSGTDFTLTISSLQPEDFATY<br>YCQQYGIAPPTFGQGTKVEIKrtvaapsvfifppsdeqlksgt<br>asvvcllnnfypreakvqwkvdnalqsgnsqesvteqdskdst<br>yslsstltlskadyekhkvyacevthqglsspvtksfnrgec | 138 |
| | scFv (DNA) | ATGGCCGATATTCAAATGACCCAGAGCCCGAGCAGCCTGAGCG<br>CGAGCGTGGGAGATCGCGTGACCATTACCTGCCGTGCGGGCCA<br>GGATGTTTACAAAGCTGTCGCATGGTATCAGCAGAAACCAGGC<br>AAAGCGCCGAAACTTCTGATATACTGGTCCACTAACCTGTATA<br>GCGGCGTGCCGTCGCGTTTTTCGGGCAGTGGCAGCGGCACGGA<br>CTTTACCCTGACGATATCTTCCTTACAACCGGAGGATTTTGCG<br>ACCTACTACTGTCAACAGTATGGTATTGCTCCGCCTACCTTCG<br>GTCAAGGCACCAAAGTGGAAATCAAACGTGGTGGTTCCTCTAG<br>ATCTTCCTCCTCTGGTGGCGGTGGCTCGGGCGGTGGTGGGGAA<br>GTGCAGCTGGTGGAATCGGGAGGCGGTCTGGTGCAACCTGGCG<br>GCAGCCTTCGTCTGAGCTGTGCGGCGAGCGGGTTCACCATTGA<br>TAATACTTATATTCATTGGGTGCGTCAAGCTCCCGGCAAGAGG<br>CTGGAGTGGGTCGCGAGGATTGATCCCGCTAATGGTGTGACAC<br>GTTATGCCGACAGCGTGAAAGGTCGCTTTACGATTAGTGCGGA<br>CACCAGCAAAAATACCGCGTACCTGCAGATGAATAGCCTGCGT<br>GCCGGAAGACACAGCGGTGTATTATTGCGCGCGTGCTTTTTCTT<br>GGTTTCCTGATTATTGGGGGCAGGGCACCCTTGTTACCGTGAG<br>CTCGGCGTCA | 170 |
| PHS102.YT7H | CDR1-H1 | AASGFTITDGYIH | 119 |
| | CDR1-H2 | RIDPYNGRTN | 120 |
| | CDR1-H3 | ARAFSWFPDY | 95 |
| | V<sub>H</sub> domain | EVQLVESGGGLVQPGGSLRLSCAASGFTITDGYIHWVRQAPGK<br>GLEWVARIDPYNGRTNYADSVKGRFTISADTSKNTAYLQMNSL<br>RAEDTAVYYCARAFSWFPDYWGQGTLVTVSS | 121 |
| | Heavy Chain | EVQLVESGGGLVQPGGSLRLSCAASGFTITDGYIHWVRQAPGK<br>GLEWVARIDPYNGRTNYADSVKGRFTISADTSKNTAYLQMNSL<br>RAEDTAVYYCARAFSWFPDYWGQGTLVTVSSastkgpsvfpla<br>psskstsggtaalgclvkdyfpepvtvswnsgaltsgvhtfpa<br>vlqssglyslssvvtvpssslgtqtyicnvnhkpsntkvdkkv<br>epkscdkthtcppcpapellggpsvflfppkpkdtlmisrtpe<br>vtcvvvdvshedpevkfnwyvdgvevhnaktkpreeqyastyr<br>vvsvltvlhqdwlngkeykckvsnkalpapiektiskakgqpr<br>epqvytlppsreemtknqvsltclvkgfypsdiavewesngqp<br>ennykttppvldsdgsfflyskltvdksrwqqgnvfscsvmhe<br>alhnhytqkslslspgk | 160 |
| | CDR1-L1 | RAGQDVYKAVA | 53 |
| | CDR1-L2 | YWSTNLYS | 54 |

TABLE 3-continued

Anti-PD-L1 antibody (including antibody fusion) sequences

| Protein Name | Description | Sequence | SEQ ID NO: |
|---|---|---|---|
| | CDR1-L3 | HGNAPITF | 122 |
| | V$_L$ domain | DIQMTQSPSSLSASVGDRVTITCRAGQDVYKAVAWYQQKPGKA PKLLIYWSTNLYSGVPSRFSGSGSGTDFTLTISSLQPEDFATY YCQQHGNAPITFGQGTKVEIK | 123 |
| | Light Chain | DIQMTQSPSSLSASVGDRVTITCRAGQDVYKAVAWYQQKPGKA PKLLIYWSTNLYSGVPSRFSGSGSGTDFTLTISSLQPEDFATY YCQQHGNAPITFGQGTKVEIKrtvaapsvfifppsdeqlksgt asvvcllnnfypreakvqwkvdnalqsgnsqesvteqdskdst yslsstltlskadyekhkvyacevthqglsspvtksfnrgec | 140 |
| | scFv (DNA) | ATGGCCGATATTCAAATGACCCAGAGCCCGAGCAGCCTGAGCG CGAGCGTGGGAGATCGCGTGACCATTACCTGCCGTGCGGGCCA GGATGTTTACAAAGCTGTCGCATGGTATCAGCAGAAACCAGGC AAAGCGCCGAAACTTCTGATATACTGGTCCACTAACCTGTATA GCGGCGTGCCGTCGCGTTTTTCGGGCAGTGGCAGCGGCACGGA CTTTACCCTGACGATATCTTCCTTACAACCGGAGGATTTTGCG ACCTACTACTGTCAACAGCATGGTAATGCTCCGATTACCTTCG GTCAAGGCACCAAAGTGGAAATCAAACGTGGTGGTTCCTCTAG ATCTTCCTCCTCTGGTGGCGGTGGCTCGGGCGGTGGTGGGGAA GTGCAGCTGGTGGAATCGGGAGGCGGTCTGGTGCAACCTGGCG GCAGCCTTCGTCTGAGCTGTGCGGCGAGCGGGTTCACCATTAC TGATGGTTATATTCATTGGGTGCGTCAAGCTCCCGGCAAGGGG CTGGAGTGGGTCGCGAGGATTGATCCCTATAATGGTCGTACAA ATTATGCCGACAGCGTGAAAGGTCGCTTTACGATTAGTGCGGA CACCAGCAAAAATACCGCGTACCTGCAGATGAATAGCCTGCGT GCGGAAGACACAGCGGTGTATTATTGCGCGCGTGCTTTTTCTT GGTTTCCTGATTATTGGGGCAGGGCACCCTTGTTACCGTGAGC CTCGGCGTCA | 171 |
| PHS102.YT10H | CDR1-H1 | AASGFTISDAYIH | 99 |
| | CDR1-H2 | RIEPLSGRTD | 100 |
| | CDR1-H3 | ARAFSWFMDY | 101 |
| | V$_H$ domain | EVQLVESGGGLVQPGGSLRLSCAASGFTISDAYIHWVRQAPGK GLEWVARIEPLSGRTDYADSVKGRFTISADTSKNTAYLQMNSL RAEDTAVYYCARAFSWFMDYWGQGTLVTVSS | 102 |
| | Heavy Chain | EVQLVESGGGLVQPGGSLRLSCAASGFTISDAYIHWVRQAPGK GLEWVARIEPLSGRTDYADSVKGRFTISADTSKNTAYLQMNSL RAEDTAVYYCARAFSWFMDYWGQGTLVTVSSastkgpsvfpla psskstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsreemtknqvsltclvkgfypsdiavewesngqp ennykttppvldsdgsfflyskltvdksrwqqgnvfscsvmhe alhnhytqkslslspgk | 156 |
| | CDR1-L1 | RAGQDVYKAVA | 53 |
| | CDR1-L2 | YWSTNLYS | 54 |
| | CDR1-L3 | HDKTPTTF | 103 |
| | V$_L$ domain | DIQMTQSPSSLSASVGDRVTITCRAGQDVYKAVAWYQQKPGKA PKLLIYWSTNLYSGVPSRFSGSGSGTDFTLMISSLQPEDFATY YCQQHDKTPTTFGQGTKVEIK | 104 |
| | Light Chain | DIQMTQSPSSLSASVGDRVTITCRAGQDVYKAVAWYQQKPGKA PKLLIYWSTNLYSGVPSRFSGSGSGTDFTLMISSLQPEDFATY YCQQHDKTPTTFGQGTKVEIKrtvaapsvfifppsdeqlksgt asvvcllnnfypreakvqwkvdnalqsgnsqesvteqdskdst yslsstltlskadyekhkvyacevthqglsspvtksfnrgec | 132 |
| | scFv (DNA) | ATGGCCGATATTCAAATGACCCAGAGCCCGAGCAGCCTGAGCG CGAGCGTGGGAGATCGCGTGACCATTACCTGCCGTGCGGGCCA GGATGTTTACAAAGCTGTCGCATGGTATCAGCAGAAACCAGGC AAAGCGCCGAAACTTCTGATATACTGGTCCACTAACCTGTATA GCGGCGTGCCGTCGCGTTTTTCGGGCAGTGGCAGCGGCACGGA CTTTACCCTGACGATATCTTCCTTACAACCGGAGGATTTTGCG ACCTACTACTGTCAACAGCATGATAAGACTCCGACTACCTTCG GTCAAGGCACCAAAGTGGAAATCAAACGTGGTGGTTCCCCTAG ATCTTCCTCCTCTGGTGGCGGTGGCTCGGGCGGTGGTGGGGAA GTGCAGCTGGTGGAATCGGGAGGCGGTCTGGTGCAACCTGGCG GCAGCCTTCGTCTGAGCTGTGCGGCGAGCGGGTTCACCATTTC TGATGCTTATATTCATTGGGTGCGTCAGGCTCCCGGGAAGGGG CTGGAGTGGGTCGCGAGGATTGAGCCCCTGTCTGGTCGTACAG ATTATGCCGACAGCGTGAAAGGTCGCTTTACGATTAGTGCGGA CACCAGCAAAAATACCGCGTACCTGCAGATGAATAGCCTGCGT GCGGAAGACACAGCGGTGTATTATTGCGCGCGTGCTTTTAGTT GGTTTATGGATTATTGGGGCAGGGCACCCTTGTTACCGTGAGC CTCGGCGTCA | 167 |

TABLE 3-continued

Anti-PD-L1 antibody (including antibody fusion) sequences

| Protein Name | Description | Sequence | SEQ ID NO: |
|---|---|---|---|
| Atezolizumab/ IL10 | Heavy Chain | EVQLVESGGGLVQPGGSLRLSCAASGFTFSDSWIHWVRQAPGK GLEWVAWISPYGGSTYYADSVKGRFTISADTSKNTAYLQMNSL RAEDTAVYYCARRHWPGGFDYWGQGTLVTVSSastkgpsvfpla pssksstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsreemtknqvsltclvkgfypsdiavewesngqp ennykttppvldsdgsfflysklvdksrwqqgnvfscsvmhe alhnhytqkslslspgkLGGGGSGGGGSGGGGSPGQGTQSENS CTHFPGNLPNMLRDLRDAFSRVKTFFQMKDQLDNLLLKESLLE DFKGYLGCQALSEMIQFYLEEVMPQAENQDPDIKAHVNSLGEN LKTLRLRLRRCHRFLPCENKSKAVEQVKNAFNKLQEKGIYKAM SEFDIFINYIEAYMTMKIRN | 80 |
| | Light Chain | DIQMTQSPSSLSASVGDRVTITCRASQDVSTAVAWQQKPGKAP KLLIYSASFLYSGVPSRFSGSGSGTDFTLTISSLQPEDFATYY CQQYLYHPATFGQGTKVEIKRrtvaapsvfifppsdeqlksgt asvvcllnnfypreakvqwkvdnalqsgnsqesvteqdskdst yslsstltlskadyekhkvyacevthqglsspvtksfnrgec | 144 |
| Avelumab/IL10 | Heavy Chain | EVQLLESGGGLVQPGGSLRLSCAASGFTFSSYIMMWVRQAPGK GLEWVSSIYPSGGITFYADTVKGRFTISRDNSKNTLYLQMNSL RAEDTAVYYCARIKLGTVTTVDYWGQGTLVTVSSastkgpsvf plapssksstsggtaalgclvkdyfpepvtvswnsgaltsgvht fpavlqssglyslssvvtvpssslgtqtyicnvnhkpsntkvd kkvepkscdkthtcppcpapellggpsvflfppkpkdtlmisr tpevtcvvvdvshedpevkfnwyvdgvevhnaktkpreeqyns tyrvvsvltvlhqdwlngkeykckvsnkalpapiektiskakg qprepqvytlppsreemtknqvsltclvkgfypsdiavewesn gqpennykttppvldsdgsfflysklvdksrwqqgnvfscsv mhealhnhytqkslslspgkLGGGGSGGGGSGGGGSPGQGTQS ENSCTHFPGNLPNMLRDLRDAFSRVKTFFQMKDQLDNLLLKES LLEDFKGYLGCQALSEMIQFYLEEVMPQAENQDPDIKAHVNSL GENLKTLRLRLRRCHRFLPCENKSKAVEQVKNAFNKLQEKGIY KAMSEFDIFINYIEAYMTMKIRN | 81 |
| | Light Chain | QSALTQPASVSGSPGQSITISCTGTSSDVGGYNYVSWYQQHPG KAPKLMIYDVSNRPSGVSNRFSGSKSGNTASLTISGLQAEDEA DYYCSSYTSSSTRVFGTGTKVTVLgqpkanptvtlfppsseel qankatlvclisdfypgavtvawkadgspvkagvettkpskqs nnkyaassylsltpeqwkshrsyscqvthegstvektvaptec s | 146 |
| Durvalumab/IL10 | Heavy Chain | EVQLVESGGGLVQPGGSLRLSCAASGFTFSRYWMSWVRQAPGK GLEWVANIKQDGSEKYYVDSVKGRFTISRDNAKNSLYLQMNSL RAEDTAVYYCAREGGWFGELAFDYWGQGTLVTVSSastkgpsv fplapssksstsggtaalgclvkdyfppvtvswnsgaltsgvht fpavlqssglyslssvvtvpssslgtqtyicnvnhkpsntkvd kkvepkscdkthtcppcpapellggpsvflfppkpkdtlmisr tpevtcvvvdvshedpevkfnwyvdgvevhnaktkpreeqyas tyrvvsvltvlhqdwlngkeykckvsnkalpapiektiskakg qprepqvytlppsreemtknqvsltclvkgfypsdiavewesn gqpennykttppvldsdgsfflysklvdksrwqqgnvfscsv mhealhnhytqkslslspgkLGGGGSGGGGSGGGGSPGQGTQS ENSCTHFPGNLPNMLRDLRDAFSRVKTFFQMKDQLDNLLLKES LLEDFKGYLGCQALSEMIQFYLEEVMPQAENQDPDIKAHVNSL GENLKTLRLRLRRCHRFLPCENKSKAVEQVKNAFNKLQEKGIY KAMSEFDIFINYIEAYMTMKIRN | 82 |
| | Light Chain | EIVLTQSPGTLSLSPGERATLSCRASQRVSSSYLAWYQQKPGQ APRLLIYDASSRATGIPDRFSGSGSGTDFTLTISRLEPEDFAW YYCQQYGSLPWTFGQGTKVEIKRrtvaapsvfifppsdeqlksg tasvvcllnnfypreakvqwkvdnalqsgnsqesvteqdskds tyslsstltlskadyekhkvyacevthqglsspvtksfnrgec | 148 |
| PHS102/IL10 | Heavy Chain | EVQLVESGGGLVQPGGSLRLSCAASGFTITDSFIHWVRQAPGK GLEWVARIDPYGGTTNYADSVKGRFTISADTSKNTAYLQMNSL RAEDTAVYYCARAYSWFSDYWGQGTLVTVSSastkgpsvfplap ssksstsggtaalgclvkdyfpepvtvswnsgaltsgvhtfpav lqssglyslssvvtvpssslgtqtyicnvnhkpsntkvdkkve pkscdkthtcppcpapellggpsvflfppkpkdtlmisrtpev tcvvvdvshedpevkfnwyvdgvevhnaktkpreeqyastyrv vsvltvlhqdwlngkeykckvsnkalpapiektiskakgqpre pqvytlppsreemtknqvsltclvkgfypsdiavewesngqpe nnykttppvldsdgsfflysklvdksrwqqgnvfscsvmhea lhnhytqkslslspgkLGGGGSGGGGSGGGGSPGQGTQSENSC | 83 |

TABLE 3-continued

Anti-PD-L1 antibody (including antibody fusion) sequences

| Protein Name | Description | Sequence | SEQ ID NO: |
|---|---|---|---|
| | Light Chain | THFPGNLPNMLRDLRDAFSRVKTFFQMKDQLDNLLLKESLLED<br>FKGYLGCQALSEMIQFYLEEVMPQAENQDPDIKAHVNSLGENL<br>KTLRLRLRRCHRFLPCENKSKAVEQVKNAFNKLQEKGIYKAMS<br>EFDIFINYIEAYMTMKIRN<br>DIQMTQSPSSLSASVGDRVTITCRAGQDVYKAVAWYQQKPGKA<br>PKLLIYWSTNLYSGVPSRFSGSGSGTDFTLTISSLQPEDFATY<br>YCQQGSTWPLTFGQGTKVEIKrtvaapsvfifppsdeqlksgt<br>asvvcllnnfypreakvqwkvdnalqsgnsqesvteqdskdst<br>yslsstltlskadyekhkvyacevthqglsspvtksfnrgec | 142 |
| PHS206/IL10 | Heavy Chain | EVQLVESGGGLVQPGGSLRLSCAASGFTISDFGIHWVRQAPGK<br>GLEWVAGISPDSGNTNYADSVKGRFTISADTSKNTAYLQMNSL<br>RAEDTAVYFCARTFFRRSLDYWGQGTLVTVSSastkgpsvfpla<br>psskstsggtaalgclvkdyfpepvtvswnsgaltsgvhtfpa<br>vlqssglyslssvvtvpssslgtqtyicnvnhkpsntkvdkkv<br>epkscdkthtcppcpapellggpsvflfppkpkdtlmisrtpe<br>vtcvvvdvshedpevkfnwyvdgvevhnaktkpreeqyastyr<br>vvsvltvlhqdwlngkeykckvsnkalpapiektiskakgqpr<br>epqvytlppsreemtknqvsltclvkgfypsdiavewesngqp<br>ennykttppvldsdgsfflysklltvdksrwqqgnvfscsvmhe<br>alhnhytqkslslspgkLGGGGSGGGGSGGGGSPGQGTQSENS<br>CTHFPGNLPNMLRDLRDAFSRVKTFFQMKDQLDNLLLKESLLE<br>DFKGYLGCQALSEMIQFYLEEVMPQAENQDPDIKAHVNSLGEN<br>LKTLRLRLRRCHRFLPCENKSKAVEQVKNAFNKLQEKGIYKAM<br>SEFDIFINYIEAYMTMKIRN | 84 |
| | Light Chain | DIQMTQSPSSLSASVGDRVTITCRASQDVSSGVAWYQQKPGKA<br>PKLLISFANYLYSGVPSRFSGSGSGTDFTLTISSLQPEDFATY<br>YCQQGSNLPFTFGQGTKVEIKrtvaapsvfifppsdeqlksgt<br>asvvcllnnfypreakvqwkvdnalqsgnsqesvteqdskdst<br>yslsstltlskadyekhkvyacevthqglsspvtksfnrgec | 151 |
| PHS219/IL10 | Heavy Chain | EVQLVESGGGLVQPGGSLRLSCAASGFTISNSFIHWVRQAPGK<br>GLEWVADISPYSGYTNYADSVKGRFTISADTSKNTAYLQMNSL<br>RAEDTAVYYCARTPAWGYMDYWGQGTLVTVSSastkgpsvfpla<br>psskstsggtaalgclvkdyfpepvtvswnsgaltsgvhtfpa<br>vlqssglyslssvvtvpssslgtqtyicnvnhkpsntkvdkkv<br>epkscdkthtcppcpapellggpsvflfppkpkdtlmisrtpe<br>vtcvvvdvshedpevkfnwyvdgvevhnaktkpreeqyastyr<br>vvsvltvlhqdwlngkeykckvsnkalpapiektiskakgqpr<br>epqvytlppsreemtknqvsltclvkgfypsdiavewesngqp<br>ennykttppvldsdgsfflysklltvdksrwqqgnvfscsvmhe<br>alhnhytqkslslspgkLGGGGSGGGGSGGGGSPGQGTQSENS<br>CTHFPGNLPNMLRDLRDAFSRVKTFFQMKDQLDNLLLKESLLE<br>DFKGYLGCQALSEMIQFYLEEVMPQAENQDPDIKAHVNSLGEN<br>LKTLRLRLRRCHRFLPCENKSKAVEQVKNAFNKLQEKGIYKAM<br>SEFDIFINYIEAYMTMKIRN | 85 |
| | Light Chain | DIQMTQSPSSLSASVGDRVTITCRASQDVSSSVAWYQQKPGKA<br>QKLLISWATSLYSGVPSRFSGSGSGTDFTLTISSLQPEDFATY<br>YCQQYNNFPYTFGQGTKVEIKrtvaapsvfifppsdeqlksgt<br>asvvcllnnfypreakvqwkvdnalqsgnsqesvteqdskdst<br>yslsstltlskadyekhkvyacevthqglsspvtksfnrgec | 153 |
| PHS102.HSYPP31F/<br>IL10 | Heavy Chain | EVQLVESGGGLVQPGGSLRLSCAASGFTIEDSYIHWVRQAPGK<br>GLEWVARIDPITGLTHYADSVKGRFTISADTSKNTAYLQMNSL<br>RAEDTAVYYCARAFSWFPDYWGQGTLVTVSSastkgpsvfpla<br>psskstsggtaalgclvkdyfpepvtvswnsgaltsgvhtfpa<br>vlqssglyslssvvtvpssslgtqtyicnvnhkpsntkvdkkv<br>epkscdkthtcppcpapellggpsvflfppkpkdtlmisrtpe<br>vtcvvvdvshedpevkfnwyvdgvevhnaktkpreeqyastyr<br>vvsvltvlhqdwlngkeykckvsnkalpapiektiskakgqpr<br>epqvytlppsreemtknqvsltclvkgfypsdiavewesngqp<br>ennykttppvldsdgsfflysklltvdksrwqqgnvfscsvmhe<br>alhnhytqkslslspgkLGGGGSGGGGSGGGGSPGQGTQSENS<br>CTHFPGNLPNMLRDLRDAFSRVKTFFQMKDQLDNLLLKESLLE<br>DFKGYLGCQALSEMIQFYLEEVMPQAENQDPDIKAHVNSLGEN<br>LKTLRLRLRRCHRFLPCENKSKAVEQVKNAFNKLQEKGIYKAM<br>SEFDIFINYIEAYMTMKIRN | 133 |
| | Light Chain | DIQMTQSPSSLSASVGDRVTITCRAGQDVYKAVAWYQQKPGKA<br>PKLLIYWSTNLYSGVPSRFSGSGSGTDFTLTISSLQPEDFATY<br>YCQQIMEPPVTFGQGTKVEIKrtvaapsvfifppsdeqlksgt<br>asvvcllnnfypreakvqwkvdnalqsgnsqesvteqdskdst<br>yslsstltlskadyekhkvyacevthqglsspvtksfnrgec | 134 |

TABLE 3-continued

Anti-PD-L1 antibody (including antibody fusion) sequences

| Protein Name | Description | Sequence | SEQ ID NO: |
|---|---|---|---|
| PHS102.HSYPP411C/ IL10 | Heavy Chain | EVQLVESGGGLVQPGGSLRLSCAASGFTIDNTYIHWVRQAPGK GLEWVARIDPANGKTTYADSVKGRFTISADTSKNTANLQMNSL RAEDTAVYYCARSFSWWADYWGQGTLVTVSSastkgpsvfpla psskstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsreemtknqvsltclvkgfypsdiavewesngqp ennykttppvldsdgsfflysklvtdksrwqqgnvfscsvmhe alhnhytqkslslspgk_LGGGGSGGGGSGGGGS_SPGQGTQSENS CTHFPGNLPNMLRDLRDAFSRVKTFFQMKDQLDNLLLKESLLE DFKGYLGCQALSEMIQFYLEEVMPQAENQDPDIKAHVNSLGEN LKTLRLRLRRCHRFLPCENKSKAVEQVKNAFNKLQEK | 135 |
| | Light Chain | DIQMTQSPSSLSASVGDRVTITCRAGQDVYKAVAWYQQKPGKA PKLLIYWSTNLYSGVPSRFSGSGSGTDFTLTISSLQPEDFATY YCQQFNLQPTTFGQGTKVEIKrtvaapsvfifppsdeqlksgt asvvcllnnfypreakvqwkvdnalqsgnsqesvteqdskdst yslsstltlskadyekhkvyacevthqglsspvtksfnrgec | 136 |
| PHS102.YP7G/IL10 | Heavy Chain | EVQLVESGGGLVQPGGSLRLSCAASGFTIDDTYIHWVRQAPGK GLEWVARIDPANGMTRYADSVKGRFMISADTSKNTAYLQMNSL RAEDTAVYYCARAFSWFPDYWGQGTLVTVSSastkgpsvfpla psskstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsteemtknqvsltclvkgfypsdiavewesngqp ennykttppvldsdgsfflysklvtdksrwqqgnvfscsvmhe alhnhytqkslslspgk_LGGGGSGGGGSGGGGS_SPGQGTQSENS CTHFPGNLPNMLRDLRDAFSRVKTFFQMKDQLDNLLLKESLLE DFKGYLGCQALSEMIQFYLEEVMPQAENQDPDIKAHVNSLGEN LKTLRLRLRRCHRFLPCENKSKAVEQVKNAFNKLQEKGIYKAM SEFDIFINYIEAYMTMKIRN | 141 |
| | Light Chain | DIQMTQSPSSLSASVGDRVTITCRAGQDVYKAVAWYQQKPGKA PKLLIYWSTNLYSGVPSRFSGSGSGTDFTLTISSLQPEDFATY YCQQGSTWPLTFGQGTKVEIKrtvaapsvfifppsdeqlksgt asvvcllnnfypreakvqwkvdnalqsgnsqesvteqdskdst yslsstltlskadyekhkvyacevthqglsspvtksfnrgec | 142 |
| PHS102.YP11F/IL10 | Heavy Chain | EVQLVESGGGLVQPGGSLRLSCAASGFTIDNTYIHWVRQAPGK GLEWVARIDPVSGRTRYADSVKGRFTISADTSKNTADLQMNSL RAEDTAVYYCARAFSWFPDYWGQGTLVTVSSastkgpsvfpla psskstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsreemtknqvsltclvkgfypsdiavewesngqp ennykttppvldsdgsfflysklvtdksrwqqgnvfscsvmhe alhnhytqkslslspgk_LGGGGSGGGGSGGGGS_SPGQGTQSENS CTHFPGNLPNMLRDLRDAFSRVKTFFQMKDQLDNLLLKESLLE DFKGYLGCQALSEMIQFYLEEVMPQAENQDPDIKAHVNSLGEN LKTLRLRLRRCHRFLPCENKSKAVEQVKNAFNKLQEKGIYKAM SEFDIFINYIEAYMTMKIRN | 129 |
| | Light Chain | DIQMTQSPSSLSASVGDRVTITCRAGQDVYKAVAWYQQKPGKA PKLLIYWSTNLYSGVPSRFSGSGSGTDFTLTISSLQPEDFATY YCQQFGATPITFGQGTKVEIKrtvaapsvfifppsdeqlksgt asvvcllnnfypreakvqwkvdnalqsgnsqesvteqdskdst yslsstltlskadyekhkvyacevthqglsspvtksfnrgec | 130 |
| PHS102.YT6D/IL10 | Heavy Chain | EVQLVESGGGLVQPGGSLRLSCAASGFTISDGYIHWVRQAPGK GLEWVARIDPLTGRTMYADSVKGRFTISADTSKNTAYLQMNSL RAEDTAVYYCARAFSWWPDYWGQGTLVTVSSastkgpsvfpla psskstsggtaalgclvkdyfpepvtvswnsgaltsgvhtfpa vlqssglyslssvvtvpssslgtqtyicnvnhkpsntkvdkkv epkscdkthtcppcpapellggpsvflfppkpkdtlmisrtpe vtcvvvdvshedpevkfnwyvdgvevhnaktkpreeqyastyr vvsvltvlhqdwlngkeykckvsnkalpapiektiskakgqpr epqvytlppsreemtknqvsltclvkgfypsdiavewesngqp ennykttppvldsdgsfflysklvtdksrwqqgnvfscsvmhe alhnhytqkslslspgk_LGGGGSGGGGSGGGGS_SPGQGTQSENS CTHFPGNLPNMLRDLRDAFSRVKTFFQMKDQLDNLLLKESLLE | 127 |

TABLE 3-continued

Anti-PD-L1 antibody (including antibody fusion) sequences

| Protein Name | Description | Sequence | SEQ ID NO: |
|---|---|---|---|
| | | DFKGYLGCQALSEMIQFYLEEVMPQAENQDPDIKAHVNSLGEN<br>LKTLRLRLRRCHRFLPCENKSKAVEQVKNAFNKLQEKGIYKAM<br>SEFDIFINYIEAYMTMKIRN | |
| | Light Chain | DIQMTQSPSSLSASVGDRVTITCRAGQDVYKAVAWYQQKPGKA<br>PKLLIYWSTNLYSGVPSRFSGSGSGTDFTLTISSLQPEDFATY<br>YCQQIMSPPPTFGQGTKVEIKrtvaapsvfifppsdeqlksgt<br>asvvcllnnfypreakvqwkvdnalqsgnsqesvteqdskdst<br>yslsstltlskadyekhkvyacevthqglsspvtksfnrgec | 128 |
| PHS102.YT7A/IL10 | Heavy Chain | EVQLVESGGGLVQPGGSLRLSCAASGFTIDNTYIHWVRQAPGK<br>RLEWVARIDPANGVTRYADSVKGRFTISADTSKNTAYLQMNSL<br>RAEDTAVYYCARAFSWFPDYWGQGTLVTVSSastkgpsvfpla<br>psskstsggtaalgclvkdyfpepvtvswnsgaltsgvhtfpa<br>vlqssglyslssvvtvpssslgtqtyicnvnhkpsntkvdkkv<br>epkscdkthtcppcpapellggpsvflfppkpkdtlmisrtpe<br>vtcvvvdvshedpevkfnwyvdgvevhnaktkpreeqyastyr<br>vvsvltvlhqdwlngkeykckvsnkalpapiektiskakgqpr<br>epqvytlppsreemtknqvsltclvkgfypsdiavewesngqp<br>ennykttppvldsdgsfflysklvtvdksrwqqgnvfscsvmhe<br>alhnhytqkslslspgk_LGGGGSGGGGSGGGGS_SPGQGTQSENS<br>CTHFPGNLPNMLRDLRDAFSRVKTFFQMKDQLDNLLLKESLLE<br>DFKGYLGCQALSEMIQFYLEEVMPQAENQDPDIKAHVNSLGEN<br>LKTLRLRLRRCHRFLPCENKSKAVEQVKNAFNKLQEKGIYKAM<br>SEFDIFINYIEAYMTMKIRN | 137 |
| | Light Chain | DIQMTQSPSSLSASVGDRVTITCRAGQDVYKAVAWYQQKPGKA<br>PKLLIYWSTNLYSGVPSRFSGSGSGTDFTLTISSLQPEDFATY<br>YCQQYGIAPPTFGQGTKVEIKrtvaapsvfifppsdeqlksgt<br>asvvcllnnfypreakvqwkvdnalqsgnsqesvteqdskdst<br>yslsstltlskadyekhkvyacevthqglsspvtksfnrgec | 138 |
| PHS102.YT7H/IL10 | Heavy Chain | EVQLVESGGGLVQPGGSLRLSCAASGFTITDGYIHWVRQAPGK<br>GLEWVARIDPYNGRTNYADSVKGRFTISADTSKNTAYLQMNSL<br>RAEDTAVYYCARAFSWFPDYWGQGTLVTVSSastkgpsvfpla<br>psskstsggtaalgclvkdyfpepvtvswnsgaltsgvhtfpa<br>vlqssglyslssvvtvpssslgtqtyicnvnhkpsntkvdkkv<br>epkscdkthtcppcpapellggpsvflfppkpkdtlmisrtpe<br>vtcvvvdvshedpevkfnwyvdgvevhnaktkpreeqyastyr<br>vvsvltvlhqdwlngkeykckvsnkalpapiektiskakgqpr<br>epqvytlppsreemtknqvsltclvkgfypsdiavewesngqp<br>ennykttppvldsdgsfflysklvtvdksrwqqgnvfscsvmhe<br>alhnhytqkslslspgk_LGGGGSGGGGSGGGGS_SPGQGTQSENS<br>CTHFPGNLPNMLRDLRDAFSRVKTFFQMKDQLDNLLLKESLLE<br>DFKGYLGCQALSEMIQFYLEEVMPQAENQDPDIKAHVNSLGEN<br>LKTLRLRLRRCHRFLPCENKSKAVEQVKNAFNKLQEKGIYKAM<br>SEFDIFINYIEAYMTMKIRN | 139 |
| | Light Chain | DIQMTQSPSSLSASVGDRVTITCRAGQDVYKAVAWYQQKPGKA<br>PKLLIYWSTNLYSGVPSRFSGSGSGTDFTLTISSLQPEDFATY<br>YCQQHGNAPITFGQGTKVEIKrtvaapsvfifppsdeqlksgt<br>asvvcllnnfypreakvqwkvdnalqsgnsqesvteqdskdst<br>yslsstltlskadyekhkvyacevthqglsspvtksfnrgec | 140 |
| PHS102.YT10H/IL10 | Heavy Chain | EVQLVESGGGLVQPGGSLRLSCAASGFTISDAYIHWVRQAPGK<br>GLEWVARIEPLSGRTDYADSVKGRFTISADTSKNTAYLQMNSL<br>RAEDTAVYYCARAFSWFMDYWGQGTLVTVSSastkgpsvfpla<br>psskstsggtaalgclvkdyfpepvtvswnsgaltsgvhtfpa<br>vlqssglyslssvvtvpssslgtqtyicnvnhkpsntkvdkkv<br>epkscdkthtcppcpapellggpsvflfppkpkdtlmisrtpe<br>vtcvvvdvshedpevkfnwyvdgvevhnaktkpreeqyastyr<br>vvsvltvlhqdwlngkeykckvsnkalpapiektiskakgqpr<br>epqvytlppsreemtknqvsltclvkgfypsdiavewesngqp<br>ennykttppvldsdgsfflysklvtvdksrwqqgnvfscsvmhe<br>alhnhytqkslslspgk_LGGGGSGGGGSGGGGS_SPGQGTQSENS<br>CTHFPGNLPNMLRDLRDAFSRVKTFFQMKDQLDNLLLKESLLE<br>DFKGYLGCQALSEMIQFYLEEVMPQAENQDPDIKAHVNSLGEN<br>LKTLRLRLRRCHRFLPCENKSKAVEQVKNAFNKLQEKGIYKAM<br>SEFDIFINYIEAYMTMKIRN | 131 |

TABLE 3-continued

Anti-PD-L1 antibody (including antibody fusion) sequences

| Protein Name | Description | Sequence | SEQ ID NO: |
|---|---|---|---|
| | Light Chain | DIQMTQSPSSLSASVGDRVTITCRAGQDVYKAVAWYQQKPGKA PKLLIYWSTNLYSGVPSRFSGSGSGTDFTLMISSLQPEDFATY YCQQHDKTPTTFGQGTKVEIKrtvaapsvfifppsdeqlksgt asvvcllnnfypreakvqwkvdnalqsgnsqesvteqdskdst yslsstltlskadyekhkvyacevthqglsspvtksfnrgec | 132 |

Variable domain: UPPERCASE
Constant domain: lower case
Linker: *UPPERCASE ITALICS*
IL-10: UPPERCASE UNDERLINED
human IgG1 Fc fragment: Bold lower case

1. Anti-PD-L1 Antibody Binding Affinity and Functional Characteristics

In some embodiments, the anti-PD-L1 antibodies provided herein have an equilibrium dissociation constant ($K_D$) for binding to PD-L1 of <100 nM, <10 nM, <1 nM, <0.1 nM, <0.01 nM, or <0.001 nM (e.g., $10^{-8}$ M or less, from $10^{-8}$ M to $10^{-13}$ M, e.g., from $10^{-9}$ M to $10^{-13}$ M).

It is contemplated that the various anti-PD-L1 antibodies generated as disclosed herein include antibodies capable of high-affinity binding to huPD-L1, cynoPD-L1, and both huPD-L1 and cynoPD-L1. More specifically, in some embodiments, the anti-PD-L1 antibodies of the present disclosure bind to huPD-L1 with a binding affinity of $1 \times 10^{-8}$ M or less, $1 \times 10^{-9}$ M or less, $1 \times 10^{-10}$ M or less, or $1 \times 10^{-11}$ M or less. In some embodiments, the binding affinity is measured as the equilibrium dissociation constant ($K_D$) for binding to the huPD-L1 polypeptide of SEQ ID NO: 174. In some embodiments, the anti-PD-L1 antibodies of the present disclosure bind to cynoPD-L1 with a binding affinity of $1 \times 10^{-8}$ M or less, $1 \times 10^{-9}$ M or less, $1 \times 10^{-10}$ M or less, or $1 \times 10^{-11}$ M or less. In some embodiments, the binding affinity is measured as the equilibrium dissociation constant ($K_D$) for binding to the cynoPD-L1 polypeptide of SEQ ID NO: 176. In some embodiments, the anti-PD-L1 antibodies of the present disclosure bind to both huPD-L1 and cynoPD-L1 with a binding affinity of $1 \times 10^{-8}$ M or less, $1 \times 10^{-9}$ M or less, $1 \times 10^{-10}$ M or less, or $1 \times 10^{-11}$ M or less. In some embodiments, the binding affinity is measured as the equilibrium dissociation constant ($K_D$) for binding to the huPD-L1 polypeptide of SEQ ID NO: 174 and the cynoPD-L1 polypeptide of SEQ ID NO: 176.

Generally, binding affinity of a ligand to its receptor can be determined using any of a variety of assays and expressed in terms of a variety of quantitative values. Specific PD-L1 binding assays useful in determining affinity of the antibodies are disclosed in the Examples herein. Additionally, antigen binding assays are known in the art and can be used herein including without limitation any direct or competitive binding assays using techniques such as western blots, radioimmunoassays, enzyme-linked immunoabsorbent assay (ELISA), "sandwich" immunoassays, surface plasmon resonance based assay (such as the BIAcore assay as described in WO2005/012359), immunoprecipitation assays, fluorescent immunoassays, protein A immunoassays, flow cytometric and fluorescence activated cell sorting (FACS) assays, and the like.

Accordingly, in some embodiments, the binding affinity is expressed as $K_D$ values and reflects intrinsic binding affinity (e.g., with minimized avidity effects). The anti-PD-L1 antibodies of the present disclosure exhibit strong binding affinities for the huPD-L1 polypeptide of SEQ ID NO: 174, for example, exhibiting $K_D$ values of between 10 nM and 1 pM. Accordingly, anti-PD-L1 antibodies of the present disclosure may compete with antibodies having lower affinity for the same or overlapping epitopes of PD-L1.

In some embodiments, the anti-PD-L1 antibodies provided herein decrease, inhibit, and/or fully-block PD1 binding to PD-L1, and immune regulation and/or immune signaling mediated by PD1 binding to PD-L1, including the suppression of T-cell activity in the tumor microenvironment (TME). The ability of the antibodies to inhibit these immune regulatory and immune signaling pathways mediated by PD1 binding to PD-L1 can be assayed in vitro using known cell-based assays including those assays described in the Examples of the present disclosure.

Additionally, the anti-PD-L1 antibodies provided herein comprise antibody fusions with IL10, and accordingly can provide effects mediated by IL10 agonist activity including activating. CD8+ T-cells in the tumor microenvironment. The ability of the anti-PD-L1 antibody fusions with IL10 to provide IL10 agonist effects can be assayed in vitro using known cell-based assays including those cell-based assays described in the Examples of the present disclosure.

Accordingly, in some embodiments, the PD-L1 antibodies of the present disclosure are characterized by one or more of following functional properties based on the ability to decrease, inhibit, and/or fully-block intracellular signaling by PD-L1-mediated pathways.

In at least one embodiment, the anti-PD-L1 antibody binds to human PD-L1 with a binding affinity of $1 \times 10^{-8}$ M or less, $1 \times 10^{-9}$ M or less, $1 \times 10^{-10}$ M or less; optionally, wherein the binding affinity is measured by equilibrium dissociation constant ($K_D$) to a huPD-L1 polypeptide of SEQ ID NO: 174.

In at least one embodiment, the anti-PD-L1 antibody, the antibody binds to cynomolgus PD-L1 with a binding affinity of $1 \times 10^{-8}$ M or less, $1 \times 10^{-9}$ M or less, $1 \times 10^{-10}$ M or less; optionally, wherein the binding affinity is measured by equilibrium dissociation constant ($K_D$) to a cynoPD-L1 polypeptide of SEQ ID NO: 176.

In at least one embodiment, the anti-PD-L1/IL10 fusion protein, the protein increases MC/9 cell proliferation by at least 25%, at least 50%, at least 100%, at least 150%, at least 200% or more.

In at least one embodiment, the anti-PD-L1/IL10 fusion protein, the protein increases IFNγ and granzyme B production from activated CD8 T cells by at least 25%, at least 50%, at least 100%, or more.

In at least one embodiment, the anti-PD-L1 antibody, the antibody decreases tumor volume in a syngeneic mouse tumor model measured at 28 days by at least 25%, at least 50%, at least 75%, or more, wherein the mouse tumor model is selected from: CT26 colon cancer and EMT6 breast cancer.

2. Anti-PD-L1 Antibody Fragments

In some embodiments, the anti-PD-L1 antibody of the present disclosure can be an antibody fragment. Antibody fragments useful with the binding determinants the present disclosure include, but are not limited to, Fab, Fab', Fab'-SH, F(ab')$_2$, Fv, scFv fragments, monovalent, single domain antibody, one-armed or single-arm antibody, and other fragments described herein and known in the art. Accordingly, in some embodiments of the anti-PD-L1 antibodies of the present disclosure, the antibody is an antibody fragment selected from the group consisting of F(ab')$_2$, Fab', Fab, Fv, single domain antibody (VHH), single-arm antibody, and scFv.

For a review of various antibody fragments, see e.g., Hudson et al. Nat. Med. 9: 129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO93/16185; and U.S. Pat. Nos. 5,571,894 and 5,587,458. For a description of Fab and F(ab')$_2$ fragments comprising salvage receptor binding epitope residues and having increased in vivo half-life, see U.S. Pat. No. 5,869,046. Other monovalent antibody forms are described in, e.g., WO2007/048037, WO2008/145137, WO2008/145138, and WO2007/059782. Monovalent, single-armed antibodies are described, e.g., in WO2005/063816. Diabodies are antibody fragments with two antigen-binding sites that may be bivalent or bispecific (see e.g., EP0404097; WO93/01161; Hudson et al., Nat. Med. 9. 129-134 (2003); and Hollinger et al., Proc. Natl. Acad. Sci. USA 90: 6444-6448 (1993)).

In some embodiments, the antibody fragments are single-domain antibodies which comprise all or a portion of the heavy chain variable domain or all or a portion of the light chain variable domain of an antibody. In some embodiments, a single-domain antibody is a human single-domain antibody (Domantis, Inc., Waltham, MA; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

3. Chimeric, Humanized, and Human Anti-PD-L1 Antibodies

In some embodiments, the anti-PD-L1 antibody of the present disclosure can be a chimeric antibody. (See e.g., chimeric antibodies as described in U.S. Pat. No. 4,816,567; and Morrison et al., Proc. Natl. Acad. Sci. USA, 81:6851-6855 (1984)). In one embodiment, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched: antibody in which the class or subclass has been changed from that of the parent antibody. It is contemplated that chimeric antibodies can include antigen-binding fragments thereof.

In some embodiments, the anti-PD-L1 antibody of the present disclosure is a humanized antibody. Typically, a non-human antibody is humanized to reduce immunogenicity to humans, while retaining the specificity and affinity of the parental non-human antibody. Generally, a humanized antibody comprises one or more variable domains in which HVRs, CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived) to restore or improve antibody specificity or affinity.

Humanized antibodies and methods of making them are reviewed, e.g., in Almagro and Fransson, Front. Biosci. 13: 1619-1633 (2008), and are further described, e.g., in Riechmann et al., Nature 332:323-329 (1988); Queen et al., Proc. Nat'l Acad. Sci. USA 86: 10029-10033 (1989); U.S. Pat. Nos. 5,821,337, 7,527,791, 6,982,321, and 7,087,409; Kashmiri et al, Methods 36:25-34 (2005) (describing SDR (a-HVR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13: 1619-1633 (2008)); and framework regions derived from screening FR libraries (see, e.g., Baca et al., J. Biol. Chem. 272: 10678-10684 (1997) and Rosok et al., J. Biol. Chem. 271:22611-22618 (1996)).

In some embodiments, the anti-PD-L1 antibody of the present disclosure can be a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., XENOMOUSE™ technology in U.S. Pat. Nos. 6,075,181 and 6,150,584; HUMAB® technology in U.S. Pat. No. 5,770,429; K-M MOUSE® technology in U.S. Pat. No. 7,041,870; and VELOCIMOUSE® technology in U.S. Pat. Appl. Pub. No. US 2007/0061900). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. See, e.g., Kozbor J. Immunol, 133:3001 (1984); Brodeur et al., Monoclonal Antibody Production Techniques and Applications, pp. 51-63 (Marcel Dekker, Inc., New York, 1987); and Boerner et al., J. Immunol., 147: 86 (1991). Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Variants of Anti-PD-L1 Antibodies

In at least one embodiment, improved variants of anti-PD-L1 antibodies may be isolated by screening combinatorial libraries for antibodies with the desired improved functional characteristic, such as binding affinity or cross-reactivity. For example, a variety of methods are known in the art for generating phage display libraries and screening such libraries for variant antibodies possessing the improved binding characteristics. Other methods for producing such library-derived antibodies can be found in e.g., Hoogenboom et al., Methods in Molecular Biology 178: 1-37 (O'Brien et al., ed., Human Press, Totowa, NJ, 2001); McCafferty et al., Nature 348:552-554; Clackson et al., Nature 352: 624-628 (1991); Marks et al., Mol. Biol. 222: 581-597 (1992); Marks and Bradbury, m Methods in Molecular Biology 248: 161-175 (Lo, ed., Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

5. Multispecific Antibodies and Antibody Fusions

In at least one embodiment, it is contemplated that an anti-PD-L1 antibody of the present disclosure can be a multispecific antibody, e.g., a bispecific antibody. In some embodiments, the multispecific antibody has at least two different binding sites, each with a binding specificity for a different antigen, at least one of which specifically binds PD-L1. In at least one embodiment, it is contemplated that the multispecific antibody is a bispecific antibody comprising a specificity for PD-L1 and a specificity for another antigen that mediates immune regulation, immune signaling, and/or is expressed on a cancer or tumor cell. For example, the other specificity could be for an immune checkpoint molecule, such as PD1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, or ICOS.

Techniques for making multispecific antibodies include, but are not limited to, recombinant co-expression of two immunoglobulin heavy chain-light chain pairs having different specificities (see e.g., Milstein and Cuello, *Nature* 305: 537 (1983), WO 93/08829, and Traunecker et al., EMBOJ. 10: 3655 (1991)). "Knob-in-hole" engineering can also be used to generate bispecific antibodies useful with the anti-PD-L1 antibodies of the present disclosure. Techniques for knob-in-hole engineering are known in the art and described in e.g., U.S. Pat. No. 5,731,168.

Multispecific antibodies can also be made by engineering "electrostatic steering" effects that favor formation of Fc-heterodimeric antibody molecules rather than homodimers (WO 2009/089004A1); cross-linking two or more antibodies or fragments (see, e.g., U.S. Pat. No. 4,676,980, and Brennan et al., Science, 229: 81 (1985)); using leucine zippers to produce bispecific antibodies (see, e.g., Kostelny et al., J. Immunol, 148(5): 1547-1553 (1992)); using "diabody" technology for making bispecific antibody fragments (see, e.g., Hollinger et al., Proc. Natl. Acad. Sci. USA, 90:6444-6448 (1993)); using single-chain Fv (scFv) dimers (see, e.g. Gruber et al., J. Immunol, 152:5368 (1994)); or tri-specific antibodies (see e.g., Tutt et al., J. Immunol. 147: 60 (1991).

In at least one embodiment, the anti-PD-L1 antibodies provided herein can comprise an antibody fusion with a protein. Methods for preparation and use of antibody fusions or fusion proteins are well known in the art, and are described elsewhere herein including the Examples. Typically, the antibody is covalently conjugated (or fused) through a polypeptide linker (comprising a chain of 5-30 amino acids) to the protein. Typically, the linker is conjugated to the C-terminus of the antibody's heavy chain (HC) constant region, however, conjugation through the N-terminus, or to either terminus of the antibody's light chain (LC) can also be used. Antibody fusions also can be prepared with various antibody fragments, where the fragments comprise the CDRs required for specific binding to an antigen.

In at least one embodiment, an antibody fusion of the present disclosure can include a full length anti-PD-L1 antibody conjugated at a light or heavy chain terminus to a polypeptide linker sequence which is conjugated at its other end to a T-cell activating or immunostimulatory cytokine. The cytokine can include, but is not limited to, IL2, IL7, IL10, IL12, IL15, IL21, or IFN-α. Such an anti-PD-L1 antibody fusion can block activity mediated by PD-L1/PD1 signaling and provide an immunostimulatory cytokine effect. The ability of such an anti-PD-L1/cytokine antibody fusion to provide an immunostimulatory cytokine effects can be assayed in vitro using known cell-based assays associated with the cytokine, including those described in the Examples.

As described elsewhere herein, an antibody fusion of the present disclosure can include a full-length IgG antibody, comprising a dimeric complex of heavy chain-light chain pairs, where each heavy chain C-terminus is linked through a polypeptide linker sequence to an IL10 polypeptide. In one exemplary embodiment, an antibody fusions of the present disclosure can include an anti-PD-L1 antibody fused to a recombinant IL10 polypeptide via a 15 amino acid polypeptide linker (e.g., SEQ ID NO: 74) from the C-terminus of the antibody heavy chain to the N-terminus of the IL10 polypeptide. A number of such exemplary anti-PD-L1/IL10 antibody fusions are further described and characterized for their PD-L1 binding, and immunostimulatory IL10 effects in the Examples.

6. Variants of Anti-PD-L1 Antibodies

In some embodiments, variants of the anti-PD-L1 antibodies of the present disclosure are contemplated having improved characteristics such as binding affinity and/or other biological properties of the antibody. Variants can be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristic of PD-L1 antigen binding.

A. Substitution, Insertion, and Deletion Variants

In some embodiments, anti-PD-L1 antibody variants having one or more amino acid substitutions in addition to those described herein are provided. Sites for mutagenesis can include the HVRs and FRs. Typical "conservative" amino acid substitutions and/or substitutions based on common side-chain class or properties are well-known in the art and can be used in the embodiments of the present disclosure. The present disclosure also contemplates variants based on non-conservative amino acid substitutions in which a member of one of amino acid side chain class is exchanged for an amino acid from another class. Amino acid side chains are typically grouped according to the following classes or common properties: (1) hydrophobic: Met, Ala, Val, Len, Ile, Norleucine; (2) neutral hydrophilic: Cys, Ser, Thr, Asn, Gln: (3) acidic: Asp, Glu; (4) basic: His, Lys, Arg; (5) chain orientation influencing: Gly, Pro; and (6) aromatic: Trp, Tyr, Phe. Techniques are well-known in the art for amino acid substitution into an antibody and subsequent screening for desired function, e.g., retained/improved antigen binding, decreased immunogenicity, or improved ADCC or CDC.

Amino acid substitution variants can also include variants having one or more substitutions in hypervariable regions of a parent antibody. Generally, the resulting variant(s) selected for further study will have modifications of certain biological properties (e.g., increased affinity, reduced immunogenicity) relative to the parent antibody and/or will retain certain biological properties of the parent antibody. An exemplary substitutional variant is an affinity matured antibody, which may be conveniently generated, using phage display-based affinity maturation techniques. Briefly, one or more HVR residues are mutated and the variant antibodies displayed on phage and screened for a particular biological activity (e.g., binding affinity).

One useful method for identifying residues or regions of an antibody that may be targeted for mutagenesis is "alanine scanning mutagenesis" (see e.g., Cunningham and Wells (1989) Science, 244: 1081-1085). In this method, a residue or group of target residues (e.g., charged residues such as Arg, Asp, His, Lys, and Glu) are identified and replaced by a neutral or negatively charged amino acid (e.g., Ala or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen can be determined. Such contact residues and neighboring residues may be targeted or eliminated as candidates for substitution. Variants may be screened to determine whether they contain the desired properties.

Amino acid sequence insertions which can be prepared include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue. Other insertional variants of the antibody molecule can include a fusion of the N- or C-terminus of the antibody to an enzyme or a polypeptide which increases antibody serum half-life.

Other residue substitutions can be made in HVRs to improve antibody affinity. Such alterations may be made in "hotspots," i.e., residues encoded by codons that undergo mutation at high frequency during the somatic maturation process (see, e.g., Chowdhury, Methods Mol. Biol. 207: 179-196 (2008)) with the resulting variant $V_H$ or $V_L$ being tested for binding affinity. In one embodiment, affinity maturation can be carried out by constructing and reselecting from secondary libraries (see e.g., in Hoogenboom et al., Methods in Molecular Biology 178: 1-37 (O'Brien et al., ed., Human Press, Totowa, NJ, (2001).) Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted. Generally, substitutions, insertions, or deletions can be made within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots."

In some embodiments, it is contemplated that the anti-PD-L1 antibody described herein can be substituted at specific non-HVR positions with cysteine residues so as to create reactive thiol groups. Such engineered "thioMAbs" can be used to conjugate the antibody to e.g., drug moieties or linker-drug moieties and thereby create immunoconjugates, as described elsewhere herein. Cysteine engineered antibodies can be generated as described in e.g., U.S. Pat. No. 7,521,541. In some embodiments, any one or more of the following antibody residues can be substituted with cysteine: V205 (Kabat numbering) of the light chain; A118 (EU numbering) of the heavy chain; and S400 (EU numbering) of the heavy chain Fc region.

B. Glycosylation Variants

In some embodiments, the anti-PD-L1 antibody of the present disclosure is altered to increase or decrease the extent to which the antibody is glycosylated. Addition or deletion of glycosylation sites to an antibody can be carried out by altering the amino acid sequence such that one or more glycosylation sites is created or removed. In embodiments where the antibody comprises an Fc region, the carbohydrate attached to the Fc region can be altered. Typically, native antibodies produced by mammalian cells comprise a branched, biantennary oligosaccharide attached by an N-linkage to the asparagine at about position 297 ("N297") of the CH2 domain of the Fc region (see, e.g., Wright et al. TIBTECH 15:26-32 (1997)). The oligosaccharide may include various carbohydrates, such as mannose, N-acetyl glucosamine (GlcNAc), galactose, and sialic acid, as well as, a fucose attached to a GlcNAc in the "stem" of the bi-antennary oligosaccharide structure. In some embodiments, the modifications of the oligosaccharide of an Fc region of an antibody can create a variant with certain improved properties.

In some embodiments, the anti-PD-L1 antibody of the present disclosure can be a variant comprising a carbohydrate structure that lacks fucose attached (directly or indirectly) to an Fc region. For example, the amount of fucose in such antibody may be from about 1% to about 80%, from about 1% to about 65%, from about 5% to about 65%, or from about 20% to about 40%. The amount of fucose can be determined by calculating the average amount of fucose within the sugar chain attached to residue N297, relative to the sum of all glyco-structures attached at N297 (e.g., complex, hybrid and high mannose structures) as measured by MALDI-TOF mass spectrometry (see e.g., WO 2008/077546).

In some embodiments, the fucosylation variants can provide improved ADCC function of the variant antibody. See, e.g., US Patent Publication Nos. US 2003/0157108, or US 2004/0093621. Examples of "defucosylated" or "fucose-deficient" antibodies and associated methods for preparing them are disclosed in e.g., US2003/0157108; US2003/0115614; US2002/0164328; US2004/0093621; US2004/0132140; US2004/0110704; US2004/0110282; US2004/0109865; WO2000/61739; WO2001/29246; WO2003/085119; WO2003/084570; WO2005/035586; WO2005/035778; WO2005/053742; WO2002/031140; Okazaki et al. J. Mol. Biol. 336: 1239-1249 (2004); Yamane-Ohnuki et al. Biotech. Bioeng. 87: 614 (2004). Cell lines useful for producing defucosylated antibodies include Led 3 CHO cells deficient in protein fucosylation (see e.g., Ripka et al. Arch. Biochem. Biophys. 249:533-545 (1986); US2003/0157108, and WO2004/056312), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

C. Fc Region Variants

In some embodiments, an anti-PD-L1 antibody of the present disclosure can comprise one or more amino acid modifications in the Fc region (i.e., an Fc region variant). The Fc region variant may comprise a human Fc region sequence (e.g., a human IgG1, IgG2, IgG3, or IgG4 Fc region) comprising an amino acid substitution at one or more amino acid residue positions. A wide range of Fc region variants known in the art that are useful with the anti-PD-L1 antibodies of the present disclosure are described below.

In some embodiments, the anti-PD-L1 antibody is an Fc region variant which has altered effector function. In some embodiments, the antibody with altered effector function possesses some (but not all of) the effector functions, decreased effector function, or none of the effector functions (e.g., effectorless) of the parent antibody. Effectorless Fc region variants are more desirable for certain applications where effector function (such as ADCC) is unnecessary or deleterious, and/or in vivo half-life of the antibody is important. Fc region variant antibodies having reduced effector or effectorless function can result from amino acid substitution at one or more of the following Fc region positions: 238, 265, 269, 270, 297, 327 and 329. (see, e.g., U.S. Pat. No. 6,737,056). Such Fc region variants can include amino acid substitutions at two or more of positions 265, 269, 270, 297 and 327. Such Fc region variants can also include substitutions of both residues 265 and 297 to alanine (see e.g., U.S. Pat. No. 7,332,581).

Some Fc region variants are capable of providing improved or diminished binding to FcRs (see e.g., U.S. Pat. No. 6,737,056; WO 2004/056312; and Shields et al., J. Biol. Chem. 9(2): 6591-6604 (2001)). Some Fc region variants capable of providing improved ADCC comprise one or more amino acid substitutions at e.g., positions 298, 333, and/or 334 of the Fc region (based on EU numbering). Fe region variants having altered (i.e., either improved or diminished) Clq binding and/or Complement Dependent Cytotoxicity (CDC), as described in e.g., U.S. Pat. No. 6,194,551, WO99/51642, and Idusogie et al., J. Immunol. 164: 4178-4184 (2000).

Some Fc region variants are capable of providing increased half-lives and improved binding to the neonatal Fc receptor (FcRn) are disclosed in e.g., US2005/0014934A1 (Hinton et al.). Such Fc region variants comprise amino acid substitutions at one or more of positions: 238, 256, 265, 272, 286, 303, 305, 307, 311, 312, 317, 340, 356, 360, 362, 376, 378, 380, 382, 413, 424, and 434. Other Fc region variants with increased half-lives include the set of YTE mutations at positions 252, 254, and 256 (i.e., M252Y/S254T/T256E) described in e.g., U.S. Pat. No. 7,658,921B2 (Dall'Acqua et al.). Additional examples of Fc region variants can be found in e.g., U.S. Pat. Nos. 5,648,260 and 5,624,821; and WO94/29351.

Generally, in vitro and/or in vivo cytotoxicity assays can be carried out to confirm the reduction/depletion of CDC and/or ADCC activities in an Fc region variant. For example, Fc receptor (FcR) binding assays can be conducted to ensure that the antibody lacks FcγR binding (hence likely lacking ADCC activity) but retains FcRn binding ability. The primary cells for mediating ADCC, NK cells express FcγRIII only, whereas monocytes express FcγRI, FcγRII, and FcγRIII. Non-limiting examples of in vitro assays to assess ADCC activity of a molecule of interest is described in U.S. Pat. No. 5,500,362 (see, e.g. Hellstrom, et al., Proc. Nat'l Acad. Sci. USA 83:7059-7063 (1986)) and Hellstrom, et al., Proc. Nat'l Acad. Sci. USA 82: 1499-1502 (1985); U.S. Pat. No. 5,821,337 (see Bruggemann, M. et al., J. Exp. Med. 166: 1351-1361 (1987)). Alternatively, non-radioactive assay methods may be employed (see, for example, ACTI™ nonradioactive cytotoxicity assay for flow cytometry (CellTechnology, Inc. Mountain View, CA; and Cyto-Tox96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). Clq binding assays may also be carried out to confirm that the antibody is unable to bind Clq and hence lacks CDC activity. See, e.g., Clq and C3c binding ELISA in WO2006/029879 and WO2005/100402. To assess complement activation, a CDC assay may be performed (see, e.g., Gazzano-Santoro et al., J. Immunol. Methods 202: 163 (1996); Cragg, M. S. et al., Blood 101: 1045-1052 (2003); and Cragg, M. S. and M. J. Glennie, S W 103:2738-2743 (2004)). FcRn binding and in vivo clearance/half-life determinations can be performed using methods known in the art (see, e.g., Petkova, et al., Intl. Immunol. 18(12): 1759-1769 (2006)).

D. Non-Protein Antibody Derivatives—Immunoconjugates

In some embodiments, the anti-PD-L1 antibody of the present disclosure may be further modified (i.e., derivatized) with non-proteinaceous moieties. Non-proteinaceous moieties suitable for derivatization of the antibody include, but are not limited to, water soluble polymers, such as: polyethylene glycol (PEG), copolymers of ethylene glycol and propylene glycol, carboxy-methylcellulose, dextran, polyvinyl alcohol, polyvinyl pyrrolidone, poly-1,3-dioxolane, poly-1,3,6-trioxane, ethylene/maleic anhydride copolymer, poly-amino acid homo-polymers or random co-polymers, and dextran or poly(n-vinyl pyrrolidone)polyethylene glycol, propropylene glycol homo-polymers, polypropylene oxide/ethylene oxide co-polymers, polyoxy-ethylated polyols (e.g., glycerol), polyvinyl alcohol, and mixtures thereof. In some embodiments, modification of the antibody can be carried out using methoxy-polyethylene glycol propionaldehyde. The polymers may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody, e.g., whether the antibody derivative will be used in a therapy under defined conditions.

In some embodiments, the anti-PD-L1 antibody of the present disclosure can also be an immunoconjugate, wherein the immunoconjugate comprises an anti-PD-L1 antibody conjugated to one or more cytotoxic agents. Suitable cytotoxic agents contemplated by the present disclosure include chemotherapeutic agents, drugs, growth inhibitory agents, toxins (e.g., protein toxins, enzymatically active toxins of bacterial, fungal, plant, or animal origin, or fragments thereof), or radioactive isotopes. In some embodiments, the immunoconjugate is an antibody-drug conjugate (ADC) in which an anti-PD-L1 antibody, as described herein, is conjugated to one or more drugs. In some embodiments, an immunoconjugate of the present disclosure comprises an anti-PD-L1 antibody as described herein conjugated to a drug or therapeutic agent for the treatment of a PD-L1-mediated disease or condition.

In some embodiments, an anti-PD-L1 antibody as described herein can be conjugated to an enzymatically active toxin or a fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins, *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate of the present disclosure comprises an anti-PD-L1 antibody as described herein conjugated to a radioactive isotope (i.e., a radioconjugate). A variety of radioactive isotopes are available for the production of such radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb, and radioactive isotopes of Lu. In some embodiments, the immunoconjugate may comprise a radioisotope for scintigraphic detection, or a spin label for NMR detection or MRI. Suitable radioisotopes or spin labels can include, as $^{123}$I, $^{131}$I, $^{111}$In, $^{13}$C, $^{19}$F, $^{15}$N, $^{17}$O, various isotopes of Gd, Mn, and Fe.

Immunoconjugates of an anti-PD-L1 antibody and a cytotoxic agent, can be made using a variety of well-known bifunctional reagents and chemistries suitable for conjugating to proteins. Such reagents include but are not limited to: N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (e.g., dimethyl adipimidate HQ), active esters (e.g., disuccinimidyl suberate), aldehydes (e.g., glutaraldehyde), bis-azido compounds (e.g., bis-(p-azidobenzoyl)-hexanediamine), bis-diazonium derivatives (e.g., bis-(p-diazoniumbenzoyl)-ethylenediamine), diisocyanates (e.g., toluene-2,6-diisocyanate), and bis-active fluorine compounds (e.g., 1,5-difluoro-2,4-dinitrobenzene). Reagents for preparing immunoconjugates of the present disclosure can also include commercially available "cross-linking" reagents such as: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) (see e.g., Pierce Biotechnology, Inc., Rockford, IL., U.S.A).

IV. Recombinant Methods and Compositions

The anti-PD-L1 antibody of the present disclosure can be produced using recombinant methods and materials well-known in the art of antibody production. In some embodiments, the present disclosure provides an isolated nucleic acid encoding an anti-PD-L1 antibody. The nucleic acid can encode an amino acid sequence comprising the $V_L$ and/or an amino acid sequence comprising the $V_H$ of the antibody (e.g., the light and/or heavy chains of the antibody). In some embodiments, one or more vectors (e.g., expression vectors) comprising nucleic acid sequences encoding an anti-PD-L1 antibody of the present disclosure are provided. In some embodiments, a host cell comprising nucleic acid sequences encoding an anti-PD-L1 antibody of the present disclosure are provided. In one embodiment, the host cell has been transformed with a vector comprising a nucleic acid that encodes an amino acid sequence comprising the $V_L$ of the antibody and an amino acid sequence comprising the $V_H$ of the antibody. In another embodiment, the host cell has been transformed with a first vector comprising a nucleic acid that encodes an amino acid sequence comprising the $V_L$ of the antibody and a second vector comprising a nucleic acid that encodes an amino acid sequence comprising the $V_H$ of the antibody.

In some embodiments of the recombinant methods, the host cell used is a eukaryotic cell, such as a Chinese Hamster Ovary (CHO) cell, or a lymphoid cell (e.g., Y0, NS0, Sp20). In one embodiment, a method of making an anti-PD-L1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

Briefly, recombinant production of an anti-PD-L1 antibody is carried out by isolating a nucleic acid encoding an antibody (e.g., as described herein) and inserting this nucleic acid into one or more vectors for further cloning and/or expression in a host cell. Such nucleic acids are readily isolated and sequenced using conventional procedures well-known in the art (e.g., by using oligonucleotide probes that are capable of binding specifically to genes encoding the heavy and light chains of the desired antibody). Suitable host cells and culturing methods for cloning or expressing the antibody-encoding vectors are well-known in the art and include prokaryotic or eukaryotic cells. Typically, after expression, the antibody may be isolated from cell paste in a soluble fraction and further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (see e.g., Gerngross, Nat. Biotech. 22: 1409-1414 (2004), and Li et al., Nat. Biotech. 24:210-215 (2006)).

Suitable host cells for the expression of glycosylated anti-PD-L1 antibodies of the present disclosure can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (see, e.g., U.S. Pat. Nos. 5,959,177, 6,040,498, 6,420,548, and 7,125,978.

Examples of mammalian host cell lines useful for the production of the anti-PD-L1 antibodies of the present disclosure include Chinese hamster ovary (CHO) cells, including DHFR-CHO cells (see e.g., Urlaub et al., Proc. Natl. Acad. Sci. USA 77:4216 (1980)); myeloma cell lines such as Y0, NS0 and Sp2/0; monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse Sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells (see e.g., in Mather et al., Annals N Y. Acad. Sci. 383:44-68 (1982) and U.S. Pat. No. 6,235,498); Medical Research Council 5 (MRC 5) cells (such as e.g., those available from ATCC and also referred to as CCL-171); and Foreskin 4 (FS-4) cells (see e.g., in Vilcek et al. Ann. N. Y. Acad. Sci. 284:703-710 (1977), Gardner & Vilcek. J. Gen. Virol. 44:161-168 (1979), and Pang et al. Proc. Natl. Acad. Sci. U.S.A. 77:5341-5345 (1980)). For a general review of useful mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

V. Pharmaceutical Compositions and Formulations of Anti-PD-L1 Antibodies

The present disclosure also provides pharmaceutical compositions and pharmaceutical formulations comprising an anti-PD-L1 antibody. In some embodiments, the present disclosure provides a pharmaceutical formulation comprising an anti-PD-L1 antibody as described herein and a pharmaceutically acceptable carrier. In some embodiments, the anti-PD-L1 antibody is the sole active agent of the pharmaceutical composition. Such pharmaceutical formulations can be prepared by mixing an anti-PD-L1 antibody, having the desired degree of purity, with one or more pharmaceutically acceptable carriers. Typically, such antibody formulations can be prepared as an aqueous solution (see e.g., U.S. Pat. No. 6,171,586, and WO20061044908) or as a lyophilized formulation (see e.g., U.S. Pat. No. 6,267, 958).

Pharmaceutically acceptable carriers are generally non-toxic to recipients at the dosages and concentrations employed. A wide range of such pharmaceutically acceptable carriers are well-known in the art (see e.g., Remington's Pharmaceutical Sciences 16th edition, Osol, A. Ed. (1980)). Exemplary pharmaceutically acceptable carriers useful in the formulations of the present disclosure can include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, tar lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn— protein complexes); and/or non-ionic surfactants such as polyethylene glycol (PEG).

Pharmaceutically acceptable carriers useful in the formulations of the present disclosure can also include interstitial drug dispersion agents, such as soluble neutral-active hyaluronidase glycoproteins (sHASEGP) (see e.g., US Pat. Publ. Nos. 2005/0260186 and 2006/0104968), such as human soluble PH-20 hyaluronidase glycoproteins (e.g., rHuPH20 or HYLENEX®, Baxter International, Inc.).

It is also contemplated that the formulations disclosed herein may contain active ingredient, in addition to the anti-PD-L1, as necessary for the particular indication being treated in the subject to whom the formulation is administered. Preferably, any additional active ingredient has activity complementary to that of the anti-PD-L1 antibody activity and the activities do not adversely affect each other.

As disclosed elsewhere herein, including the Examples, it has been shown that the anti-PD-L1 antibodies of the present disclosure can be used in combination with an IL10 polypeptide to provide improved therapeutic effect in treating cancers. Accordingly, in some embodiments the present disclosure provides a pharmaceutical composition or formulation useful for treating a cancer comprising a PD-L1 antagonist (such as an anti-PD-L1) and an IL10 agonist (such as an IL10). In addition, to the use of the anti-PD-L1 antibodies of the present disclosure as PD-L1 antagonist in such a pharmaceutical formulation or composition, it is also contemplated that other antagonists can be used, including but not limited to a shRNA, a siRNA, a miRNA, a small molecule inhibitor of PD-L1, or a combination thereof. Small molecule inhibitors of PD-L1 useful in such pharmaceutical compositions or formulations can include known compounds in clinical development including, but not limited to, AUNP12 (Aurigene), CA-170 (Aurigene/Curis), and BMS-986189 (Bristol-Myers Squibb). Besides the anti-PD-L1 antibodies of the present disclosure, other known anti-PD-L1 antibodies useful in such a combination pharmaceutical composition or formulation with an IL10 can include any known antibodies that bind PD-L1, including those in clinical development for cancer treatment, such as Atezolizumab, Avelumab, Durvalumab, Lodapolimab, FAZ053 (BAP058-hum13), and MDX-1105, which are described elsewhere herein.

As described elsewhere herein, in some embodiments the present disclosure provides pharmaceutical composition or formulation for use in a combination therapy comprising a PD-L1 antagonist and an IL10 agonist. In some embodiments, this combination can be provided as a single pharmaceutical composition or formulation comprising an anti-PD-L1 antibody fusion having an anti-PD-L1 antibody covalently fused to a IL10 through a polypeptide linker, such as linker sequence of SEQ ID NO: 74, 75, 76, 77, 78, or 79. Examples demonstrating such anti-PD-L1 antibody fusions (e.g., PHS102/IL10) and their use in pharmaceutical compositions for reducing tumor volume in a range of syngeneic mouse cancer models is provided elsewhere herein including the Examples.

In some embodiments, the pharmaceutical composition comprises the anti-PD-L1 antibody and an additional active agent for cancer treatment such as an immune checkpoint inhibitor. Checkpoint inhibitors useful in such embodiments include, but are not limited to, a second antibody comprising a specificity for an antigen that is an immune checkpoint molecule. In some embodiments, the second antibody comprises a specificity for an immune checkpoint molecule selected from PD1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, ICOS. In at least one embodiment, the pharmaceutical composition comprising an anti-PD-L1 antibody and an additional active agent, wherein the additional active agent is an antibody comprising a specificity for the immune checkpoint molecule PD1. Exemplary antibodies comprising a specificity for PD1 that are useful in the pharmaceutical composition embodiments disclosed herein include, but are not limited to, pembrolizumab, nivolumab, cemiplimab, pidilizumab, dostarlimab, and HX008.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, the formulation can be a sustained-release preparation of the antibody and/or other active ingredients. Suitable examples of sustained-release preparations include semipermeable matrices of solid hydrophobic polymers containing the antibody, which matrices are in the form of shaped articles, e.g. films, or microcapsules.

Typically, the formulations of the present disclosure to be administered to a subject are sterile. Sterile formulations may be readily prepared using well-known techniques, e.g., by filtration through sterile filtration membranes.

VI. Uses and Methods of Treatment

It is contemplated that any of the compositions or formulations comprising an anti-PD-L1 antibody of the present disclosure can be used for any methods or uses, such as in therapeutic methods that utilize their ability to specifically bind to the PD-L1 protein and thereby inhibit, decrease, and/or fully block the function of PD-L1 as a protein involved in immune regulation or signaling, particularly the function of PD-L1 in specifically binding the immune checkpoint molecule, PD1, and thereby inhibiting an anti-tumor immune response (e.g., T-cell activation) in the tumor microenvironment (TME), and contributing to tumor growth and progression.

There are a range of diseases, disorders, and conditions that can potentially be treated by inhibiting, decreasing, and/or fully blocking the immune regulatory and/or immune signaling activity of PD-L1, particularly the effect of PD-L1 on tumor progression. Diseases, disorders, and conditions include, but are not limited to, cancers, including but not limited to colon cancer, pancreatic cancer, ovarian cancer, liver cancer, renal cancer, breast cancer, lung cancer, gastric cancer, head and neck cancer, or oral cancer. It is contemplated that any of the compositions or formulations comprising an anti-PD-L1 antibody of the present disclosure, including anti-PD-L1 antibody fusions with IL10 polypeptide, can be used for a method or use for the treatment of any of the above-listed cancers. In some embodiments, the cancer is selected from colon cancer, pancreatic cancer, ovarian cancer, liver cancer, renal cancer, breast cancer, lung cancer, gastric cancer, head and neck cancer, or oral cancer. In some embodiments, the present disclosure provides a method of treating cancer in a subject, the method comprising administering to the subject in need thereof a therapeutically effective amount of an anti-PD-L1 antibody of the present disclosure or administering to a subject a therapeutically effective amount of a pharmaceutical composition comprising an anti-PD-L1 antibody of the present disclosure and a pharmaceutically acceptable carrier.

As disclosed herein, including in the Examples below, the anti-PD-L1 antibodies of the present disclosure have the ability to decrease, inhibit, and/or block PD1 binding to PD-L1, and thereby alter PD1 interaction with the immune signaling pathways mediated by PD-L1. Accordingly, in some embodiments, the present disclosure provides a method of treating a PD-L1-mediated disease or condition in a subject, the method comprising administering to the subject a therapeutically effective amount of an anti-PD-L1 antibody of the present disclosure or administering to a subject in need thereof a therapeutically effective amount of a pharmaceutical composition comprising an anti-PD-L1 antibody of the present disclosure and a pharmaceutically acceptable carrier. Similarly, in some embodiments, the present disclosure provides a method of treating a disease mediated by binding to PD-L1 expressed on cells in a subject, the method comprising administering to the subject, the method comprising administering to the subject a therapeutically effective amount of an anti-PD-L1 antibody of the present disclosure or administering to a subject in need thereof a therapeutically effective amount of a pharmaceutical composition comprising an anti-PD-L1 antibody of the present disclosure and a pharmaceutically acceptable carrier.

Administration of the anti-PD-L1 antibody, composition, or pharmaceutical formulation in accordance with the method of treatment provides an antibody-induced therapeutic effect that protects the subject from and/or treats the progression of a PD-L1-mediated disease in a subject. In some embodiments, the method of treatment can further comprise administration of one or more additional therapeutic agents or treatments known to those of skill in the art to prevent and/or treat the PD-L1-mediated disease or condition. Such methods comprising administration of one or more additional agents can encompass combined administration (where two or more therapeutic agents are included in the same or separate formulations), and separate administration, in which case, administration of the antibody composition or formulation can occur prior to, simultaneously, and/or following, administration of the additional therapeutic agent.

The cytokine IL10 exhibits anti-inflammatory and CD8+ T-cell activation properties. A strong IL-10 signal can promote tumor-specific CD8+ T-cell proliferation, revitalize exhausted T-cells, and thereby increase T-cell cytotoxicity. Accordingly, in at least one embodiment, the present disclosure contemplates a method of treatment that uses an PD-L1 antagonist (e.g., anti-PD-L1 antibody) in combination with an IL10 agonist. In at least one embodiment, this combination therapy can be carried out using an anti-PD-L1 antibody fusion with an IL10 polypeptide. As disclosed herein, the combination of PD-L1 inhibition to reduce the immunosuppressive effect of its binding to PD1 with a concentrated IL10 signal nearby in the TME to enhance T-cell cytotoxicity can provide an improved cancer therapy. Accordingly, in any of the embodiments of methods of treating a PD-L1-mediated disease (e.g., cancer) using an anti-PD-L1 antibody of the present disclosure, it is contemplated that the anti-PD-L1 antibody can be an antibody fusion (or fusion protein) with an IL10 polypeptide as disclosed elsewhere herein.

It is also contemplated that other PD-L1 or PD1 antagonists can be used in such a combination treatment with an IL10, including but not limited to a shRNA, a siRNA, a miRNA, or a small molecule inhibitor of PD-L1, or a combination thereof. Small molecule inhibitors of PD-L1 useful in such a method can include known PD-L1 inhibitor compounds in clinical development such as AUNP12 (Aurigene), CA-170 (Aurigene/Curis), and BMS-986189 (Bristol-Myers Squibb). Additionally, other known PD-L1 antagonist antibodies can be used in such a combination treatment with an IL10 including known antibodies that block PD-L1, including those in clinical development for cancer treatment such as Atezolizumab, Avelumab, Durvalumab, Lodapolimab, FAZ053 (BAP058-hum13), and MDX-1105.

In some embodiments of the methods of treatment of the present disclosure, the anti-PD-L1 antibody or pharmaceutical formulation comprising an anti-PD-L1 antibody is administered to a subject by any mode of administration that delivers the agent systemically, or to a desired target tissue. Systemic administration generally refers to any mode of administration of the antibody into a subject at a site other than directly into the desired target site, tissue, or organ, such that the antibody or formulation thereof enters the subject's circulatory system and, thus, is subject to metabolism and other like processes.

Accordingly, modes of administration useful in the methods of treatment of the present disclosure can include, but are not limited to, injection, infusion, instillation, and inhalation. Administration by injection can include intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion.

In some embodiments, a pharmaceutical formulation of the anti-PD-L1 antibody is formulated such that the antibody is protected from inactivation in the gut. Accordingly, the method of treatments can comprise oral administration of the formulation.

In some embodiments, use of the compositions or formulations comprising an anti-PD-L1 antibody of the present disclosure as a medicament are also provided. Additionally, in some embodiments, the present disclosure also provides for the use of a composition or a formulation comprising an anti-PD-L1 antibody in the manufacture or preparation of a medicament, particularly a medicament for treating, preventing or inhibiting a PD-L1-mediated disease. In a further embodiment, the medicament is for use in a method for treating, preventing or inhibiting a PD-L1-mediated disease comprising administering to an individual having a PD-L1-mediated disease an effective amount of the medicament. In certain embodiments, the medicament further comprises an effective amount of at least one additional therapeutic agent, or treatment. In at least one embodiment, the additional therapeutic agent or treatment is an IL10 agonist, such as an IL10 polypeptide, that is administered in combination with an anti-PD-L1 antibody (rather than as an antibody fusion).

As disclosed elsewhere herein, it is also contemplated that additional therapeutic agents or treatments that can be used in such medicaments with anti-PD-L1 antibodies of the present disclosure can include but are not limited to therapeutic antibodies comprising a specificity for an immune checkpoint molecule such as PD1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, ICOS. Exemplary antibodies comprising a specificity for an immune checkpoint molecule include, but are not limited to an anti-PD1 antibody selected from pembrolizumab, nivolumab, cemiplimab, pidilizumab, dostarlimab, and HX008.

In a further embodiment, the medicament is for use in treating, inhibiting or preventing a PD-L1-mediated disease, such as a cancer, in a subject comprising administering to the subject an amount effective of the medicament to treat, inhibit or prevent the PD-L1-mediated disease.

The appropriate dosage of the anti-PD-L1 antibody contained in the compositions and formulations of the present disclosure (when used alone or in combination with one or more other additional therapeutic agents) will depend on the specific disease or condition being treated, the severity and course of the disease, whether the antibody is administered for preventive or therapeutic purposes, the previous therapy administered to the patient, the patient's clinical history and response to the antibody, and the discretion of the attending physician. The anti-PD-L1 antibody included in the compositions and formulations described herein, can be suitably administered to the patient at one time, or over a series of treatments. Various dosing schedules including but not limited to single or multiple administrations over various timepoints, bolus administration, and pulse infusion are contemplated herein.

Depending on the type and severity of the disease, about 1 µg/kg to 15 mg/kg of anti-PD-L1 antibody in a formulation of the present disclosure is an initial candidate dosage for administration to a human subject, whether, for example, by one or more separate administrations, or by continuous infusion. Generally, the administered dosage of the antibody would be in the range from about 0.05 mg/kg to about 10 mg/kg. In some embodiments, one or more doses of about 0.5 mg/kg, 2.0 mg/kg, 4.0 mg/kg or 10 mg/kg (or any combination thereof) may be administered to a patient.

Dosage administration can be maintained over several days or longer, depending on the condition of the subject, for example, administration can continue until the PD-L1-mediated disease is sufficiently treated, as determined by methods known in the art. In some embodiments, an initial higher loading dose may be administered, followed by one or more lower doses. However, other dosage regimens may be useful. The progress of the therapeutic effect of dosage administration can be monitored by conventional techniques and assays.

Accordingly, in some embodiments of the methods of the present disclosure, the administration of the anti-PD-L1 antibody comprises a daily dosage from about 1 mg/kg to about 100 mg/kg. In some embodiments, the dosage of anti-PD-L1 antibody comprises a daily dosage of at least about 1 mg/kg, at least about 5 mg/kg, at least about 10 mg/kg, at least about 20 mg/kg, or at least about 30 mg/kg.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1

Anti-PD-L1 Antibody and IL10 Fusion Generation and Binding Analysis

This example illustrates the use of phage-displayed antibody library technology to generate exemplary anti-PD-L1 antibodies and anti-PD-L1/IL10 fusion proteins of the present disclosure that specifically bind to human PD-L1 and/or IL10R, and block the ability of PD-L1 to bind to PD-1.

A. Selection of Anti-PD-L1 scFv Binders from Phage-Displayed Antibody Libraries

The panning procedure was briefly described below. First, human PD-L1/ECD antigen (5 μg per well, Sino Biological) was coated in PBS buffer (pH 7.4) in 96-well plate (NUNC Maxisorb immunoplate) overnight at 4° C. and then blocked with 5% skim milk in PBST [0.1% (v/v) Tween 20] for 1 h. After blocking, 100 μL concentrated phage library (1013 cfu/mL in PBS buffer) was mixed with 100 μL blocking buffer, and then added to each well for 1 h under gentle shaking. The plate was washed 12 times with PBST and 3 times with PBS. The bound phages were eluted with 100 μL of 0.1 M HCl/glycine (pH 2.2) per well, immediately neutralized with 20 μL of 1 M Tris-base buffer (pH 9.0). The eluted phages were mixed with 1 mL of E. coli ER2738 (A600 nm=0.6) for 30 min at 37° C.; uninfected bacteria were eliminated by adding ampicillin After ampicillin treatment for 30 minutes, the bacterial culture was infected with 100 μL M13KO7 helper phage (~1011 CFU total) at 37° C. for 1 h and then added to 50 mL of 2× YT medium containing kanamycin 50 μg/mL and ampicillin 100 μg/mL overnight at 37° C. with vigorous shaking. The rescued phage library was precipitated with 20% polyethylene glycol/NaCl and resuspended in PBS. The concentrated phage solution was used for the next round of panning.

After 3~4 rounds of selection-amplification cycle, single colonies were randomly selected into deep 96 well culture plate (plate A; secreted scFv); each well contained 950 μL 2 YT (100 μg/mL ampicillin). After 3 h incubation at 37° C. with shaking, 50 μL of bacterial culture was transferred to the corresponding well of a fresh deep 96-well plate (plate B; phage form); each well contained 0.8 mL 2 YT with 100 μg/mL ampicillin. In the meantime, 50 μL M13KO7 (~5× 1010 CFU total) was added to each well of plate B. After 1 h incubation, 100 μL 2 YT containing IPTG (10 mM) was added to each well of plate A; 100 μL 2 YT containing kanamycin (500 μg/mL) was added to each well of plate B. After overnight incubation at 37° C. with vigorous shaking, the cultures were centrifuged at 3000 g for 10 min at 4° C. The plate B was stored for further sequencing determination. For secreted scFv culture plate (plate A), 100 μL culture medium and 100 μL 5% PBST milk was added to a corresponding well of three 96-well plates pre-coated with protein L (0.1 μg/well), human CD36 (0.5~1 μg/well) and bovine serum albumin (BSA) (2 μg/well), respectively and blocked with 5% PBST milk. After 1 h incubation at room temperature, the plates were washed three times with PB ST. 100 μL Protein A-HRP (Thermo Scientific) was added to each well of Protein L-coated immunoplate; 100 μL anti-E-tag-HRP (ICL Inc.) was added to each well of human PD-L1.ECD antigen-coated and BSA-coated plates. After 1 h incubation, the plates were washed three times with PBST buffer and twice with PBS, developed for 3 min with 3,3',5,5'-tetramethyl-benzidine peroxidase substrate (Kirkegaard & Perry Laboratories), quenched with 1.0 M HCl and read spectrophotometrically at 450 nm.

Positive clones were selected by the following criteria: ELISA OD450>0.2 for the human PD-L1.ECD antigen-coated well (antigen binding positive); OD450<0.05 for BSA-coated well (non-specific binding negative); OD450>0.5 for the Protein L-coated well (soluble scFv binding to both Protein L and Protein A to ensure proper folding in solution), and then subjected to DNA sequencing.

Polynucleotide sequences of scFvs of exemplary anti-PD-L1 antibodies PHS102 (SEQ ID NO: 162), PHS206 (SEQ ID NO: 163), and PHS219 (SEQ ID NO: 164) obtained from phage display panning are provided in Table 3 and the accompanying Sequence Listing.

To further increase the affinity of the anti-PDL1 antibody PHS102, six phage display libraries were created for individual CDR mutagenesis of PHS102. After the first round of panning, 38 unique CDRs from CDR-L3, CDR-H1, CDR-H2 and CDR-H3 were selected and assembled as new libraries for the dissociation selection. To select the phages with improved off-rate scFv, the dissociation selection was conducted by co-incubating with 10-, 100-, or 1000-fold of hPDL1.ECD protein during panning. Further panning of these phage display libraries composed of variant CDR sequences derived from the anti-PD-L1 antibody PHS102 resulted in the following eight exemplary anti-PD-L1 antibodies (scFv polynucleotide sequences): YT6D (SEQ ID NO: 165), YP11F (SEQ ID NO: 166), YT10H (SEQ ID NO: 167), YT7A (SEQ ID NO: 170), YT7H (SEQ ID NO: 171), YP7G (SEQ ID NO: 172), HSYPP31F (SEQ ID NO: 168), and HSYPP411C (SEQ ID NO: 169) Amino acid sequences of the CDRs, $V_H$, $V_L$, heavy chain, and light chains of these eight anti-PD-L1 antibodies are also listed in Table 3 and the accompanying Sequence Listing.

B. Generation of Full-Length Anti-PD-L1 Antibodies and Anti-PD-L1/IL10 Fusions scFv reformatting and cloning: The PD-L1 binding determinants of the scFvs selected from phage display panning were reformatted into full-length IgG antibodies by cloning the $V_H$ and $V_L$ domains of the fragments into the human IgG1-N297A heavy chain vector and the human kappa light chain vector using the restriction sites MluI/NheI and BsiWI/DraIII, respectively. $V_H$ and $V_L$ domains were amplified using the following forward and reverse oligonucleotide primer pairs: (1) PhageLib_VL_Fw: 5'-AATCACgATgTgA-TATTCAAATgACCCAgAgCCCgAgC-3' (SEQ ID NO: 177), (2) PhageLib_VL_Rv: 5'-AATCgTACgTTTgATTTC-CACTTTggTgCCTTg-3' (SEQ ID NO: 178), (3) PhageLib_VH_Fw: 5'-AATACgCgTgTCCTgTCCgAAgTgCAgCTggTg-gAATCg-3' (SEQ ID NO: 179), and (4) PhageLib_VH_Rv: 5'-AATgCTAgCCgAgCTCACggTAACAAg-3'(SEQ ID NO: 180).

Generation of anti-PD-L1/IL10 fusion protein: A recombinant IL10-Fc fusion protein (SEQ ID NO: 86) was designed by genetically fusing IL-10 (SEQ ID NO: 73) to the N-terminus of the human IgG1-Fc separated by a 15 amino acid linker sequence, -GGGGSGGGGSGGGGS- (SEQ ID NO: 76). Recombinant anti-PD-L1/IL10 fusion proteins were designed by genetically fusing IL-10 to the C-terminus of the antibody heavy chain separated by the amino acid linker sequence of -LGGGGSGGGGSGGGG- (SEQ ID NO: 74). Other useful linker sequences are provided in Table 2. The desired gene segments, preceded by an IL-2 secretion sequence required for secretion of recombinant proteins, were obtained using Thermo gene synthesis service and cloned in a mammalian expression vector for transfection of and expression in ExpiCHO-S cells.

The full-length anti-PD-L1 antibodies, Atezolizumab, Avelumab, Durvalumab, Lodapolimab, FAZ053, and MDX-1105, were obtained using Thermo gene synthesis service and cloned in a mammalian expression vector for transfection of and expression in ExpiCHO-S cells. Polypeptide sequences are provided in Table 3 and the accompanying Sequence Listing.

Expression of full-length antibodies and fusion proteins: The vectors cloned with the reformatted anti-PD-L1 antibody or anti-PD-L1/IL10 fusion genes were transiently expressed in ExpiCHO-S cells (Thermo Scientific). During exponential growing phage, $6 \times 10^6$ ExpiCHO-S cells were transiently transfected with 20 μg of the vectors by ExpiFectamine CHO Transfection Kit (Thermo Scientific). 18-22 hours after transfection, ExpiFectamine CHO Enhancer and ExpiCHO Feed were added to the flask. The cells were cultured for 8 days. The supernatant of each culture was centrifuged and subsequently filtered through a 0.45 μm filter.

Purification and SDS-PAGE Characterization of Full-Length Antibodies and Fusion Proteins: Antibodies and Ab/IL10 fusion proteins were purified from the transfected cell supernatants with Protein A Sepharose Fast Flow beads (GE Healthcare). Antibody loaded columns were washed with 20 column volumes of PBS, and then eluted with 3 beads volume of 0.1 M Glycine (pH 2.5) directly into 1/10 volume of 1M Tris buffer (pH 9.0). Antibody containing fractions were pooled and dialyzed against PBS. The quality of purified anti-PD-L1 antibodies and fusion proteins was determined using SDS-PAGE in the presence or absence of a reducing agent.

Figure 1B:
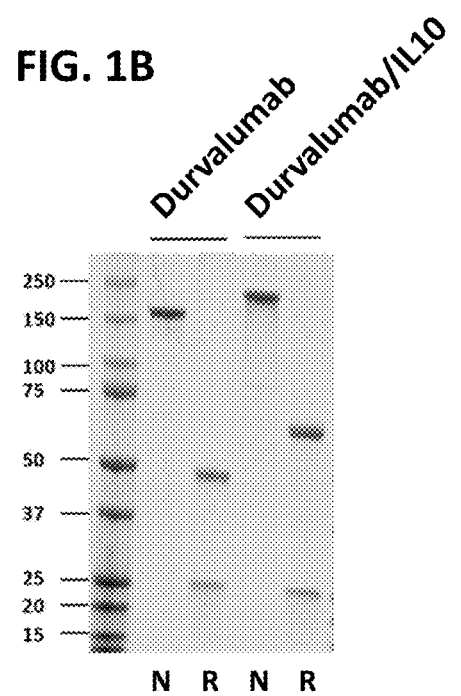
Figure 1C:
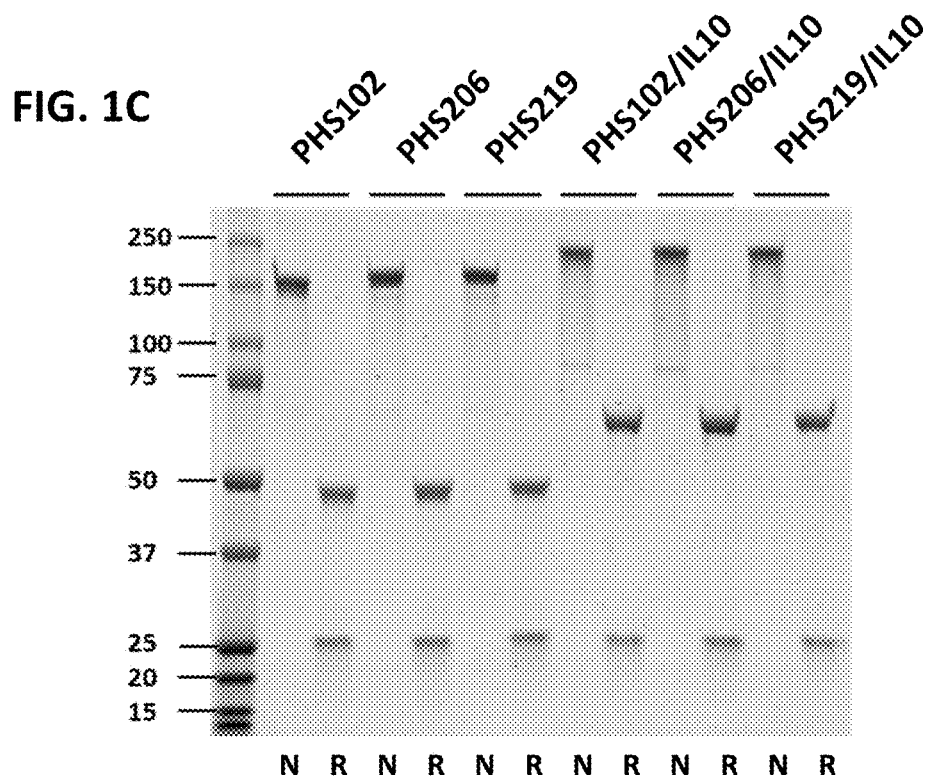

SDS-PAGE results: Examination of the SDS-PAGE images depicted in FIG. 1A and FIG. 1B show that the cloning, expression, and purification resulted in purified anti-PD-L1 antibodies in full-length IgG format, and anti-PD-L1 fusions with IL10 polypeptide.

Example 2

Specific Binding Assays of Anti-PD-L1 Antibody and Anti-PD-L1/IL10 Fusion Proteins This example illustrates ELISA and BLI studies showing the specific antigen binding and blocking function of anti-PD-L1 antibodies and anti-PD-L1/IL10 fusions.

A. ELISA of Antigen Specific Binding by Full-Length Antibodies and Fusion Proteins A recombinant human PD-L1-mFc fusion protein (1 μg/mL), recombinant cynomolgus PD-L1 (1 μg/mL; Sino Biological), or an IL10Rα-Fc fusion protein (1 μg/mL, R&D Systems) were immobilized on 96 well microtiter plate at a concentration of 1 μg/ml in Coating Solution (SeraCare) overnight at 4° C. The wells were washed with wash solution (0.05% Tween20 in imidazole-buffered saline) and blocked with 1% BSA. Serial dilutions of anti-PD-L1 or anti-PD-L1/IL10 fusion proteins were added to wells. After incubation at 37° C. for 1 hr, the wells were washed with wash solution. Peroxidase-conjugated Goat anti-human kappa Light chain antibody (Sigma) was applied to each well at 37° C. for 1 h incubation. For PD-1/PD-L1 competition ELISA, biotin-conjugated PD-1-Fc protein (30 μg/mL, Biolegend) was added. The binding of PD-1 was detected by streptavidin-HRP. After washing, the wells were developed with TMB substrate for 5-10 min at RT and then stopped with 1 N HCl. Thereafter, absorbance was measured at 450 nm and 650 nm. EC50 and IC50 values were calculated using GraphPad Prism7.

Results

ELISA-determined EC50 values showing the specific binding activity for human PD-L1 exhibited by the exemplary anti-PD-L1 antibodies and anti-PD-L1/IL10 fusions of the present disclosure are shown in Table 4 below.

TABLE 4

| Specific binding activity for human PD-L1 protein | |
|---|---|
| | $EC_{50}$ (M) |
| Anti-PD-L1 antibodies | |
| PHS102 | 0.784E−10 |
| PHS206 | 0.525E−10 |
| PHS219 | 2.043E−10 |
| Anti-PD-L1/IL10 fusions | |
| Atezolizumab/IL10 | 0.865E−10 |
| Avelumab/IL10 | 1.835E−10 |
| Avelumab/TGFβR | 1.067E−10 |
| Durvalumab/IL10 | 1.207E−10 |
| PHS102/IL10 | 0.798E−10 |
| PHS206/IL10 | 0.629E−10 |
| PHS219/IL10 | 1.643E−10 |

ELISA-determined EC50 values showing the specific binding activity for cynomolgus PD-L1 exhibited by the exemplary anti-PD-L1 antibodies and anti-PD-L1/IL10 fusions of the present disclosure are shown in Table 5 below.

TABLE 5

| Specific binding activity for cynomolgus PD-L1 protein | |
|---|---|
| Anti-PD-L1 antibodies | $EC_{50}$ (M) |
| Atezolizumab | 0.140E−09 |
| PHS102 | 0.216E−09 |
| PHS206 | 0.187E−09 |

ELISA-determined EC50 values showing the specific binding activity for IL10R exhibited by the exemplary anti-PD-L1/IL10 fusions of the present disclosure are shown in Table 6 below.

TABLE 6

| Specific binding activity for human IL10Rα | |
|---|---|
| Anti-PD-L1/IL10 fusions | EC50 (M) |
| Atezolizumab/IL10 | 8.725E−08 |
| Avelumab/IL10 | 2.591E−08 |
| Durvalumab/IL10 | 3.755E−08 |
| PHS102/IL10 | 9.426E−08 |
| PHS206/IL10 | 6.194E−08 |
| PHS219/IL10 | 6.626E−08 |

Figure 2A:
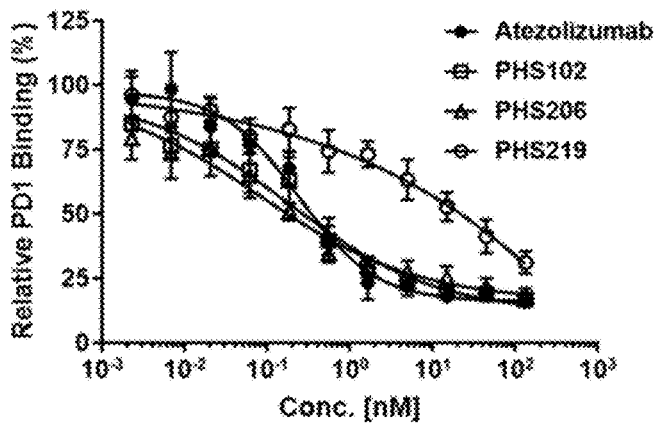
FIG. 2A, FIG. 2B, and FIG. 2C depict plots of results of a competition ELISA study showing the ability of exemplary anti-PD-L1 antibodies and anti-PD-L1/IL10 fusion proteins to block the specific binding of human PD-L1 to human PD1. Recombinant human PD-L1 (1 µg/mL) was immobilized on microtiter wells, biotin-conjugated human PD1 was added detected by streptavidin using ELISA, as described in Example 2. To test the competition activity, serial dilutions of anti-PD-L1 or anti-PD-L1/IL10 fusion proteins were added.
Figure 2B:
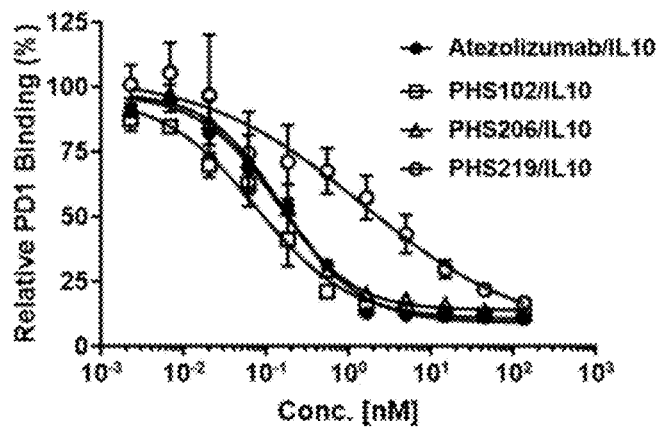
Figure 2C:
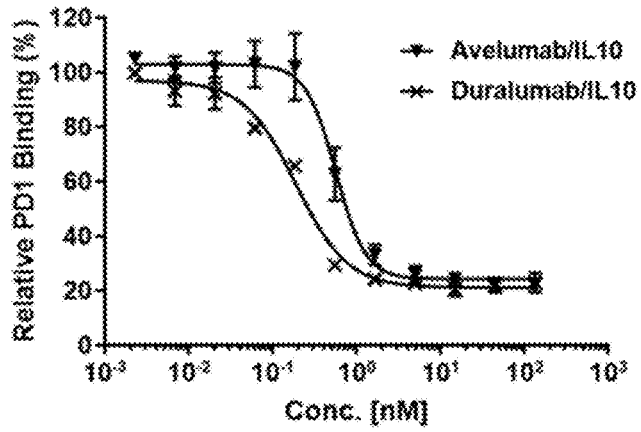

Plots of the binding data obtained by competition ELISA are shown in FIGS. 2A, 2B, and 2C. The IC50 values showing the specific activity for blocking the binding of PD-1 to PD-L1 exhibited by the exemplary anti-PD-L1/IL10 fusions of the present disclosure are shown in Table 7 below.

TABLE 7

| Specific activity for blocking interaction of hPD-1 and hPD-L1 | |
|---|---|
| | IC50 (M) |
| Anti-PD-L1 antibodies | |
| Atezolizumab | 0.239E−09 |
| PHS102 | 0.182E−09 |
| PHS206 | 0.083E−09 |
| PHS219 | 3.8900E−05 |

TABLE 7-continued

Specific activity for blocking interaction of hPD-1 and hPD-L1

| | IC50 (M) |
|---|---|
| Anti-PD-L1/IL10 fusions | |
| Atezolizumab/IL10 | 0.124E−09 |
| Avelumab/IL10 | 0.559E−09 |
| Durvalumab/IL10 | 0.188E−09 |
| PHS102/IL10 | 0.061E−09 |
| PHS206/IL10 | 0.116E−09 |
| PHS219/IL10 | 1.204E−09 |

B. BLI Analysis of Anti-PD-L1 Binding Kinetics

A Bio-Layer Interferometry (BLI) (ForteBio Octet RED96) assay was performed using AHC (Anti-hIgG Fc Capture) biosensors (ForteBio) to capture each anti-PD-L1 antibody (5 µg/mL) to acquire a 0.5 nm shift and then the biosensors were dipped into varying concentrations (i.e. 0, 1.5625, 3.125, 6.25, 4.94, 12.5, 25, 50 and 100 nM) of recombinant human PD-L1-His in running buffer containing PBS-Tween 20 (0.1%), BSA (0.1%). Rate constants were calculated by curve fitting analyses (1:1 Langmuir model) of binding response with a 2.5-minute association and 5-minute dissociation interaction time.

Results: The dissociation constant, $K_D$, and the kinetic rate constants, $k_a$ and $k_d$, determined by BLI for the specific binding of exemplary anti-PD-L1 antibodies to the antigen PD-L1 are provided in Table 8 below.

TABLE 8

Specific binding kinetics of anti-PD-L1 antibodies to hPD-L1

| Anti-PD-L1 Ab | $K_D$ (M) | $k_a$ (1/Ms) | $k_d$ (1/s) |
|---|---|---|---|
| PHS102 | 1.44E−08 | 4.73E+05 | 6.79E−03 |
| YT6D | 2.16E−09 | 3.30E+05 | 7.13E−04 |
| YP11F | 1.84E−09 | 3.34E+05 | 6.15E−04 |
| YT10H | 1.92E−09 | 3.50E+05 | 6.70E−04 |
| HSYPP31F | 1.88E−09 | 2.88E+05 | 5.42E−04 |
| HSYPP411C | 2.03E−09 | 3.21E+05 | 6.53E−04 |
| YT7A | 1.99E−09 | 3.03E+05 | 6.03E−04 |
| YT7H | 6.16E−09 | 2.03E+05 | 1.25E−03 |
| YP7G | 5.51E−09 | 2.47E+05 | 1.36E−03 |

Example 3

Cellular Binding Assays of Anti-PD-L1 Antibodies and Anti-PD-L1/IL10 Fusion Proteins This example illustrates flow cytometry studies showing the specific binding of exemplary anti-PD-L1 antibodies and anti-PD-L1/IL10 fusion proteins of the present disclosure to PD-L1 expressing F293 cells.

Materials and Methods

A. Preparation of PD-L1 expressing F293 cells: The gene segment encoding full-length human PD-L1 was obtained using Thermo gene synthesis service and cloned in a mammalian expression vector pCDNA3.4. Freestyle 293-F cells (Thermo Scientific) were transfected with the PD-L1 expression vector by polyethylenimine (PEI) method and selected with Geneticin (Thermo Scientific) to establish a stable PD-L1 expressing F293 cell line.

B. Flow cytometry: The F293 cells or PD-L1-overexpressing F293 cells were incubated with anti-PD-L1 antibody or anti-PD-L1/IL10 fusion protein for 30 min at 4° C. After washing with FACS buffer (2% FBS in PBS), the cells were stained with anti-human IgG-Alexa Fluor 647 and analyzed by Attune NxT Flow Cytometer (Thermo Scientific) and cell surface binding was expressed as Geometric MFI.

C. PD-1 blocking assay: F293/hPD-L1 cells were incubated with serial dilutions of anti-PD-L1 antibody or anti-PD-L1/IL10 fusion protein on ice for 30 min. 20 µg/ml biotin-conjugated human PD1.ECD protein (SEQ ID NO: 175) was added and incubated on ice for 60 min. After washing with FACS buffer (2% FBS in PBS), the cells were stained with Streptavidin-Alexa Fluor 647 and analyzed by Attune NxT Flow Cytometer (Thermo Scientific).

Results

Figure 3A:
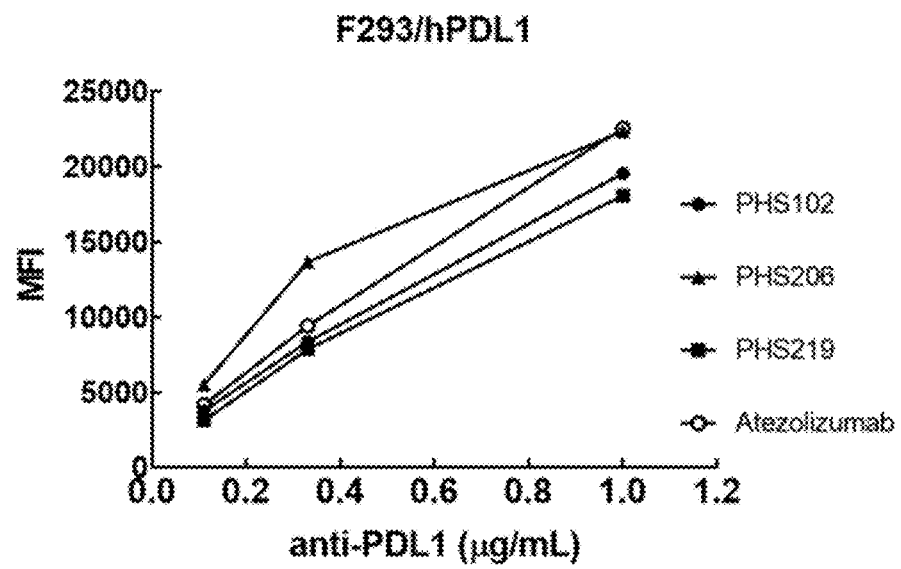
FIG. 3A and FIG. 3B depict plots of results from flow cytometry study of binding of exemplary anti-PD-L1 antibodies and anti-PD-L1/IL10 fusion proteins to stable F293 cells that overexpress human PD-L1 ("F293/hPDL1") that were generated by transfecting full-length human PD-L1 expression constructs into F293 cells and then selecting for selection-drug resistance, as described in Example 3.
Figure 3B:
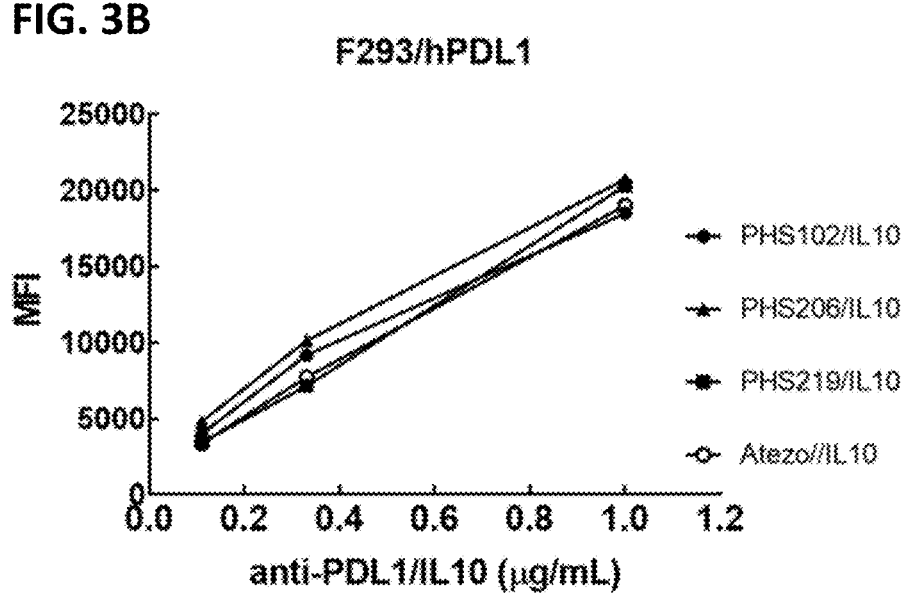

As shown by the plots of flow cytometry data depicted in FIGS. 3A and 3B, the exemplary anti-PD-L1 antibodies (PHS102, PHS206, PHS219, and Atezolizumab) and the corresponding anti-PD-L1/IL10 fusion proteins (PHS102/IL10, PHS206/IL10, PHS219/IL10, and Atezolizumab/IL10) exhibit specific binding activity to human PD-L1 expressed on the surface of F293 cells.

Figure 3C:
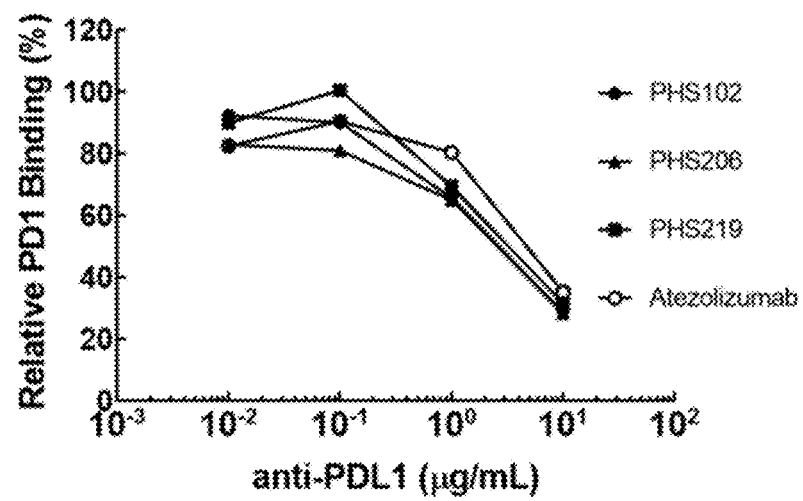
FIG. 3C and FIG. 3D depict plots of results from a flow cytometry study showing the ability of exemplary anti-PD-L1 antibodies and anti-PD-L1/IL10 fusion proteins to block the specific binding of human PD1 to stable F293 cells that overexpress human PD-L1 ("F293/hPDL1"). The F293/hPDL1 expressing cells were generated by transfecting full-length human PD-L1 expression constructs into F293 cells and then selecting for selection-drug resistance, as described in Example 3. F293/hPDL1 cells were incubated on ice for 1 h with biotin-conjugated hPD1 (20 µg/mL) and serial dilutions of exemplary anti-PD-L1 antibodies (FIG. 3C) or anti-PD-L1/IL10 fusion proteins (FIG. 3D). Cell surface binding of PD1 was detected by streptavidin and analyzed by flow cytometry.
Figure 3D:
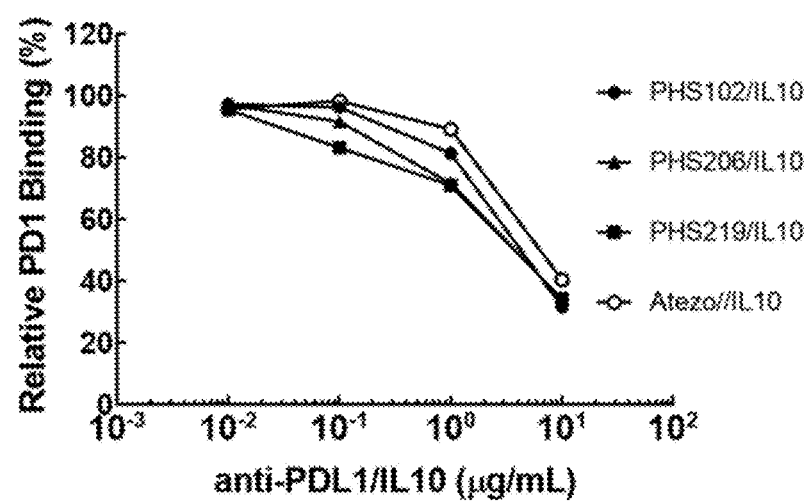

As shown by the plots of flow cytometry data depicted in FIGS. 3C and 3D, the exemplary anti-PD-L1 antibodies (PHS102, PHS206, PHS219, and Atezolizumab) and the corresponding anti-PD-L1/IL10 fusion proteins (PHS102/IL10, PHS206/IL10, PHS219/IL10, and Atezolizumab/IL10) exhibit specific blocking of the binding of human PD-1 to human PD-L1 expressed on the surface of F293 cells.

Example 4

Assay of PD-1/PD-L1 Cellular Signaling Blockade

This example illustrates studies of the ability of the exemplary anti-PD-L1 antibodies and anti-PD-L1/IL10 fusion proteins of the present disclosure to blockade PD-1/PD-L1 cellular signaling.

Materials and Methods

A PD-1/PD-L1 blockade bioassay was performed using PathHunter® PD-1 Signaling Bioassay Kit (Eurofins). Serial dilutions of exemplary anti-PD-L1 antibodies or anti-PDL1/IL10 fusion proteins were pre-incubated with PD-L1-presenting U2OS bioassay cells (1×10⁴ per well) for 1 hour at 37° C. Jurkat PD-1 signaling cells (2×10⁴ per well) were added to the PD-L1-presenting cells and incubated at room temperature for 2 hours prior to addition of detection reagent.

Results

Figure 4A:
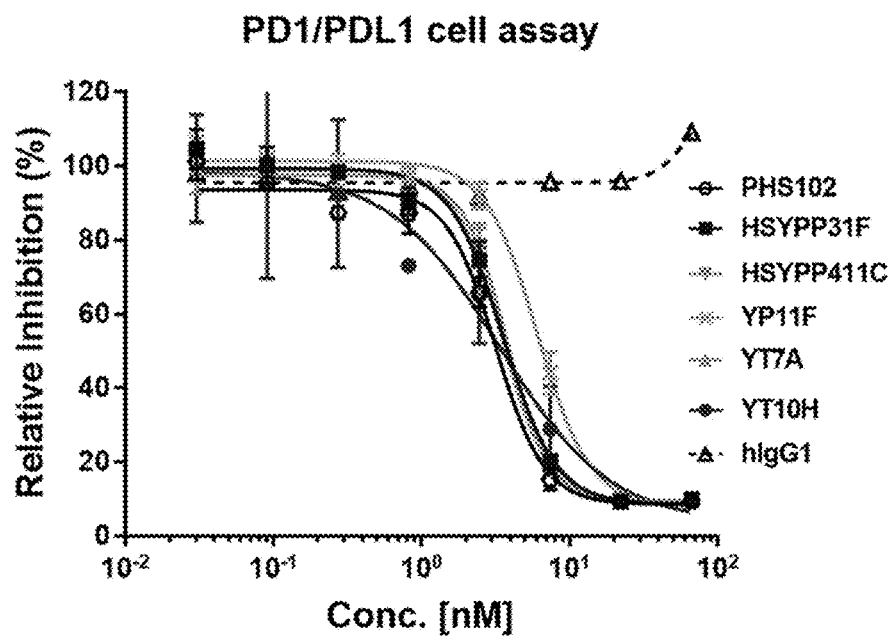
FIG. 4A and FIG. 4B depict plots results of PD1 signaling inhibition by exemplary anti-PD-L1 antibodies and anti-PD-L1/IL10 fusion proteins as described in Example 4. The exemplary anti-PD-L1 antibodies and anti-PD-L1/IL10 fusion proteins were assayed for ability to block PD1 activation mediated by a U2OS PD-L1 cell line co-culture. The U2OS PD-L1 cells were treated with serial dilutions of the anti-PD-L1 antibodies (FIG. 4A) or anti-PD-L1/IL10 fusion proteins (FIG. 4B) for 1 hour prior to stimulation with Jurkat PD1 signaling cells for 2 hours at room temperature.
Figure 4B:
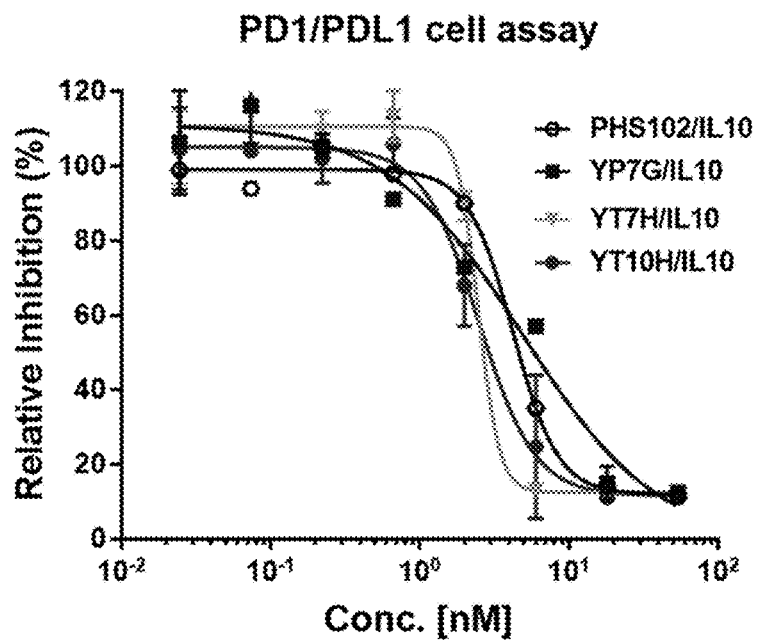

As shown by the blockade assay data plotted in FIGS. 4A and 4B and the IC50 values listed in Table 9, the exemplary anti-PD-L1 antibodies (PHS102, HSYPP31F, HSYPP411C, YT7A, YT7H, YP10H) and the anti-PD-L1/IL10 fusion proteins (PHS102/IL10, YT7A/IL10, YT7H/IL10, YP10H/IL10) are capable of blocking cellular signaling mediated by PD-1 binding to PD-L1.

TABLE 9

Specific activity for blocking PD-1/PD-L1 signaling

| | IC50 (nM) |
|---|---|
| Anti-PD-L1 antibodies | |
| PHS102 | 3.178 |
| HSYPP31F | 3.563 |
| HSYPP411C | 3.741 |
| YT7A | 6.07 |

TABLE 9-continued

Specific activity for blocking PD-1/PD-L1 signaling

| | IC50 (nM) |
|---|---|
| YT7H | 3.478 |
| YP10H | 3.381 |
| Anti-PD-L1/IL10 fusions | |
| PHS102/IL10 | 4.221 |
| YT7A/IL10 | 4.867 |
| YT7H/IL10 | 2.471 |
| YP10H/IL10 | 2.492 |

Example 5

Enhanced T Cell Activation by Anti-PD-L1 Antibodies and Fusion Proteins

This example illustrates studies of the ability of the exemplary anti-PD-L1 antibodies and anti-PD-L1/IL10 fusion proteins of the present disclosure to enhance T cell activation in a Mixed Lymphocyte Reaction (MLR).

Materials and Methods

Human peripheral blood was obtained from healthy donors. Peripheral blood mononuclear cells (PBMC) were immediately isolated by density gradient centrifugation using Ficoll-Paque Plus (GE Healthcare). To serve as allogeneic antigen presenting cells (APCs), CD14+ monocytes were first isolated by using anti-human CD14 conjugated magnetic beads (Miltenyi Biotec) from a Donor A. For immature dendritic cell (DC) differentiation, monocytes were cultured with GM-CSF (20 ng/mL) and IL-4 (20 ng/mL) in RPMI1640 supplemented with 10% FBS for 6 days. For mature DC generation, immature DCs were treated with LPS (500 ng/mL) for 24 hr. Mature DCs were treated with 40 µg/mL mitomycin C at 37° C. for 30 min before co-culture with T cells.

CD4+ T cells were isolated by using anti-human CD4 conjugated magnetic beads (Miltenyi Biotec) from Donor B. Responder CD4 T cells were resuspended at $4 \times 10^6$ cells/mL in culture medium, and 50 µL of T cells were added to all wells with the exception of the DC-only wells. Stimulator DCs were resuspended at $4 \times 10^6$ cells/mL in culture medium, and 50 µL of DCs were added to all wells with the exception of the CD4 T-only wells. An additional 100 µL of culture medium containing 0.1-2 µg IL10-Fc or anti-PD-L1/IL10 fusion protein was added to the CD4 T-DC culture in a 96-well U-bottom plate. The co-cultures were incubated at 37° C. Concentration of IL-2 in cell culture media after 2 days co-culture was determined by ELISA (Biolegend) according to the manufacturer's instructions.

Results

Figure 5A:
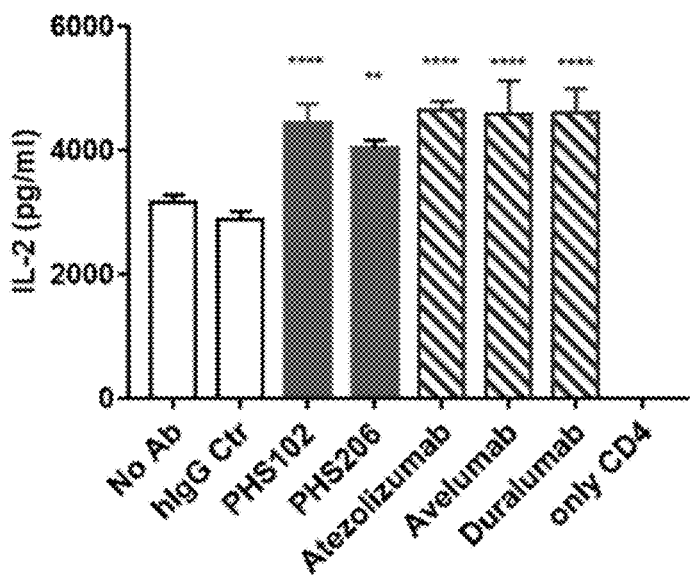
FIG. 5A and FIG. 5B depict plots of results of a study showing the ability of exemplary anti-PD-L1 antibodies and anti-PD-L1/IL10 fusion proteins to enhance T-cell activation in a CD4 T cell-DC-mixed lymphocyte reaction (MLR).
Figure 5B:
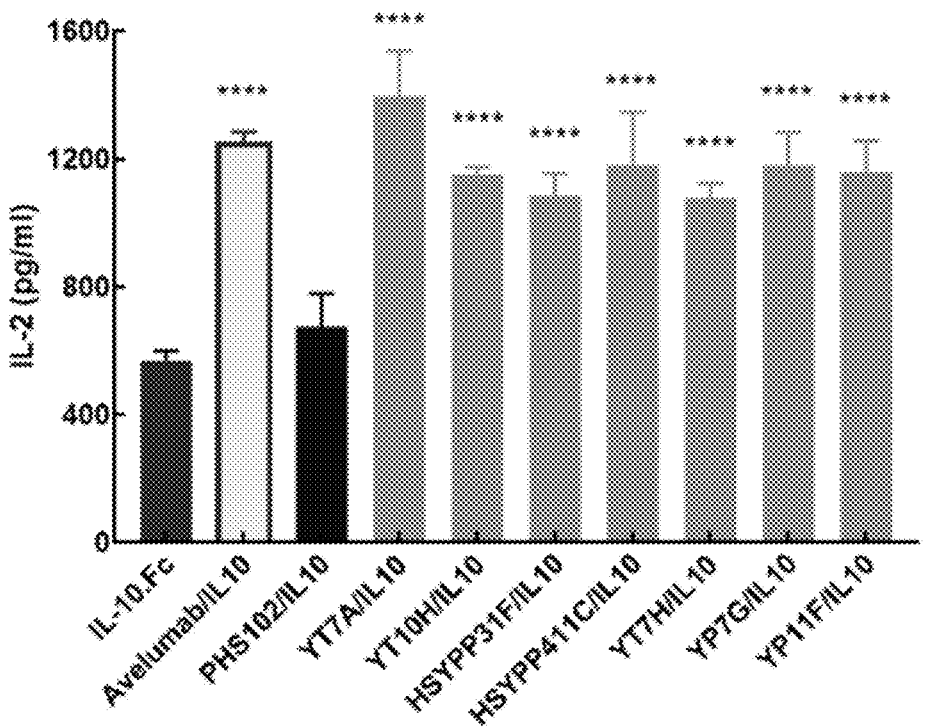
Figure 6A:
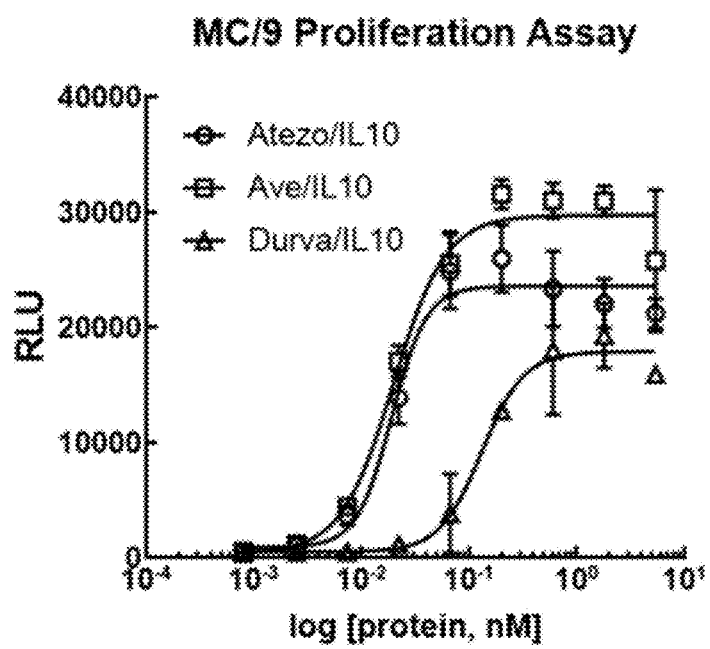
FIG. 6A, FIG. 6B, FIG. 6C, FIG. 6D, FIG. 6E, and FIG. 6F depict plots of data obtained in a study showing the induction of MC/9 cell proliferation by exemplary anti-PD-L1/IL10 fusion proteins as described in Example 6. MC/9 cells were co-cultured for 3 days with IL10-Fc and exemplary anti-PD-L1/IL10 fusion proteins of the present disclosure. Cell proliferation was measured by CellTiter-Glo assay.
Figure 6B:
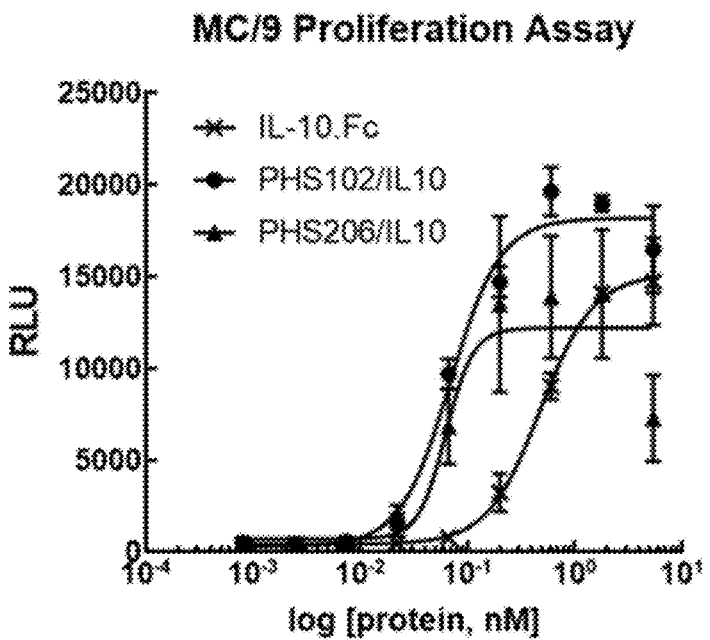
Figure 6C:
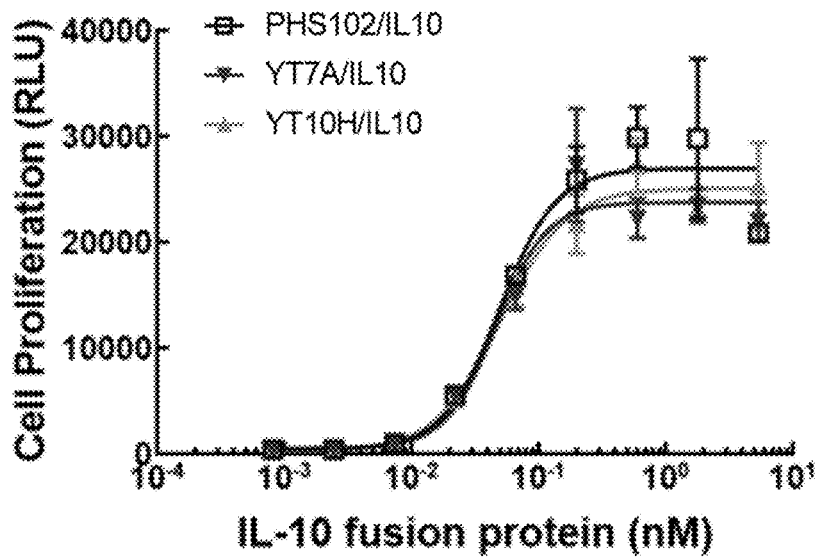
Figure 6D:
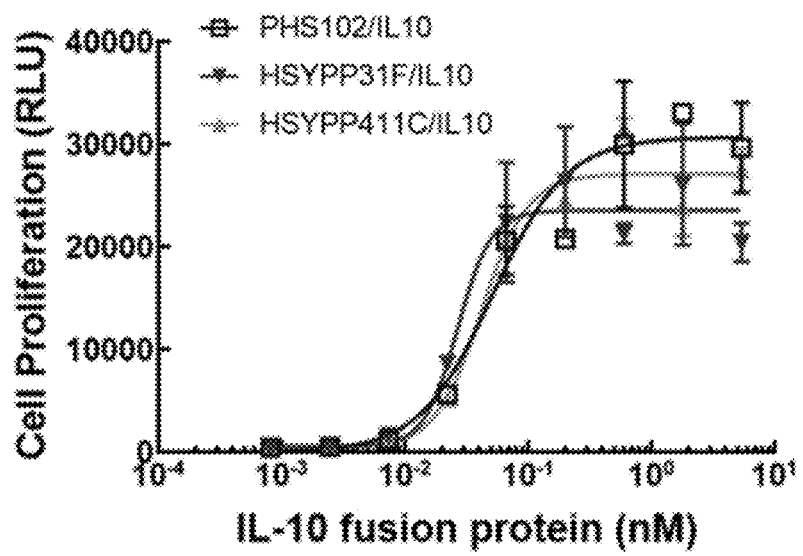
Figure 6E:
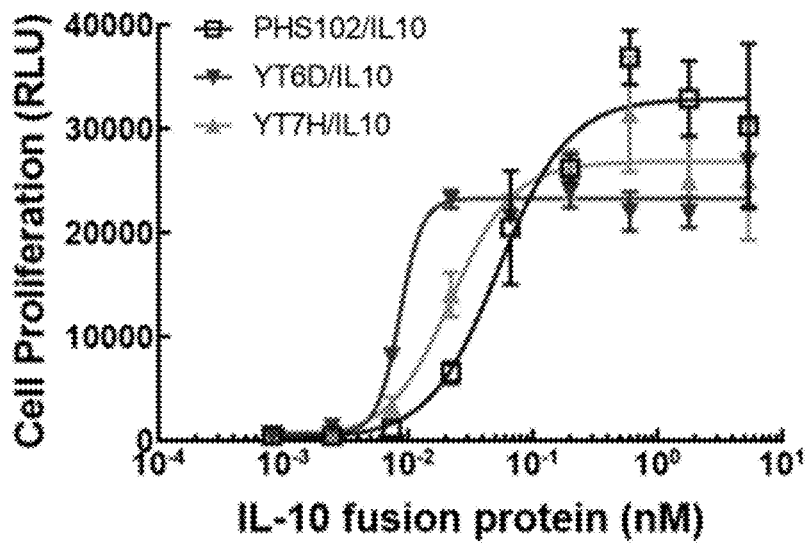
Figure 6F:
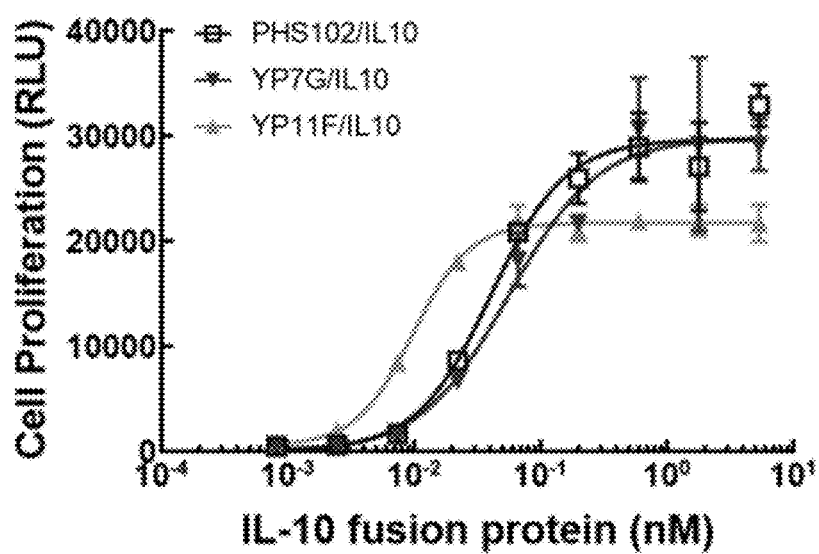

As shown by the assay data plotted in FIGS. 5A and 5B, the exemplary anti-PD-L1 antibodies (PHS102, PHS206, Atezolizumab, Avelumab, Durvalumab) and the anti-PD-L1/IL10 fusion proteins (Avelumab/IL10, PHS102/IL10, YT7A/IL10, YT10H/IL10, HSYPP31F/IL10, HSYPP411C/IL10, YT7H/IL10, YP7G/IL10, YP11F/IL10) are capable of enhancing T cell activation relative to hIgG or IL10-Fc controls in a MLR.

Example 6

Stimulation of MC/9 Cell Proliferation by Anti-PD-L1/IL10 Fusion Proteins

This example illustrates a study of the ability IL10 polypeptide linked to the exemplary anti-PD-L1/IL10 fusion proteins of the present disclosure to stimulate MC/9 cell proliferation.

Materials and Methods

The biological activity of IL10 was determined by using a proliferation assay. MC/9 (ATCC, CRL-8306) murine mast cells were cultured in DMEM (GIBCO) supplemented with 2 mM L-glutamine, 0.05 mM 2-mercaptoethanol, 10% Rat T-STIM (Becton Dickenson) and 10% FBS. In the proliferation assay, MC/9 cells were plated in 96-well plate at $1 \times 10^4$ per well in 200 µl of assay medium (DMEM containing 10% FBS) in the presence of IL10-Fc or an exemplary anti-PD-L1/IL10 fusion protein. After 72 hours stimulation. MC/9 cell proliferation was measured using CellTiter-Glo assay.

Results

As shown by the assay data plotted in FIGS. 6A, 6B, 6C, 6D, 6E, and 6F, and the EC50 values listed in Table 10 below, the exemplary anti-PD-L1/IL10 fusion proteins (Atezolizumab/IL10, Avelumab/IL10, Durvalumab/IL10, PHS102/IL10, PHS206/IL10, YT7A/IL10, YT10H/IL10, HSYPP31F/IL10, HSYPP411C/IL10, YT6D/IL10, YT7H/IL10, YP7G/IL10, YP11F/IL10) are capable of stimulating MC/9 proliferation at an enhanced level relative to an IL10-Fc protein.

TABLE 10

Specific activity for stimulating MC/9 proliferation

| | EC50 (nM) |
|---|---|
| IL10-Fc | 0.4781 |
| Anti-PD-L1/IL10 fusions | |
| Atezolizumab/IL10 | 0.0191 |
| Avelumab/IL10 | 0.0197 |
| Durvalumab/IL10 | 0.1309 |
| PHS102/IL10 | 0.0689 |
| PHS206/IL10 | 0.0626 |
| PHS102/IL10 | 0.04972 |
| YT7A/IL10 | 0.04662 |
| YT10H/IL10 | 0.05056 |
| PHS102/IL10 | 0.0515 |
| HSYPP31F/IL10 | 0.02683 |
| HSYPP411C/IL10 | 0.04183 |
| PHS102/IL10 | 0.05331 |
| YT6D/IL10 | 0.008582 |
| YT7H/IL10 | 0.02209 |
| PHS102/IL10 | 0.04052 |
| YP7G/IL10 | 0.0561 |
| YP11F/IL10 | 0.009712 |

Example 7

Activation of CD8 T Cells by Anti-PD-L1/IL10 Fusion Proteins

This example illustrates a study of the IL10 polypeptide linked to the exemplary anti-PD-L1/IL10 fusion proteins of the present disclosure to activate CD8 T cells.

Materials and Methods

Human CD8 T cells were isolated from PBMCs by using CD8 magnetic beads (Miltenyi Biotec). Isolated CD8 T cells ($1 \times 10^7$ cells/3 mL/well of a 6-well plate) were culture in AIM-V medium (Thermo Scientific) and activated with T Cell TransAct (Miltenyi Biotec) for 3 days. Following activation, CD8 T cells were then washed and plated $4 \times 10^5$ cells per well of a 96-well plate and treated with the anti-PD-L1/IL10 fusion protein for 3 days. Following treatment with the anti-PD-L1/IL10 fusion protein, the cells were restimulated with 1 µg/mL soluble anti-CD3 (Biolegend) for 4 h. Concentrations of IFN-γ and granzyme B in cell culture media were measured by ELISA (Biolegend) according to the manufacturer's instructions.

Results

Figure 7A:
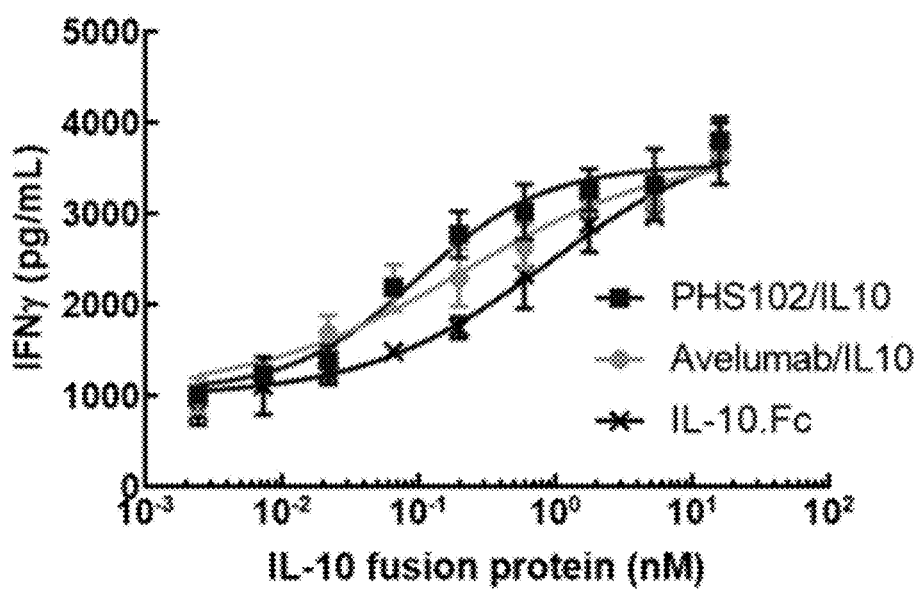
FIG. 7A and FIG. 7B depict plots of data obtained in a study showing the potentiation by exemplary anti-PD-L1/IL10 fusion proteins of IFNγ and granzyme B production from activated CD8 T cells, as described in Example 7. Isolated CD8 T cells were activated with anti-CD3 and anti-CD28 for 3 days. Activated CD8 T cells were treated with IL10-Fc or anti-PDL1/IL10 fusion proteins for 3 days and triggered with anti-CD3 for 4 hours. Levels of IFNγ (FIG. 7A) and cytotoxic protein granzyme B (FIG. 7B) were measured by ELISA.
Figure 7B:
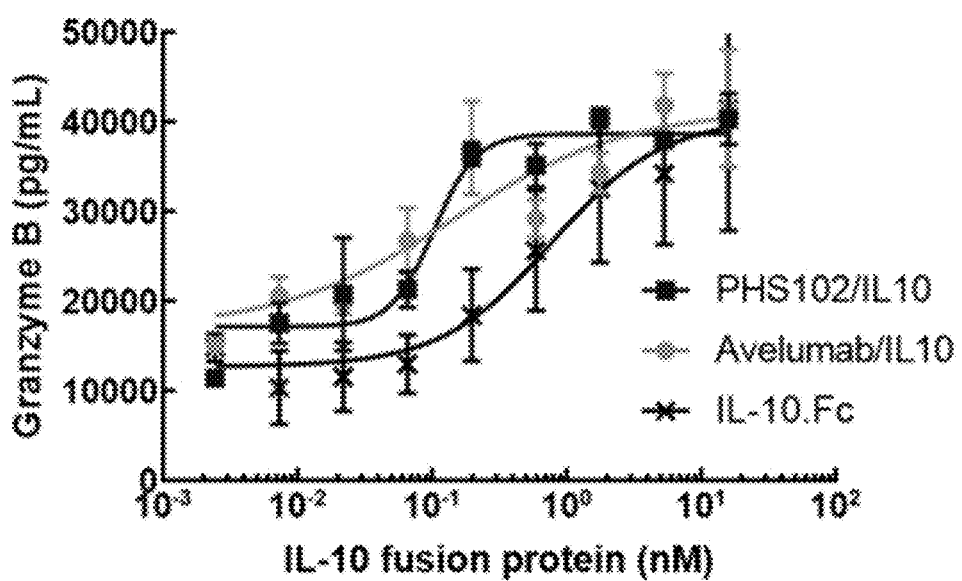

As shown by the assay data plotted in FIGS. 7A and 7B, and the EC50 values listed in Table 11 below, the exemplary anti-PD-L1/IL10 fusion proteins (Avelumab/IL10, PHS102/IL10) are capable of activating CD8 T cells (as measured by IFN-γ and granzyme B levels) at an enhanced level relative to IL10-Fc protein.

TABLE 11

Activation of CD8 T cells

| | EC50 (nM) | |
|---|---|---|
| | IFN-γ | Granzyme B |
| IL10-Fc | 0.871 | 0.776 |
| Anti-PD-L1/IL10 fusions | | |
| Avelumab/IL10 | 0.211 | 0.144 |
| PHS102/IL10 | 0.0985 | 0.103 |

Example 8

Anti-Tumor Activity of Anti-PD-L1/IL10 Fusion Proteins in Syngeneic Tumor Models This example illustrates a study of the anti-tumor activity of the exemplary anti-PD-L1/IL10 fusion proteins of the present disclosure in two syngeneic tumor models, CT26 and EMT6.

Materials and Methods

BALB/c mice (6-8 weeks old, female) were implanted subcutaneously with $5 \times 10^5$ CT26 cells (ATCC CRL-2638) or $5 \times 10^5$ EMT6 cells (ATCC CRL-2755). After 8 days, mice were randomized into treatment groups when tumor volume reached 50-100 mm$^3$. Mice were then injected intraperitoneally twice weekly with PBS control, 3 mg/kg IL10-Fc (92 kDa), 4.9 mg/kg anti-PD-L1 antibody (Avelumab) (150 kDa), 36 mg/kg anti-CSF1R/IL10 fusion (185.5 kDa), 5.8 mg/kg anti-PD-L1/TGFβR fusion (M7824) (177 kDa), or 6 mg/kg anti-PD-L1/IL10 fusion protein (Avelumab/IL10) (185.5 kDa). Tumor volume was measured twice per week by caliper measurements until end of the study.

Results

Figure 8A:
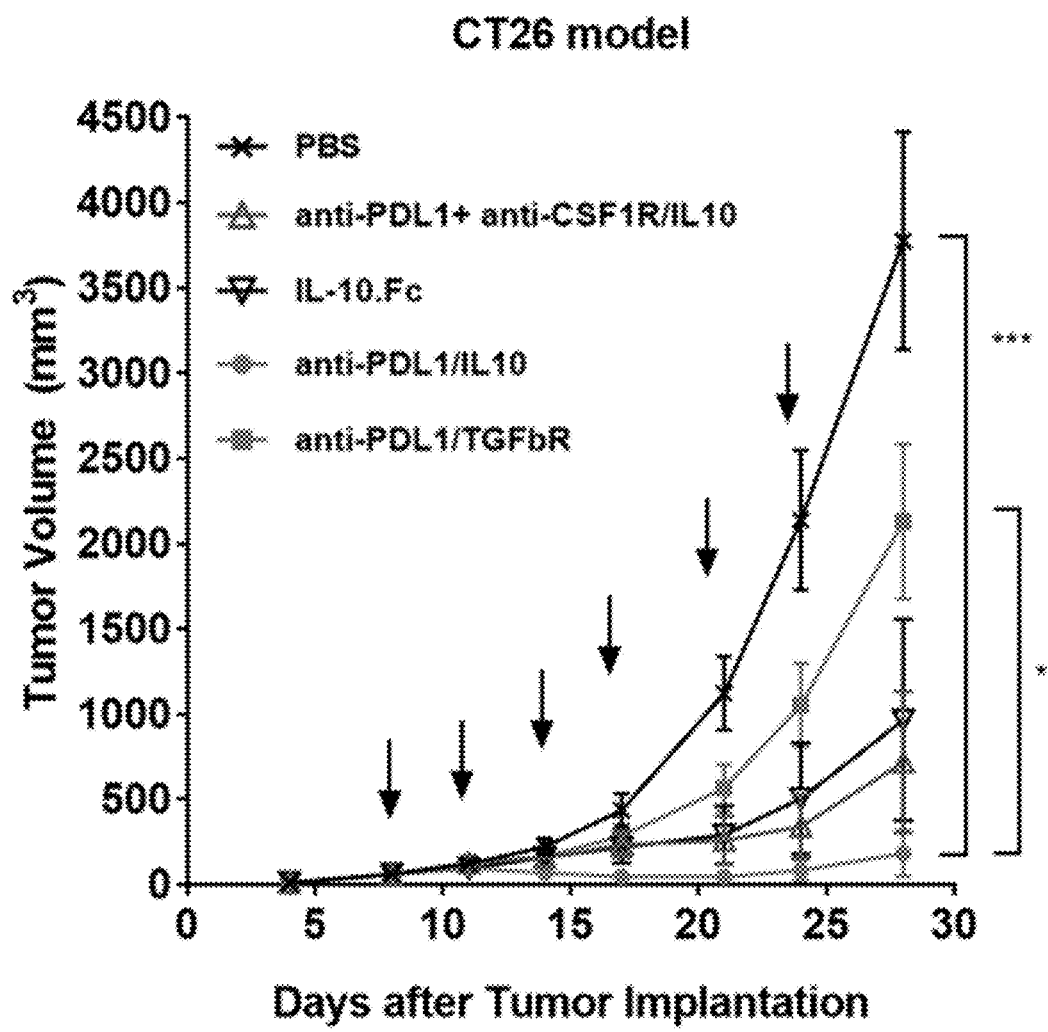
FIG. 8A depicts plots of data obtained in a study (described in Example 8) showing that exemplary anti-PD-L1/IL10 fusion proteins of the present disclosure act to control tumor burden in a syngeneic mouse CT26 tumor model. Mice were randomized once CT26 tumors reached 50-100 mm$^3$ and then treated with PBS control, IL10-Fc (3 mg/kg), anti-PD-L1/TGFβR (5.8 mg/kg), anti-PD-L1 (4.9 mg/kg), anti-CSF1R/IL10 (36 mg/kg), or anti-PD-L1/IL10 (6 mg/kg) twice weekly for 3 weeks. Tumor volumes over time of mice implanted with tumor cells at day 0. n=7 mice per group. Mean±SEM is shown. *p<0.001, **p<0.0001.
Figure 8B:
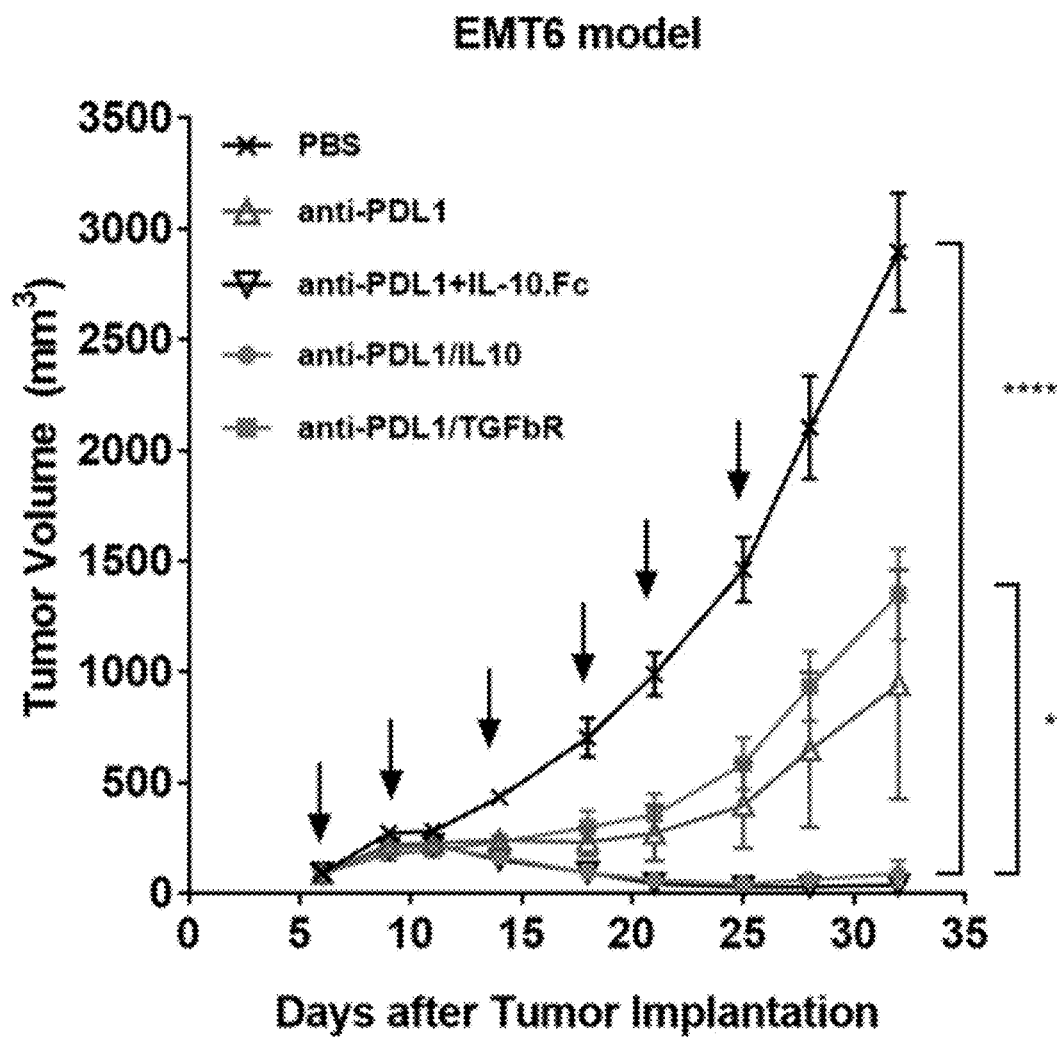
FIG. 8B depicts plots of data obtained in a study (described in Example 8) showing that exemplary anti-PD-L1/IL10 fusion proteins of the present disclosure act to control tumor burden in a syngeneic mouse EMT6 tumor model. Mice were randomized once EMT6 tumors reached 50-100 mm$^3$ and then treated with PBS control, anti-PDL1 (5 mg/kg), IL10-Fc (3 mg/kg), anti-PDL1/TGFβR (6 mg/kg), or anti-PDL1/IL10 (6 mg/kg) twice weekly for 3 weeks. Tumor volumes over time of mice implanted with tumor cells at day 0. n=7 mice per group. Mean±SEM is shown. *p<0.05, *p<0.001, **p<0.0001.

As shown by the tumor volume data plotted in FIGS. 8A and 8B, the exemplary anti-PD-L1/IL10 fusion protein of the present disclosure exhibited very strong anti-tumor activity over the course of the studies, showing the smallest tumor volume of all of treatments in both the CT26 and EMT6 tumor models.

Notwithstanding the appended claims, the disclosure set forth herein is also defined by the following clauses, which may be beneficial alone or in combination, with one or more other causes or embodiments. Without limiting the foregoing description, certain non-limiting clauses of the disclosure numbered as below are provided, wherein each of the individually numbered clauses may be used or combined with any of the preceding or following clauses. Thus, this is intended to provide support for all such combinations and is not necessarily limited to specific combinations explicitly provided below:

While the foregoing disclosure of the present invention has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedure to those described herein. All such equivalents are to be understood to be within the scope of the present disclosure and are covered by the appended claims.

Additional embodiments of the invention are set forth in the following claims.

The disclosures of all publications, patent applications, patents, or other documents mentioned herein are expressly incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including specified terms, will control.

What is claimed is:

1. An anti-PDL1 antibody comprising (i) a first light chain complementary determining region (CDR-L1), a second light chain complementary determining region (CDR-L2), and a third light chain complementary determining region (CDR-L3), and (ii) a first heavy chain complementary determining region (CDR-H1), a second heavy chain complementary determining region (CDR-H2), and a third heavy chain complementary determining region (CDR-H3), wherein:

(a) CDR-H1 comprises the amino acid sequence of SEQ ID NO: 49, CDR-H2 comprises the amino acid sequence of SEQ ID NO: 50, CDR-H3 comprises the amino acid sequence of SEQ ID NO: 51, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 55;

(b) CDR-H1 comprises the amino acid sequence of SEQ ID NO: 57, CDR-H2 comprises the amino acid sequence of SEQ ID NO: 58, CDR-H3 comprises the amino acid sequence of SEQ ID NO: 59, CDR-L1 comprises the amino acid sequence of SEQ ID NO: 61, CDR-L2 comprises the amino acid sequence of SEQ ID NO: 62, and CDR-L3 comprises the amino acid sequence of SEQ ID NO: 63;

(c) CDR-H1 comprises the amino acid sequence of SEQ ID NO: 65, CDR-H2 comprises the amino acid sequence of SEQ ID NO: 66, CDR-H3 comprises the amino acid sequence of SEQ ID NO: 67, CDR-L1 comprises the amino acid sequence of SEQ ID NO: 69, CDR-L2 comprises the amino acid sequence of SEQ ID NO: 70, and CDR-L3 comprises the amino acid sequence of SEQ ID NO: 71;

(d) CDR-H1 comprises the amino acid sequence of SEQ ID NO: 87, CDR-H2 comprises the amino acid sequence of SEQ ID NO: 88, CDR-H3 comprises the amino acid sequence of SEQ ID NO: 89, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 91;

(e) CDR-H1 comprises the amino acid sequence of SEQ ID NO: 93, CDR-H2 comprises the amino acid sequence of SEQ ID NO: 94, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 97;

(f) CDR-H1 comprises the amino acid sequence of SEQ ID NO: 99, CDR-H2 comprises the amino acid sequence of SEQ ID NO: 100, CDR-H3 comprises the amino acid sequence of SEQ ID NO: 101, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 103;

(g) CDR-H1 comprises the amino acid sequence of SEQ ID NO: 105, CDR-H2 comprises the amino acid sequence of SEQ ID NO: 106, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 108;

(h) CDR-H1 comprises the amino acid sequence of SEQ ID NO: 93, CDR-H2 comprises the amino acid sequence of SEQ ID NO: 110, CDR-H3 comprises the amino acid sequence of SEQ ID NO: 111, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 113;

(i) CDR-H1 comprises the amino acid sequence of SEQ ID NO: 93, CDR-H2 comprises the amino acid sequence of SEQ ID NO: 115, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 117;

(j) CDR-H1 comprises the amino acid sequence of SEQ ID NO: 119, CDR-H2 comprises the amino acid sequence of SEQ ID NO: 120, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 122; or (k) CDR-H1 comprises the amino acid sequence of SEQ ID NO: 124, CDR-H2 comprises the amino acid sequence of SEQ ID NO: 125, CDR-H3 comprises the amino acid sequence of SEQ ID NO: 95, CDR-L1 comprises the amino acid sequence of SEQ ID NO: 53, CDR-L2 comprises the amino acid sequence of SEQ ID NO: 54, and CDR-L3 comprises the amino acid sequence of SEQ ID NO: 55.

2. The antibody of claim 1, wherein the antibody comprises a heavy chain variable domain ($V_H$) amino acid sequence having at least 90% identity to a sequence selected from SEQ ID NO: 52, 60, 68, 90, 96, 102, 107, 112, 116, 121, and 126; and/or a light chain variable domain ($V_L$) amino acid sequence having at least 90% identity to a sequence selected from SEQ ID NO: 56, 64, 72, 92, 98, 104, 109, 114, 118, and 123; optionally, wherein:

(a) the antibody comprises a $V_H$ amino acid sequence having at least 90% identity to SEQ ID NO: 52; and a $V_L$ amino acid sequence having at least 90% identity to SEQ ID NO: 56;

(b) the antibody comprises a $V_H$ amino acid sequence having at least 90% identity to SEQ ID NO: 60; and a $V_L$ amino acid sequence having at least 90% identity to SEQ ID NO: 64;

(c) the antibody comprises a $V_H$ amino acid sequence having at least 90% identity to SEQ ID NO: 68; and a $V_L$ amino acid sequence having at least 90% identity to SEQ ID NO: 72;

(d) the antibody comprises a $V_H$ amino acid sequence having at least 90% identity to SEQ ID NO: 90; and a $V_L$ amino acid sequence having at least 90% identity to SEQ ID NO: 92;

(e) the antibody comprises a $V_H$ amino acid sequence having at least 90% identity to SEQ ID NO: 96; and a $V_L$ amino acid sequence having at least 90% identity to SEQ ID NO: 98;

(f) the antibody comprises a $V_H$ amino acid sequence having at least 90% identity to SEQ ID NO: 102; and a $V_L$ amino acid sequence having at least 90% identity to SEQ ID NO: 104;

(g) the antibody comprises a $V_H$ amino acid sequence having at least 90% identity to SEQ ID NO: 107; and a $V_L$ amino acid sequence having at least 90% identity to SEQ ID NO: 109;

(h) the antibody comprises a $V_H$ amino acid sequence having at least 90% identity to SEQ ID NO: 112; and a $V_L$ amino acid sequence having at least 90% identity to SEQ ID NO: 114;

(i) the antibody comprises a $V_H$ amino acid sequence having at least 90% identity to SEQ ID NO: 116; and a $V_L$ amino acid sequence having at least 90% identity to SEQ ID NO: 118;

(j) the antibody comprises a $V_H$ amino acid sequence having at least 90% identity to SEQ ID NO: 121; and a $V_L$ amino acid sequence having at least 90% identity to SEQ ID NO: 123; or (k) the antibody comprises a $V_H$ amino acid sequence having at least 90% identity to SEQ ID NO: 126; and a $V_L$ amino acid sequence having at least 90% identity to SEQ ID NO: 56.

3. The antibody of claim 1, wherein the antibody comprises a heavy chain (HC) amino acid sequence having at least 90% identity to a sequence selected from SEQ ID NO: 149, 150, 152, 154, 155, 156, 157, 158, 159, 160, and 161, and/or a light chain (LC) amino acid sequence having at least 90% identity to a sequence selected from SEQ ID NO: 128, 130, 132, 134, 136, 138, 140, 142, 151, and 153; optionally, wherein the antibody comprises:

(a) the HC amino acid sequence of SEQ ID NO: 149, and the LC amino acid sequence of SEQ ID NO: 142;

(b) the HC amino acid sequence of SEQ ID NO: 150, and the LC amino acid sequence of SEQ ID NO: 151;

(c) the HC amino acid sequence of SEQ ID NO: 152, and the LC amino acid sequence of SEQ ID NO: 153;

(d) the HC amino acid sequence of SEQ ID NO: 154, and the LC amino acid sequence of SEQ ID NO: 128;

(e) the HC amino acid sequence of SEQ ID NO: 155, and the LC amino acid sequence of SEQ ID NO: 130;

(f) the HC amino acid sequence of SEQ ID NO: 156, and the LC amino acid sequence of SEQ ID NO: 132;

(g) the HC amino acid sequence of SEQ ID NO: 157, and the LC amino acid sequence of SEQ ID NO: 134;

(h) the HC amino acid sequence of SEQ ID NO: 158, and the LC amino acid sequence of SEQ ID NO: 136;

(i) the HC amino acid sequence of SEQ ID NO: 159, and the LC amino acid sequence of SEQ ID NO: 138;

(j) the HC amino acid sequence of SEQ ID NO: 160, and the LC amino acid sequence of SEQ ID NO: 140;

(k) the HC amino acid sequence of SEQ ID NO: 161, and the LC amino acid sequence of SEQ ID NO: 142.

4. The antibody of claim 1, wherein the antibody comprises a heavy chain (HC) fused via a linker to a cytokine selected from IL2, IL7, IL10, IL12, IL15, IL21, or IFN-α; optionally, wherein the linker comprises an amino acid sequence selected from SEQ ID NO: 74, 75, 76, 77, 78, and 79.

* * * * *